(12) United States Patent
Setton et al.

(10) Patent No.: US 12,213,997 B1
(45) Date of Patent: Feb. 4, 2025

(54) COMPOSITIONS AND METHODS FOR SUPPORTING NUCLEUS PULPOSUS (NP) CELL PHENOTYPE AND BIOSYNTHESIS

(71) Applicants: Lori Setton, St. Louis, MO (US); Marcos Barcellona, St. Louis, MO (US); Julie Speer, St. Louis, MO (US)

(72) Inventors: Lori Setton, St. Louis, MO (US); Marcos Barcellona, St. Louis, MO (US); Julie Speer, St. Louis, MO (US)

(73) Assignee: Washington University, St. Louis, MO (US)

( * ) Notice: Subject to any disclaimer, the term of this patent is extended or adjusted under 35 U.S.C. 154(b) by 265 days.

(21) Appl. No.: 17/165,011

(22) Filed: Feb. 2, 2021

Related U.S. Application Data

(60) Provisional application No. 62/969,982, filed on Feb. 4, 2020.

(51) Int. Cl.
| | |
|---|---|
| A61K 35/32 | (2015.01) |
| A61K 35/545 | (2015.01) |
| A61K 47/60 | (2017.01) |
| C07K 14/78 | (2006.01) |
| C12N 5/077 | (2010.01) |

(52) U.S. Cl.
CPC ............ *A61K 35/32* (2013.01); *A61K 35/545* (2013.01); *A61K 47/60* (2017.08); *C07K 14/78* (2013.01); *C12N 5/0654* (2013.01)

(58) Field of Classification Search
None
See application file for complete search history.

(56) References Cited

U.S. PATENT DOCUMENTS

| | | | |
|---|---|---|---|
| 9,011,545 | B2 | 4/2015 | Nakamura et al. |
| 9,549,962 | B2 | 1/2017 | Berlemann et al. |
| 2008/0071379 | A1 | 3/2008 | Rydell et al. |
| 2012/0276008 | A1 | 11/2012 | Walkenhorst et al. |
| 2012/0282697 | A1 | 11/2012 | Henry et al. |
| 2013/0052155 | A1 | 2/2013 | Marcolongo et al. |
| 2018/0346902 | A1 | 12/2018 | Jansen et al. |

OTHER PUBLICATIONS

Francisco et al. (2014, Acta Biomaterialia 10:1102-1111).*
Kikkawa et al. (2013, Cell Adhesion & Migration 7(1): 150-159).*
Gonçalves (2019, Master's Thesis, Faculdade de Engenharia da Universidade do Porto, Instituto de Ciências Biomédicas Abel Salazar).*
Bridgen et al. (2017, Acta Biomaterialia 55:100-108).*
"Peptide," https://www.oxfordlearnersdictionaries.com/us/definition/english/peptide#:~:text=%2F%CB%88pepta%C9%AAd%2F-,%2F%CB%88pepta%C9%AAd%2F,more%20amino%20acids%20joined%20together (accessed Aug. 14, 2023).*
Adams, M.A. & Roughley, P.J. (2006) What is Intervertebral Disc Degeneration, and What Causes It? *Spine (Phila. Pa. 1976).* vol. 31, No. 18, pp. 2151-2161.
Aker, L. et al. (2017) Molecular Biology and Interactions in Intervertebral Disc Development, Homeostasis, and Degeneration, with Emphasis on Future Therapies : A Systematic Review. *Spine Sch.* vol. 1, No. 1, pp. 2-20.
Ali, S.A. (2014) Hedgehog Signaling Modulates Cholesterol Homeostasis in Chondrocytes and in Osteoarthritis. Dissertation deposited at University of Toronto, retrieved from https://tspace.library.utoronto.ca/bitstream/1807/74488/3/Ali_Shabana_A_201411_PhD_thesis.pdf on Dec. 3, 2021. 201 pages.
Alonso, R. et al. (2005) Diacylglycerol Kinase a Regulates the Secretion of Lethal Exosomes Bearing Fas Ligand during Activation induced Cell Death of T Lymphocytes. *J. Biol. Chem.* vol. 280, No. 31, pp. 28439-28450.
Bai, X.-H. (2014) XB130—A Novel Adaptor Protein: Gene, Function, and Roles in Tumorigenesis. *Scientifica* (Cairo). Vvol. 2014, No. 903014, 9 pages.
Balaoing, L.R et al. (2015) Laminin Peptide-Immobilized Hydrogels Modulate Valve Endothelial Cell Hemostatic Regulation. *PLOS One,* vol. 10, No. 6, 16 pages.
Bangasser B.L., et al. (2017) Shifting the optimal stiffness for cell migration. *Nat. Commun.* vol. 8, No. 15313, 10 pages.
Barcellona, M.N. et al. (2020) Control of adhesive ligand density for modulation of nucleus pulposus cell phenotype. *Biomaterials.* vol. 250, No. 120057, 20 pages.
Barik, M., Mishra, P.R, & Mohapatra, A.K. (2018) Missing Links Between Genetically Inherited Molecules in Split Cord Malformation and Other Anomaly: A Bench to Bedside Approach., *J. Pediatr. Neurosci.* vol. 13, No. 1, pp. 46-57.
Bidarra, S.J., Barrias, C.C. & Granja, P.L. (2014) Injectable alginate hydrogels for cell delivery in tissue engineering. *Acta Biomater.* vol. 10, No. 4, pp. 1646-1662.
Binch, A., Snuggs, J. & Le Maitre, C.L. (2020) Immunohistochemical analysis of protein expression in formalin fixed paraffin embedded human intervertebral disc tissues. *JOR Spine.* vol. 3, No. e0198, 9 pages.
Bonnevie, E.D. et al. (2019) Aberrant mechanosensing in injured intervertebral discs as a result of boundary-constraint disruption and residual-strain loss. *Nat Biomed Eng.* vol. 3, pp. 998-1008.
Boos, N. et al. (2002) Classification of age-related changes in lumbar intervertebral discs. *Spine (Phila. Pa. 1976).* vol. 27, No. 23, pp. 2631-2644.
Borg, D.J. et al. (2016) Macroporous biohybrid cryogels for co-housing pancreatic islets with mesenchymal stromal cells. *Acta Biomater.* vol. 44, pp. 178-187.
Bowles, R.D. et al. (2010) Self-Assembly of Aligned Tissue-Engineered Annulus and Intervertebral Disc Composite via Collagen Gel Contraction. *Tissue Eng. Part A.* vol. 16, No. 4, pp. 1339-1348.

(Continued)

*Primary Examiner* — Elizabeth C. Kemmerer

(57) ABSTRACT

Among the various aspects of the present disclosure is the provision of compositions and methods for the generation of a supporting matrix for cells, such as stem cells and NP cells (and precursors thereof). For example, an NP cell-specific phenotype precursor cell can be an adult NP cell, such as a cell taken from the adult and degenerated intervertebral disc and/or a progenitor cell, such as stem cells, induced pluripotent cells, pluripotent cells, precursor cells, or stromal cells.

42 Claims, 26 Drawing Sheets
Specification includes a Sequence Listing.

(56) References Cited

OTHER PUBLICATIONS

Bowles, R.D. & Setton L.A. (2017) Biomaterials for intervertebral disc regeneration and repair. *Biomaterials*. vol. 129, pp. 54-67.

Bridgen, D.T. et al. (2013) Integrin-Mediated Interactions with Extracellular Matrix Proteins for Nucleus Pulposus Cells of the Human Intervertebral Disc. *J. Orthop. Res.* vol. 31, No. 10, pp. 1661-1667.

Bridgen, D.T. et al. (2017) Regulation of human nucleus pulposus cells by peptide-coupled substrates. *Acta Biomater*. vol. 55, pp. 100-108.

Budd, E. (2016) MicroRNAs in Osteoarthritis and Chondrogenesis. Dissertation deposited at University of Southampton; Institute of Developmental Health, retrieved from https://eprints.soton.ac.uk/407447/1/Emma_Budd_PhD_THESIS_08_09_2016_MicroRNAs_in_OA_Chondrogenesis_Pdf.pdf on Dec. 6, 2021, 328 pages.

Bult, C.J. et al. (2019) Mouse Genome Database (MGD) 2019. *Nucleic Acids Res*. vol. 47, No. D1, pp. D801-D806.

Burdick, J.A. & Anseth, K.S. (2002) Photoencapsulation of osteoblasts in injectable RGD-modified PEG hydrogels for bone tissue engineering. *Biomaterials*. vol. 23, No. 22, pp. 4315-4323.

Chan, S.C.W., Ferguson, S.J. & Gantenbein-Ritter, B. (2011) The effects of dynamic loading on the intervertebral disc. *Eur. Spine J.* vol. 20, No. 11, pp. 1796-1812.

Chan, W.C.W. et al. (2011) Structure and Biology of the Intervertebral Disk in Health and Disease. *Orthop. Clin. N Am*. vol. 42, No. 4, pp. 447-464.

Chen, J. et al. (2009) Expression of Laminin Isoforms, Receptors, and Binding Proteins Unique to Nucleus Pulposus Cells of Immature Intervertebral Disc. *Connect. Tissue Res*. vol. 50, No. 5, pp. 294-306.

Chen, Z., Liu, J., & Zhang, Y. (2017) Role of Epithelial Cell Transforming Sequence 2 (ECT2) in Predicting Prognosis of Osteosarcoma. *Med. Sci. Monit*. vol. 23, pp. 3861-3868.

Choi, H., Johnson, Z.I., & Risbud, M.V. (2015) Understanding Nucleus Pulposus Cell Phenotype: A Prerequisite for Stem Cell Based Therapies to Treat Intervertebral Disc Degeneration. *Curr. Stem Cell Res. Ther*. vol. 10, No. 4, pp. 307-316.

Cloyd, J. M. et al. (2007) Material properties in unconfined compression of human nucleus pulposus, injectable hyaluronic acid-based hydrogels and tissue engineering scaffolds. *Eur Spine J*. vol. 16, No. 11, pp. 1892-1898.

Colombini, A. et al. (2014) Fibrin in Intervertebral Disc Tissue Engineering. *Tissue Eng Part B Rev*. vol. 20, No. 6, pp. 713-721.

Connelly, J.T., Garcia, A.J., & Levenston M.E. (2008) Interactions between integrin density and cytoskeletal integrity regulate BMSC chondrogenesis, *J. Cell. Physiol*. vol. 217, No. 1, pp. 145-154.

Connelly, J.T. et al. (2010) Actin and serum response factor transduce physical cues from the microenvironment to regulate epidermal stem cell fate decisions. *Nat. Cell Biol*. vol. 12, No. 7, pp. 711-718.

Couchman, J.R. & Woods, A. (1999) Syndecan-4 and integrins: combinatorial signaling in cell adhesion. *J Cell Sci*. vol. 112, Pt. 20, pp. 3415-3420.

Crowder, S.W. et al. (2016) Material Cues as Potent Regulators of Epigenetics and Stem Cell Function. *Cell Stem Cell*. Vol. 18, No. 1, pp. 39-52.

Cui, Y. (2011) Interplay of the osmotic environment and a fibronectin fragment in intervertebral disc cell metabolism. Dissertation deposited at the University of Oxford, retrieved from https://ora.ox.ac.uk/objects/uuid:90c2dec5-7c66-4fd8-9f45-55f8984d41e0/download_file?file_format=pdf&safe_filename=Interplay%2Bof%2Bthe%2Bosmotic%2Benviroment%2Band%2Ba%2Bfibronectin%2Bfragment%2Bin%2Bintervertebral%2Bdisc%2Bcell%2Bmetabolism.pdf&type_of_work=Thesis on Dec. 6, 2021, 231 pages.

Darling, N.J. et al. (2016) Controlling the kinetics of thiol-maleimide Michael-type addition gelation kinetics for the generation of homogenous poly(ethylene glycol) hydrogels. *Biomaterials*. vol. 101, pp. 199-206.

Diez-Roux, G. et al. (2011) A High-Resolution Anatomical Atlas of the Transcriptome in the Mouse Embryo. PLoS Biol. vol. 9, No. 1, e1000582, 13 pages.

Du, L. et al. (2019) Engineering a biomimetic integrated scaffold for intervertebral disc replacement. *Mater Sci Eng C Mater Biol Appl*. vol. 96, pp. 522-529.

Eleftherohorinou, H. et al. (2011) Pathway-driven gene stability selection of two rheumatoid arthritis GWAS identifies and validates new susceptibility genes in receptor mediated signalling pathways. *Hum. Mol. Genet*. vol. 20, No. 17, pp. 3494-3506.

Enemchukwu, N.O. et al. (2016) Synthetic matrices reveal contributions of ECM biophysical and biochemical properties to epithelial morphogenesis. *J. Cell Biol*. vol. 212, No. 1, pp. 113-124.

Engler, A.J. et al. (2006) Matrix Elasticity Directs Stem Cell Lineage Specification. *Cell*. vol. 126, No. 4, pp. 677-689.

Fearing, B.V. et al. (2019) Mechanosensitive transcriptional coactivators MRTF-A and YAP / TAZ regulate nucleus pulposus cell phenotype through cell shape. *FASEB J.* vol. 33, No. 12, pp. 14022-14035.

Fearing, B.V. et al. (2020), Verteporfin treatment controls morphology, phenotype, and global gene expression for cells of the human nucleus pulposus. *JOR Spine*. vol. 3, No. 4, e111, 16 pages.

Fields, A.J., Liebenberg, E.C. & Lotz, J.C. (2014) Innervation of pathologies in the lumbar vertebral end plate and intervertebral disc. *Spine J*. vol. 14, No. 3, pp. 513-521.

Francisco, A.T. et al. (2013) Injectable laminin-functionalized hydrogel for nucleus pulposus regeneration. *Biomaterials*. vol. 34, No. 30, pp. 7381-7388.

Francisco, A.T. et al. (2014) Photocrosslinkable laminin-functionalized polyethylene glycol hydrogel for intervertebral disc regeneration. *Acta Biomater*. vol. 10, No. 3, pp. 1102-1111.

Frauchiger, D.A. et al. (2017) A review of the application of reinforced hydrogels and silk as biomaterials for intervertebral disc repair. *Eur Cells Mat*. vol. 34, No. 34, pp. 271-290.

Freemont, A.J. et al. (1997) Nerve ingrowth into diseased intervertebral disc in chronic back pain. *Lancet*. vol. 350, No. 9072, pp. 178-181.

Fujita, N. et al. (2012) Prolyl hydroxylase 3 (PHD3) modulates catabolic effects of tumor necrosis factor-α (TNF-α) on cells of the nucleus pulposus through co-activation of nuclear factor κB (NF-κB)/p65 signaling. *J. Biol. Chem*. vol. 287, No. 47, pp. 39942-39953.

Gao, L., McBeath, R., & Chen, C.S. (2010) Stem Cell Shape Regulates a Chondrogenic Versus Myogenic Fate Through Rac1 and N-Cadherin. *Stem Cells*. vol. 28, No. 3, pp. 564-572.

Giannattasio, G. et al. (2011) The Purinergic G Protein-Coupled Receptor 6 Inhibits Effector T Cell Activation in Allergic Pulmonary Inflammation. *J. Immunol*. vol. 187, No. 3, pp. 1486-1495.

Gilchrist, C.L. et al. (2011) Extracellular matrix ligand and stiffness modulate immature nucleus pulposus cell-cell interactions. *PLoS One*. vol. 6, No. 11, e27170, 9 pages.

Gullbrand, S.E. et al. (2017) Translation of an injectable triple-interpenetrating-network Hydrogel for Intervertebral Disc Regeneration in a Goat Model. *Acta Biomater*. vol. 60, pp. 201-209.

Hiyama, A. et al. (2011) Hypoxia Activates the Notch Signaling Pathway in Cells of the Intervertebral Disc. *Arthritis Rheum*. vol. 63, No. 5, pp. 1355-1364.

Hong, X. et al. (2018) Cytoplasmic Vacuoles within Notochordal Nucleus Pulposus Cells: A Possible Regulator of Intracellular Pressure That Shapes the Cytoskeleton and Controls Proliferation. *Cells Tissues Organs*. vol. 206, No. 1-2, pp. 9-15.

Hossain, S., Mineno, K., & Katafuchi, T. (2016) Neuronal Orphan G-Protein Coupled Receptor Proteins Mediate Plasmalogens-Induced Activation of ERK and Akt Signaling. *PLoS One*. vol. 11, No. 3, e0150846, 14 pages.

Hozumi, K. et al. (2010) Syndecan- and integrin-binding peptides synergistically accelerate cell adhesion. *FEBS Lett*. vol. 584, No. 15, pp. 3381-3385.

Huebsch, N. et al. (2010) Harnessing traction-mediated manipulation of the cell/matrix interface to control stem-cell fate. *Nat Mater*. vol. 9, No. 6, pp. 518-526.

Huebsch, N. (2019) Translational mechanobiology: Designing synthetic hydrogel matrices for improved in vitro models and cell-based therapies. *Acta Biomater*. vol. 94, pp. 97-111.

Hughes, C.E. & Nibbs, R.J.B. (2018) A guide to chemokines and their receptors. *FEBS J*. vol. 285, No. 16, pp. 2944-2971.

(56) References Cited

OTHER PUBLICATIONS

Humphrey, J.D., Dufresne, E.R., & Schwartz, M.A. (2014) Mechanotransduction and extracellular matrix homeostasis. *Nat. Rev. Mol. Cell Biol.* vol. 15, pp. 802-812.

Hwang, P.Y. et al. (2014) N-Cadherin-Mediated Signaling Regulates Cell Phenotype for Nucleus Pulposus Cells of the Intervertebral Disc. *Cell and Mol Bioeng.* vol. 8, No. 1, pp. 51-62.

Hwang, P.Y. et al. (2016) N-cadherin is Key to Expression of the Nucleus Pulposus Cell Phenotype under Selective Substrate Culture Conditions. *Sci. Rep.* vol. 6, 28038, 14 pages.

Iatridis, J.C. et al. (1996) Is the Nucleus Pulposus a Solid or a Fluid? Mechanical Behaviors of the Nucleus Pulposus of the Human Intervertebral Disc. *Spine (Phila. Pa. 1976).* vol. 21, No. 10, pp. 1174-1184.

Iatridis, J.C. et al. (1997) Alterations in the Mechanical Behavior of the Human Lumbar Nucleus Pulposus with Degeneration and Aging. *J. Orthop. Res.* vol. 15, No. 2, 318-322.

Iatridis, J.C. et al. (1998) Degeneration affects the anisotropic and nonlinear behaviors of human anulus fibrosus in compression. *J Biomech.* vol. 31, No. 6, pp. 535-544.

Ishiguro, H. et al. (2019) Intervertebral disc regeneration with an adipose mesenchymal stem cell-derived tissue-engineered construct in a rat nucleotomy model. *Acta Biomater.* vol. 87, pp. 118-129.

Iwamoto, T. et al. (2006) Monocyte chemoattractant protein-4 (MCP-4)/CCL 13 is highly expressed in cartilage from patients with rheumatoid arthritis. *Rheumatology.* vol. 45, No. 4, pp. 421-424.

Jang, J-H et al. (2018) Novel analgesic effects of melanin-concentrating hormone on persistent neuropathic and inflammatory pain in mice. *Sci. Rep.* vol. 8, No. 1, 707, 17 pages.

Jeong, C.G. et al. (2014) Screening of hyaluronic acid-poly(ethylene glycol) composite hydrogels to support intervertebral disc cell biosynthesis using artificial neural network analysis. *Acta Biomater.* vol. 10, No. 8, pp. 3421-3430.

Jing, J. et al. (2015) Annexin V-induced rat Leydig cell proliferation involves Ect2 via RhoA/ROCK signaling pathway. *Sci. Rep.* vol. 5, No. 9437, 7 pages.

Johnson, Z.I. et al. (2017) TNF-$\alpha$ promotes nuclear enrichment of the transcription factor TonEBP/NFAT5 to selectively control inflammatory but not osmoregulatory responses in nucleus pulposus cells. *J. Biol. Chem.* vol. 292, No. 42, pp. 17561-17575.

Karimi, F. et al. (2018) Integrin Clustering Matters: A Review of Biomaterials Functionalized with Multivalent Integrin-Binding Ligands to Improve Cell Adhesion, Migration, Differentiation, Angiogenesis, and Biomedical Device Integration. *Adv Healtc Mater.* vol. 7, No. 12, e1701324, 28 pages.

Kauppila, L.I. (1995) Ingrowth of Blood Vessels in Disc Degeneration. *J. Bone Jt. Surg.* vol. 77, No. 1, pp. 26-31.

Kikkawa, Y. et al. (2013) Laminin-111-derived peptides and cancer. *Cell Adh Migr.* vol. 7, No. 1, pp. 150-159.

Kilian, K.A. et al. (2010) Geometric cues for directing the differentiation of mesenchymal stem cells. *Proc. Natl. Acad. Sci.* vol. 107, No. 11, pp. 4872-4877.

Kilian, K.A. & Mrksich, M. (2012) Directing stem cell fate by controlling the affinity and density of ligand receptor interactions at the biomaterials interface. *Angew. Chemie—Int. Ed.* vol. 51, No. 20, pp. 4891-4895.

Kim, T. et al. (2009) Identification of LRRc17 as a Negative Regulator of Receptor Activator of NF-κB Ligand (RANKL)-induced Osteoclast Differentiation. *J. Biol. Chem.* vol. 284, No. 22, pp. 15308-15316.

Korecki, C.L., Costi, J.J. & Iatridis, J.C. (2008) Needle Puncture Injury Affects Intervertebral Disc Mechanics and Biology in an Organ Culture Model. *Spine(Phila. Pa. 1976).* vol. 33, No. 3, pp. 235-241.

Koyanagi, S. et al. (2016) Glucocorticoid regulation of ATP release from spinal astrocytes underlies diurnal exacerbation of neuropathic mechanical allodynia. *Nat. Commun.* vol. 7, No. 13102, 13 pages.

Kringel, D. et al. (2018) A machine-learned analysis of human gene polymorphisms modulating persisting pain points to major roles of neuroimmune processes. *Eur. J. Pain.* vol. 22, No. 10, pp. 1735-1756.

Kupka, J. et al. (2020) Adrenoceptor Expression during Intervertebral Disc Degeneration. *Int. J. Mol. Sci.* vol. 21, No. 6, 2085, 15 pages.

Leblanc, K.T. (2013) Runx Expression in Normal and Osteoarthritic Cartilage: Possible Functions of Runx Proteins in Chondrocytes: A Dissertation. University of Massachusetts Medical School, accessed from https://escholarship.umassmed.edu/cgi/viewcontent.cgi?article=1656&context=gsbs_diss on Dec. 7, 2021, 139 pages.

Lee, J. (2013) Directing stem cell fate on hydrogel substrates by controlling cell geometry, matrix mechanics and adhesion ligand composition. *Biomaterials.* vol. 34, No. 33, pp. 8140-8148.

Leimer, E.M. et al. (2019) Behavioral Compensations and Neuronal Remodeling in a Rodent Model of Chronic Intervertebral Disc Degeneration. *Nat. Sci. Reports.* vol. 9, No. 3759, 10 pages.

Li, J. et al. (2017) Investigation of bioeffects of G protein-coupled receptor 1 on bone turnover in male mice. *J. Orthop. Transl.* vol. 10, pp. 42-51.

Liu, Z. et al. (2017) Hypoxia-inducible factor-1a mediates aggrecan and collagen π expression via NOTCH1 signaling in nucleus pulposus cells during intervertebral disc degeneration. *Biochem. Biophys. Res. Commun.* vol. 488, No. 3, pp. 554-561.

Lo, C.M. (2000) Cell Movement Is Guided by the Rigidity of the Substrate. Biophys. J. vol. 79, No. 1, pp. 144-152.

Luo, J. et al. (2019) The role of GPCRs in bone diseases and dysfunctions. *Bone Res.* vol. 7, No. 19, 19 pages.

Maheshwari, G. et al. (2000) Cell adhesion and motility depend on nanoscale RGD clustering. *J Cell Sci.* vol. 113, Pt 10, pp. 1677-1686.

Maroudas, A. et al. (1975). Factors involved in the nutrition of the human lumbar intervertebral disc: cellularity and diffusion of glucose in vitro. *J Anat.* vol. 120, Pt. 1, pp. 113-130.

Martin, J.T. et al. (2013) Needle puncture injury causes acute and long-term mechanical deficiency in a mouse model of intervertebral disc degeneration. *J. Orthop. Res.* vol. 31, No. 8, pp. 1276-1282.

Masuda, K. et al. (2005) A Novel Rabbit Model of Mild, Reproducible Disc Degeneration by an Anulus Needle Puncture: Correlation Between the Degree of Disc Injury and Radiological and Histological Appearances of Disc Degeneration. *Spine (Phila. Pa. 1976).* vol. 30, No. 1, pp. 5-14.

McBeath, R. et al. (2004) Cell Shape, Cytoskeletal Tension, and RhoA Regulate Stem Cell Lineage Commitment. *Dev. Cell.* vol. 6, No. 4, pp. 483-495.

McLeod, C.M. & Mauck, R.L. (2016) High fidelity visualization of cell-to-cell variation and temporal dynamics in nascent extracellular matrix formation. *Sci. Rep.* vol. 6, No. 38852, 12 pages.

Mitra, A. et al. (2017) Cell geometry dictates TNF$\alpha$-induced genome response. *Proc. Natl. Acad. Sci.* vol. 114, No. 20, pp. E3882-E3891.

Miyagi, M. et al. (2011) Disk Injury in Rats Produces Persistent Increases in Pain-Related Neuropeptides in Dorsal Root Ganglia and Spinal Cord Glia but Only Transient Increases in Inflammatory Mediators. *Spine (Phila. Pa. 1976).* vol. 36, No. 26, pp. 2260-2266.

Mizuno, H. et al. (2004) Tissue-Engineered Composites of Anulus Fibrosus and Nucleus Pulposus for Intervertebral Disc Replacement. *Spine (Phila. Pa. 1976).* vol. 29, No. 12, pp. 1290-1298.

Mohanty, S. et al. (2019) Chondrocyte—like nested cells in the aged intervertebral disc are late-stage nucleus pulposus cells. *Aging Cell.* vol. 18, No. 5, e13006, 5 pages.

Mohd Isa, I. L. et al. (2018) Implantation of hyaluronic acid hydrogel prevents the pain phenotype in a rat model of intervertebral disc injury. *Sci. Adv.* vol. 4, No. 4, eaaq0597, 20 pages.

Mok, G.F. et al. (2020) Characterising open chromatin identifies novel cis-regulatory elements important for paraxial mesoderm formation and axis extension. *BioRxiv.* Accessed from https://www.biorxiv.org/content/10.1101/2020.01.20.912337v2.full on Jan. 11, 2022. 33 pages.

Mroue, R. & Bissell, M. J. (2013) Three-Dimensional Cultures of Mouse Mammary Epithelial Cells. *Methods Mol. Biol.* vol. 945, pp. 221-250.

(56) References Cited

OTHER PUBLICATIONS

Nagae, M. et al. (2007) Intervertebral Disc Regeneration Using Platelet-Rich Plasma and Biodegradable Gelatin Hydrogel Microspheres. *Tissue Eng.* vol. 13, No. 1, pp. 147-158.

Nerlich, A.G. et al. (2006) Temporo-spatial distribution of blood vessels in human lumbar intervertebral discs. *Eur Spine* vol. 16, No. 4, pp. 547-555.

Nguyen, M. et al. (2017), Retinoic acid receptor regulation of epimorphic and homeostatic regeneration in the axolotl. *Development.* vol. 144, No. 4, pp. 601-611.

Nilsson, E., Nakamae, T. & Olmarker, K. (2011) Pain Behavior Changes Following Disc 5 Puncture Relate to Nucleus Pulposus Rather than to the Disc Injury Per Se: An Experimental Study in Rats. *Open Orthop. J.* vol. 5, pp. 72-77.

O'Brien, L. E., Zegers, M. M. P. & Mostov, K. E. (2002) Building epithelial architecture: insights from three-dimensional culture models. *Nat. Rev. Mol. Cell Biol.* vol. 3, No. 7, pp. 531-537.

Park, E.J. et al. (2014) Indispensable Platforms for Bioimmobilization: Maleimide-Based Thiol Reactive Hydrogels. *Bioconjug Chem.* vol. 25, No. 11, pp. 2004-2011.

Pattappa, G. et al. (2012) Diversity of intervertebral disc cells: phenotype and function. *J. Anat.* vol. 221, No. 6, pp. 480-496.

Rajesh, D. & Dahia, C. L. (2018) Role of Sonic Hedgehog Signaling Pathway in Intervertebral Disc Formation and Maintenance. *Curr Mol Biol Rep.* vol. 4, No. 4, pp. 173-179.

Rattner, A. et al. (2013) Endothelin-2 signaling in the neural retina promotes the endothelial tip cell state and inhibits angiogenesis. *Proc. Natl. Acad. Sci.* vol. 110, No. 40, pp. E3830-E3839.

Resutek, L. & Hsieh, A. H. (2019) The vacuolated morphology of chordoma cells is dependent on cytokeratin intermediate filaments. *Cell. Physiol.* vol. 234, No. 4, pp. 3458-3468.

Riquier, S. et al. (2020), Detailed analysis of public RNAseq data and long non-coding RNA: a proposed enhancement to mesenchymal stem cell characterization. *BioRxiv Genomics.* Accessed from https://www.biorxiv.org/content/10.1101/2020.03.09.976001v1 on Jan. 11, 2022. 113 pages.

Risbud, M.V. et al. (2015) Defining the Phenotype of Young Healthy Nucleus Pulposus Cells: Recommendations of the Spine Research Interest Group at the 2014 Annual ORS Meeting. *J Orthop Res.* vol. 33, No. 3, pp. 283-293.

Rodrigues-Pinto, R. et al. (2018) Human notochordal cell transcriptome unveils potential regulators of cell function in the developing intervertebral disc. *Sci. Rep.* vol. 8, No. 1, 12866, 13 pages.

Roughley, P.J. (2004) Biology of intervertebral disc aging and degeneration: involvement of the extracellular matrix. *Spine (Phila. Pa. 1976).* vol. 29, No. 23, pp. 2691-2699.

Rouillard, A.D. et al. (2016) The harmonizome: a collection of processed datasets gathered to serve and mine knowledge about genes and proteins. *Database.* vol. 2016, baw100, 16 pages.

Sasson, A. et al. (2012) Hyperelastic mechanical behavior of chitosan hydrogels for nucleus pulposus replacement-experimental testing and constitutive modeling. *J Mech Behav Biomed Mater.* vol. 8, pp. 143-153.

Satoh, S. & Lipton, S. (2017) Recent advances in understanding NRF2 as a druggable target: development of pro-electrophilic and non-covalent NRF2 activators to overcome systemic side effects of electrophilic drugs like dimethyl fumarate. *F1000Research.* vol. 6, No. 2138, 10 pages.

Setton, L.A. & Chen, J. (2006) Mechanobiology of the Intervertebral Disc and Relevance to Disc Degeneration. *J. Bone Jt. Surg.* vol. 88, Suppl. 2, pp. 52-57.

Smith, L.J. et al. (2018) Advancing cell therapies for intervertebral disc regeneration from the lab to the clinic: Recommendations of the ORS spine section. *JOR Spine* vol. 1, No. 4, e1036, 14 pages.

Sohn, P. et al. (2010) Molecular profiling of the developing mouse axial skeleton: a role for Tgfbr2 in the development of the intervertebral disc. *BMC Dev. Biol.* vol. 10, No. 29, 15 pages.

Southern, C. et al. (2013) Screening β-Arrestin Recruitment for the Identification of Natural Ligands for Orphan G-Protein-Coupled Receptors. *J. Biomol. Screen.* vol. 18, No. 5, pp. 599-609.

Sozzani, S. et al. (2015) Chemokines as effector and target molecules in vascular biology. *Cardiovasc. Res.* vol. 107, No. 3, pp. 364-372.

Speichert, S. et al. (2019) Role of Norepinephrine in IL-1β-Induced Chondrocyte Dedifferentiation under Physioxia. *Int. J. Mol. Sci.* vol. 20, No. 5, 1212, 16 pages.

Szklarczyk, D. et al. (2019) STRING v11: protein-protein association networks with increased coverage, supporting functional discovery in genome-wide experimental datasets. *Nucleic Acids Res.* vol. 47, No. D1, pp. D607-D613.

Tam, V. et al. (2014) A Comparison of Intravenous and Intradiscal Delivery of Multipotential Stem Cells on the Healing of Injured Intervertebral Disk Architecture nor the Disk Height Index. *J. Orthop. Res.* vol. 32, No. 6, pp. 819-825.

Tang, R. et al. (2018) Differentiation of human-induced pluripotent stem cells into nucleus pulposus-like cells. *Stem Cell Res. Ther.* vol. 9, 61, 12 pages.

Tenn, N.A. (2015) Investigating The Mechanism of Ectopic Mineralization in a Mouse Model of Diffuse Idiopathic Skeletal Hyperostosis (DISH). Dissertation deposited at The University of Western Ontario, accessed from https://ir.lib.uwo.ca/cgi/viewcontent.cgi?article=4581&context=etd on Jan. 11, 2022. 143 pages.

Thorpe, A.A. et al. (2017) Thermally triggered hydrogel injection into bovine intervertebral disc tissue explants induces differentiation of mesenchymal stem cells and restores mechanical function. *Acta Biomater.* vol. 54, pp. 212-226.

Tondreau, T. et al. (2008) Gene expression pattern of functional neuronal cells derived from human bone marrow mesenchymal stromal cells. *BMC Genomics.* vol. 9, No. 166, 11 pages.

Trout, J.J. et al. (1982) Ultrastructure of the human intervertebral disc. I. Changes in notochordal cells with age. *Tissue Cell.* vol. 14, No. 2, pp. 359-369.

Tsujimoto, T. et al. (2018) An acellular bioresorbable ultra-purified alginate gel promotes intervertebral disc repair: A preclinical proof-of-concept study. *EBioMedicine.* vol. 37, pp. 521-534.

Uhlen, M. et al. (2015) Tissue based map of the human proteome. *Science.* vol. 347, No. 6220, 1260419, 11 pages.

Urban, J P.G. & Roberts, S. (2003) Degeneration of the intervertebral disc. *Arthritis Res. Ther.* vol. 5, No. 3, pp. 120-130.

US Burden of Disease Collaborators (2013) The State of US Health. 1990-2010. *JAMA.* vol. 310, No. 6, pp. 591-608.

Vadala, G. et al. (2012) Mesenchymal stem cells injection in degenerated intervertebral disc: cell leakage may induce osteophyte formation. *J. Tissue Eng. Regen. Med.* vol. 6, No. 5, pp. 348-355.

Van Den Akker, G.G.H. et al. (2020) A Membranome-Centered Approach Defines Novel Biomarkers for Cellular Subtypes in the Intervertebral Disc. *Cartilage.* vol. 11, No. 2, pp. 203-220.

Vincent, K. et al. (2019) Aging of mouse intervertebral disc and association with back pain. *Bone.* vol. 123, pp. 246-259.

Walter, B. A. et al. (2017) MR Elastography-derived Stiffness: A Biomarker for Intervertebral Disc Degeneration. *Radiology.* vol. 285, No. 1, pp. 167-175.

Wang, F. et al. (2017) Formation, function, and exhaustion of notochordal cytoplasmic vacuoles within intervertebral disc: current understanding and speculation. *Oncotarget.* vol. 8, No. 34, pp. 57800-57812.

Wang, Y. et al. (2018) Bioinformatics analysis reveals different gene expression patterns in the annulus fibrosis and nucleus pulpous during intervertebral disc degeneration. *Exp. Ther. Med.* vol. 16, No. 6, pp. 5031-5040.

Williams, S., Alkhatib, B., & Serra, R. (2019) Development of the axial skeleton and intervertebral disc, in: *Curr. Top. Dev. Biol.*, 1st ed., Elsevier Inc., pp. 49-90.

Woiciechowsky, C. et al. (2014) Regeneration of nucleus pulposus tissue in an ovine intervertebral disc degeneration model by cell-free resorbable polymer scaffolds. *J. Tissue Eng. Regen. Med.* vol. 8, No. 10, pp. 811-820.

Wu, Y. et al. (2017) Oxytocin prevents cartilage matrix destruction via regulating matrix metalloproteinases. *Biochem. Biophys. Res. Commun.* vol. 486, No. 3, pp. 601-606.

Yuen, T.J. et al. (2013) Identification of endothelin 2 as an inflammatory factor that promotes central nervous system remyelination. *Brain.* vol. 136, Pt. 4, pp. 1035-1047.

(56) References Cited

OTHER PUBLICATIONS

Zandi-Nejad, K. et al. (2013) The role of HCA2 (GPR109A) in regulating macrophage function. *FASEB J.* vol. 27, No. 11, pp. 4366-4374.

Zhang, Y. et al. (2020) Directed Differentiation of Notochord-like and Nucleus Pulposus-like Cells Using Human Pluripotent Stem Cells. *Cell Rep.* vol. 30, No. 8, pp. 2791-2806.e5.

Zhao, C. et al. (2020) Identification of significant gene biomarkers of low back pain caused by changes in the osmotic pressure of nucleus pulposus cells. *Sci. Rep.* vol. 10, No. 3708, 19 pages.

Zhou, X. et al. (2018) Injectable decellularized nucleus pulposus-based cell delivery system for differentiation of adipose-derived stem cells and nucleus pulposus regeneration. *Acta Biomater.* vol. 81, pp. 115-128.

Zhu, J. (2010) Bioactive modification of poly(ethylene glycol) hydrogels for tissue engineering. *Biomaterials.* vol. 31, No. 17, pp. 4639-4656.

Zorina-Lichtenwalter, K. et al. (2016) Genetic predictors of human chronic pain conditions. *Neuroscience.* vol. 338, pp. 36-62.

\* cited by examiner

A.

B.

C.

D.

E.

COMPOSITIONS AND METHODS FOR SUPPORTING NUCLEUS PULPOSUS (NP) CELL PHENOTYPE AND BIOSYNTHESIS

CROSS-REFERENCE TO RELATED APPLICATIONS

This application claims priority from U.S. Provisional Application Ser. No. 62/969,982 filed on 4 Feb. 2020, which is incorporated herein by reference in its entirety.

STATEMENT REGARDING FEDERALLY SPONSORED RESEARCH OR DEVELOPMENT

This invention was made with government support under AR069588 and AR047442 awarded by the National Institutes of Health and under DGE1745038 awarded by the National Science Foundation. The government has certain rights in the invention.

MATERIAL INCORPORATED-BY-REFERENCE

The Sequence Listing, which is a part of the present disclosure, includes a computer readable form comprising nucleotide and/or amino acid sequences of the present invention (019297-US-NP_Sequence_Listing_ST25.txt created on 21 Jun. 2021, 1,657 bytes). The subject matter of the Sequence Listing is incorporated herein by reference in its entirety.

FIELD OF THE INVENTION

The present disclosure generally relates to compositions of and methods for biomaterial scaffolds for the support of cells (e.g., human nucleus pulposus (NP) cells) in order to promote their biosynthesis and NP-specific phenotype.

SUMMARY OF THE INVENTION

Among the various aspects of the present disclosure is the provision of compositions and methods for the support of nucleus pulposus (NP) cell phenotype or biosynthesis.

An aspect of the present disclosure provides for a biocompatible composition comprising: a biocompatible polymer component; and/or at least one cell-adhesive peptide. In some embodiments, the cell-adhesive peptide is coupled to the biocompatible polymer component to form a cell-adhesive peptide-functionalized monomer; and/or the cell-adhesive peptide-functionalized monomer is crosslinked to form a cell-adhesive peptide-functionalized polymer.

In some embodiments, the biocompatible polymer component comprises a PEG, a linear PEG, multi-arm star PEG, PEG maleimide, or other biocompatible polymer.

In some embodiments, the cell-adhesive peptide is derived from a sequence found in naturally occurring laminin proteins, a functional portion of the LG domains of full length laminin, isoforms thereof, or a functional fragment or variant thereof.

In some embodiments, the cell-adhesive peptide is a laminin-mimetic peptide.

In some embodiments, the laminin-mimetic peptide is a laminin-based integrin-binding peptide or a laminin-based syndecan-binding peptide.

In some embodiments, the cell-adhesive peptide is a cadherin-binding peptide.

In some embodiments, the cell-adhesive peptide is selected from at least one of a syndecan-binding peptide or an integrin-binding peptide.

In some embodiments, the composition comprises a first integrin-binding peptide and a second integrin-binding peptide.

In some embodiments, the syndecan-binding peptide is AG73 or a functional variant or fragment thereof.

In some embodiments, the integrin-binding peptide is YIGSR, IKVAV, P4, A5G81, or GD6, or a functional variant or fragment thereof.

In some embodiments, the biocompatible polymer component comprises a terminal component (e.g., maleimide, cysteine, carboxylate) capable of conjugating a cell-adhesive peptide.

In some embodiments, the cell-adhesive peptide-functionalized monomer is crosslinked via coupling of the biocompatible polymer component via side group coupling, a terminal group on the biocompatible polymer component, a sulfo-, a dithiol crosslinker, a PEG crosslinker, an amine, or EDC/NHS coupling.

In some embodiments, the dithiol crosslinker is SH-PEG-SH, optionally having a molecular weight of between about 5 K and about 20 K.

In some embodiments, if the cell-adhesive peptide density is increased, the biocompatible composition stiffness increases.

In some embodiments, the biocompatible composition has a stiffness of between about 0.1 kPa and about 50 kPa.

In some embodiments, the cell-adhesive peptide is between about 5 and about 30 amino acids long.

In some embodiments, the cell-adhesive peptide comprises a terminal group capable of conjugating to a biocompatible polymer component comprising a bioconjugation component capable of conjugating with the terminal group.

In some embodiments, the cell-adhesive peptide comprises a thiol terminal group capable of conjugating to a biocompatible polymer component comprising maleimide.

In some embodiments, the at least one cell-adhesive peptide is a combination of a syndecan-binding peptide and/or an integrin-binding peptide.

In some embodiments, the at least one cell-adhesive peptide is at least two of integrin-binding, syndecan-binding, or cadherin-binding peptides.

In some embodiments, the cell-adhesive peptide is a laminin-mimetic peptide comprising a sequence selected from the group consisting of RKRLQVQLSIRT (SEQ ID NO: 1), RARKQAASIKVAVSADR (SEQ ID NO: 2), PPFLMLLKGSTR (SEQ ID NO: 3), EGYGEGYIGSR (SEQ ID NO: 4), AGQWHRVSRWG (SEQ ID NO: 5), KQNCLSSRASFRGCVRNLRLSR (SEQ ID NO: 6), and combinations, functional fragments, or functional variants thereof.

In some embodiments, the biocompatible composition comprises a cell-adhesive peptide-functionalized polymer density between about 2% (w/v) and about 40% (w/v).

In some embodiments, the biocompatible composition comprises a cell-adhesive peptide density sufficient to support NP cell-specific morphology, biosynthesis, or phenotype for or differentiation of progenitor cells towards expression of an NP cell-specific morphology, biosynthesis, or phenotype.

In some embodiments, the cell-adhesive peptide density is between about 10 μM and about 1000 μM.

In some embodiments, the composition further comprises a population of undifferentiated precursor cells, a population of stem cells, a population of nucleus pulposus (NP) cell precursors, a population of adult primary NP cells, or a population of primary intervertebral disc (IVD) cells, or a combination thereof.

In some embodiments, the NP cell precursors are NP progenitor cells.

In some embodiments, the biocompatible composition comprises a cell having an NP cell-specific phenotype characterized by the gene expression of COL1A1, ACAN, COL2A1, GLUT1, or CDH2, or combinations thereof.

In some embodiments, the biocompatible composition comprises a population of NP cell-specific phenotype precursor cells selected from IVD cells, primary adult NP cells, NP precursor cells, adult NP cells, or pathological NP cells, or combinations thereof.

In some embodiments, the NP cell precursors are undifferentiated precursor cells.

In some embodiments, wherein the composition further comprises at least one progenitor cell in its undifferentiated state.

In some embodiments, the biocompatible composition further comprises stem cells selected from adipose stromal/stem cells (ASCs), adipose-derived stem cells (ADSCs), amniotic fluid stem cells, bone marrow-derived mesenchymal stem/stromal cells (BMSCs), bone marrow stem cells, cord blood stem cells, embryonic stem (ES) cells, hematopoietic stem cells, induced pluripotent stem cells (iPSCs), mesenchymal stromal, non-embryonic (adult) stem cells, pluripotent stem cells (PSCs), progenitor cells, induced pluripotent stem (iPS) cells), induced pluripotent stem cells (iPSCs), mesenchymal stromal cells, mesenchymal stem cells (MSCs), cord blood stem cells, umbilical cord-derived progenitor cells, umbilical cord-MSCs, umbilical cord-derived progenitor cells, amniotic fluid stem cells, or other progenitor cells.

In some embodiments, the stem cells promote cell attachment, promote the secretion of inflammatory mediating factors, or promote the secretion of matrix degrading protease mediating factors.

In some embodiments, the factors are selected from IL-1RA, sIL-6R, sTNFRI, STNFRII, TIMP 1, TIMP 2, TIMP 3, or TIMP 4, or a combination thereof.

In some embodiments, the biocompatible composition supports progenitor cell secretions of chemokines that exert an anti-inflammatory effect upon neighboring cells.

In some embodiments, the composition further comprises progenitor cells cultured in or on the biocompatible composition, wherein the progenitor cells secrete inflammatory-mediating factors that result in inflammatory mediating effects upon neighboring cells.

In some embodiments, the inflammatory-mediating factor is selected from IL-1RA, SIL-6R, STNFRI, or sTNFRII, or combinations thereof.

In some embodiments, the composition further comprises progenitor cells cultured in or on the biocompatible composition, wherein the progenitor cells secrete protease mediating factors, optionally, tissue degrading proteases, which result in protease mediating effects upon neighboring cells.

In some embodiments, the tissue degrading protease is selected from TIMP1, TIMP2, TIMP3, or TIMP4, or combinations thereof.

In some embodiments, the biocompatible composition supports progenitor cells capable of secreting extracellular matrix biosynthesis promoting chemokines within neighboring cells.

In some embodiments, anabolic effects are achieved through secretion of extracellular matrix proteins.

In some embodiments, the biocompatible composition comprises a peptide density and/or spacing capable of promoting cell attachment and/or differentiation of NP cell precursors or progenitor cells towards healthy NP cell-specific phenotype or biosynthesis, respectively.

In some embodiments, the biocompatible composition is suitable for use as an injectable material mixed with cells or cell-free, wherein the biocompatible composition has a viscosity that does not exceed G' of 100 Pa and G" of 25 Pa (2.5 Hz) at temperatures between about 4° C. and about 37° C.

In some embodiments, the biocompatible composition is suitable for delivery to a defect site when injected in its precursor form mixed with cells or cell-free through a 12 G-22 G needle.

In some embodiments, the biocompatible composition is a 3D cell supporting matrix or coats a tissue culture surface, optionally well plates or chamber slides.

In some embodiments, the biocompatible composition is capable of being used in cell-polymer culture constructs in vitro in volumes between about 10 mL and about 1 mL and between about 0 million cells/mL and up to about 10 million cells/mL.

In some embodiments, the biocompatible composition delivers cells to an intervertebral disc optionally, to repair damaged tissue, of a subject.

In some embodiments, the cell-adhesive peptide densities and/or co-combinations of coupling to peptide-functionalized polymer components modulate a range of cell phenotypic changes.

In some embodiments, the biocompatible composition supports cell survival, when introduced to a population of cells, in a peptide-functionalized polymer component solution, and/or crosslinked into a three-dimensional construct.

In some embodiments, the biocompatible composition is capable of delivering and/or localizing NP precursor cells or primary human NP cells and/or peptide-functionalized polymer components to defects in an intervertebral disc in a subject.

Another aspect of the present disclosure provides for a method of preparing a biocompatible composition comprising: (i) providing a polymer component; (ii) providing a thiol-terminated peptide (e.g., IKVAV or AG73 peptides); (iii) optionally providing a crosslinking component; (iv) mixing the polymer component and/or the thiol-terminated peptide at a pH of between about 3-3.5 and about 7-7.5, for a period of time, optionally, under 30 seconds, greater than 10 minutes at pH 3-3.5, less than about 10 seconds at pH 7-7.5, sufficient to result in a peptide-functionalized polymer component optionally, a peptide functionalized PEG-maleimide; (v) crosslinking the peptide-functionalized polymer component via a terminal group on a monomer capable of crosslinking or via a PEG-dithiol crosslinker (e.g., SH-PEG-SH) to link the polymer components (e.g., maleimides) having less than about 10% unbound peptide following coupling reaction at a pH of between about 3-3.5 and about 7-7.5; and/or (vi) hydrate (e.g., in 1×PBS with a pH of about 7.4), resulting in a hydrogel.

Yet another aspect of the present disclosure provides for a method of supporting adult human NP cells towards a healthy nucleus pulposus (NP) cell-specific phenotype or delivering undifferentiated progenitor cells comprising administering to a subject the biocompatible composition of any one of the preceding aspects or embodiments.

In some embodiments, the subject has intervertebral disc degeneration or damage.

In some embodiments, the method further comprises seeding cells on or in the biocompatible composition.

In some embodiments, a subject is treated with the biocompatible composition of any one of the preceding aspects or embodiments the subject has a defect in an intervertebral disc, disc herniation, disc stenosis, or disc degeneration.

In some embodiments, culturing NP cell-specific phenotype precursor cells in or on the biocompatible composition promotes cell adhesion or cells expressing markers of juvenile NP cells or healthy NP cells.

In some embodiments, markers of an NP cell-specific phenotype are measured by morphometric value, gene expression, protein expression, vacuole expression, contractile phenotype, or combinations thereof.

In some embodiments, a healthy NP cell-specific phenotype is characterized by gene expression of COL1A1, ACAN, COL2A1, GLUT1, CDH2, or combinations thereof.

In some embodiments, the biocompatible composition comprises human NP cells or stem cells.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figures 1A, 1B, 1C, 1D:
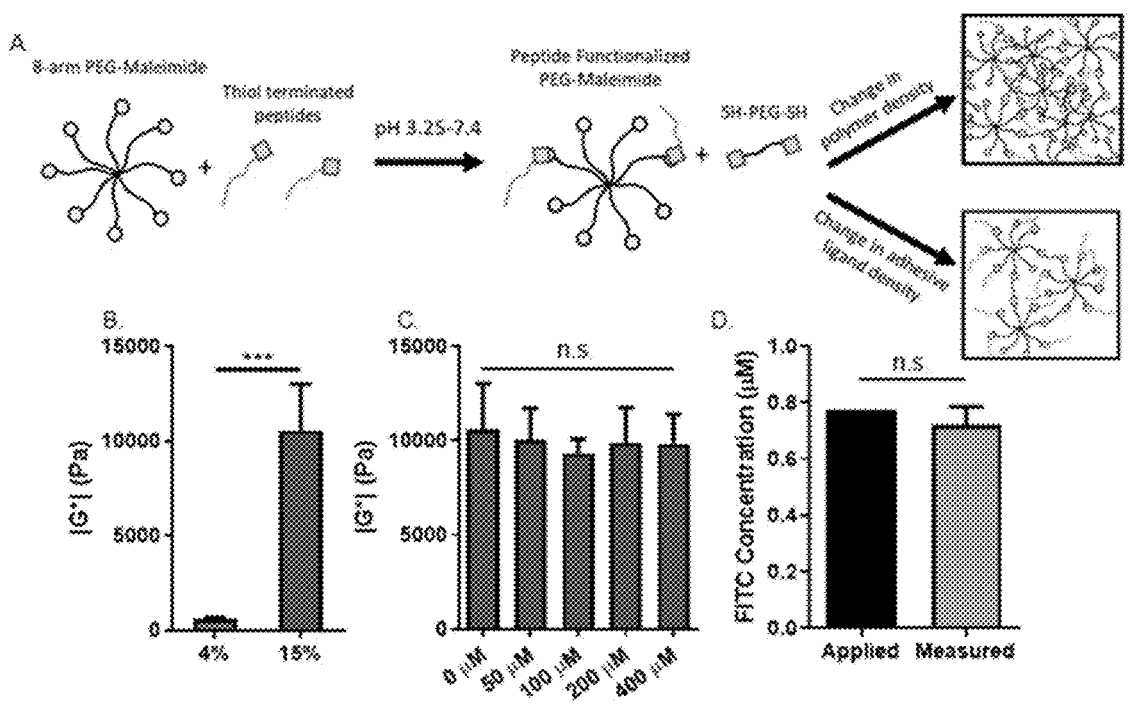
FIG. 1A-FIG. 1D. Schematic of hydrogel formulation and synthesis and mechanical property data presented as mean+/−standard deviation. A) Schematic of poly(ethylene glycol) (PEG) backbone functionalization, hydrogel formation, and control of peptide density or substrate stiffness. B) Soft (4%, red) and stiff (15%, blue) gels have significantly different shear moduli. C) Incorporation of peptides into the PEG backbone does not impact modulus. D) ~90% coupling efficiency was observed using a fluorometric approach. *** $p<0.001$, using t-test (B, D), or one-way ANOVA with Dunnett's multiple comparison's test (C).

The present disclosure is based, at least in part, on the discovery that specific substrate conditions can result in support of nucleus pulposus (NP) cell-specific biosynthesis and phenotype adult degenerated cells or stem cells. More specifically, the compositions and methods described herein result in stiff hydrogels that are similar in appearance to soft hydrogels biologically, by controlling peptide density.

As shown herein, the present disclosure provides for a biocompatible composition comprising a peptide-functionalized polymer that can be used to support the expression of nucleus pulposus (NP) cell-specific phenotypic markers and biosynthesis amongst cells taken from the adult and degenerated intervertebral disc. The peptide-functionalized polymer can similarly be used to promote the expression of nucleus pulposus (NP) cell-specific phenotypic markers and biosynthesis amongst cells of progenitor populations, including stem cells, induced pluripotent cells, pluripotent cells, precursor cells, and stromal cells.

As shown herein, primary adult cells from pathological human nucleus pulposus (NP) tissues that were cultured upon stiff polymer hydrogels functionalized with peptides at densities of 100 µM and 400 µM expressed NP-specific cell and fibroblast-like cell phenotypes, respectively (see e.g., Example 1).

In one embodiment, the peptide-functionalized polymer can serve as a biomaterial for the delivery of undifferentiated precursor cells (e.g., induced pluripotent stem cells (iPSCs), mesenchymal stromal cells, mesenchymal stem cells, bone marrow stem cells, adipose stem cells, umbilical cord-derived progenitor cells, or other progenitor cells) that can secrete factors. Among others, these factors can promote cell attachment, produce inflammatory mediating effects, or produce protease mediating effects. Some of the cytokines or factors that can be secreted to promote cell attachment and/or promote the secretion of inflammatory mediating or matrix degrading protease mediating factors can include but are not limited to IL-1RA, SIL-6R, STNFRI, STNFRII, TIMP 1, TIMP 2, TIMP 3, or TIMP 4.

Polymer-Peptide Conjugate Supporting Material

The present disclosure provides for the development of a biocompatible composition comprising an engineered peptide-functionalized polymer that can be used to support cells (e.g., nucleus pulposus (NP) cell-specific phenotype, progenitor cells, stem cells, etc.) For example, NP cells can be supported to express the NP cell phenotype of the intervertebral disc (IVD).

A multi-arm (e.g., 4, 6, 8-arm star PEG, 5K-40K molecular weight) polymer can be functionalized with the appropriate peptide or combination of peptides via a terminal cysteine on the peptide sequence. Polymer-peptide precursors can be crosslinked via a terminal group on a monomer capable of crosslinking or mixed with a PEG-dithiol crosslinker of variable molecular weight (e.g., 0.5-3.4K) at a targeted pH to form a three-dimensional hydrogel with high control of reaction kinetics (>10 minutes at pH 3-3.5, <10 seconds at pH 7-7.5) that can be used to coat tissue culture surfaces such as well plates, chamber slides, etc., to make cell-polymer culture constructs in vitro, or to deliver cells to the intervertebral disc for repair purposes. The use of acidic ranges of pH, particularly, is unexpected and non-obvious. As such, the time of gelation is controlled by the stoichiometric ratio of reagents, the pH, and the cell density in a non-obvious process.

In particular, the present disclosure describes how by choosing the range of peptide density and co-combinations of coupling to polymer-peptide precursors, a range of cell phenotypic changes (e.g., shape, morphology, gene or protein expression, biosynthesis) can be achieved.

As described herein, culturing primary adult cells from pathological human nucleus pulposus (NP) tissues upon crosslinked polymer-peptide substrates in the range of 10-20% PEG (% w/v) at peptide densities of 50 µM-200 µM (using select combinations of peptides) promoted >80% cell adhesion, with cells expressing markers of the NP cell-specific phenotype, as characterized by morphometric values, and gene and protein expression profiles (see e.g., Example 1). Conversely, substrates of the same polymer concentration (and hence stiffness) functionalized with 400 µM-1000 µM total peptide maintained similar degrees of cell adhesion but led to cells expressing a fibroblast-like phenotype or morphology (characterized by cell morphology, gene, and protein expression) (see e.g., Example 2).

A range of polymer concentrations, peptide densities, and peptide co-combinations useful for various purposes are available. For example, the disclosed compositions can support cell survival when mixed in the polymer-peptide precursor solutions and crosslinked into thick, three-dimensional constructs.

As another example, the disclosed compositions can deliver and localize cells and polymer-peptide to defects in the intervertebral disc in a subject. Delivery of autologous stem cells to the intervertebral disc is a mature industry for treating low back pain and disc pathology (Mesoblast, Biorestorative Therapies, DiscGenics). These cells are commonly delivered with a commercially available biomaterial or no biomaterial at all. There is expanding interest in delivery of progenitor cells as a means to work with allogeneic cell sources. However, means to control the differentiation towards the targeted and biosynthetically active nucleus pulposus (NP) cell type are lacking. As such, the present disclosure provides for a biomaterial that can promote cell attachment and/or expression of the NP cell-specific phenotype and biosynthesis through non-pharmacologic means or for cells of varying sources, including stem cells, pathological human primary IVD cells, and other progenitor cell sources including induced pluripotent stem cells, stromal cells, and others.

The compositions and methods of the present disclosure are of unique interest because the intervertebral disc is a load-bearing structure and so any injectable or implantable biomaterial should have properties of relative stiffness. The presently disclosed compositions and methods allow for the engineering of biomaterials in the broad range of 5 kPa to 50 kPa, which is suitable for integrating with native adult IVD tissue, while supporting and controlling cell behavior through manipulations of peptide combination and density.

"Nucleus pulposus" as used herein refers to the semi-fluid center region of the intervertebral disc. "Intervertebral disc" as used herein refers to the structure located between adjacent vertebrae of the spinal column and includes both the nucleus pulposus and annulus fibrosus. "Hydrogel" as used herein refers to a 3D compound or formulation made from hydrophilic natural or synthetic polymers that can swell and contain water or other media.

Biocompatible Composition

The biocompatible compositions as described herein are prepared by combining peptide solutions with cross-linkable polymer precursor solutions to create hydrogels with tunable mechanical properties. The biocompatible composition can be capable of supporting cells having an NP cell-specific phenotype.

As described herein, the biocompatible composition can comprise a polymer component. The polymer component can be functionalized with a peptide. The peptide-functionalized polymer can be crosslinked. The crosslinked peptide-functionalized polymer can comprise PEG (e.g., linear PEG, star PEG). The biocompatible composition can be a hydrogel. The biocompatible composition can comprise or can be a substrate for cells having an NP cell-specific phenotype.

The biocompatible composition can comprise between about 2% and about 40% total polymer using a multi-arm backbone (e.g., 4, 6, 8 arm star PEG; 5K-40K molecular weight) and a thiolated crosslinker (2, 4-arm linear or star PEG, 0.5-3.4K molecular weight), and peptide concentrations ranging from between about 50 M and about 1000 μM, as described herein. The remainder of the composition can be saline solution or cell culture media. Addition of the thiolated crosslinker allows for the initiation of hydrogel formation.

The biocompatible compositions described herein can allow for control of peptide (ligand) density and spacing. The biocompatible compositions can be prepared in aqueous form prior to cross-linking and do not require external devices for gelation (i.e., UV or other light sources). The biocompatible compositions can be made with or without cells.

The biocompatible composition can be used to form gels extruded through means including but not limited to extrusion through a syringe or a pipet such that the composition may be injected into the intervertebral disc space. The biocompatible compositions can be used for forming 2D or 3D cell culture substrates.

As described herein, the biocompatible composition can have a peptide density (or peptide concentration). The peptide density can be modulated to control cell adhesion and phenotype to mimic that of the healthy or juvenile NP cell. As an example, the peptide density can be between 0 μM and about 1000 μM. As another example, the peptide density can be greater than 0 μM, greater than about 50 μM, greater than about 100 μM, greater than about 200 μM, or greater than about 400 μM. As another example, the peptide density can be about 1 μM; about 10 μM; about 20 μM; about 30 μM; about 40 M; about 50 μM; about 60 μM; about 70 μM; about 80 μM; about 90 μM; about 100 μM; about 110 μM; about 120 μM; about 130 μM; about 140 μM; about 150 μM; about 160 μM; about 170 μM; about 180 μM; about 190 M; about 200 μM; about 210 μM; about 220 μM; about 230 μM; about 240 μM; about 250 μM; about 260 μM; about 270 μM; about 280 μM; about 290 μM; about 300 μM; about 310 μM; about 320 μM; about 330 μM; about 340 μM; about 350 μM; about 360 μM; about 370 μM; about 380 μM; about 390 μM; about 400 μM; about 410 μM; about 420 μM; about 430 μM; about 440 μM; about 450 μM; about 460 μM; about 470 μM; about 480 μM; about 490 μM; about 500 μM; about 510 μM; about 520 μM; about 530 M; about 540 μM; about 550 μM; about 560 μM; about 570 μM; about 580 M; about 590 μM; about 600 μM; about 610 μM; about 620 μM; about 630 μM; about 640 μM; about 650 μM; about 660 μM; about 670 μM; about 680 μM; about 690 μM; about 700 μM; about 710 μM; about 720 μM; about 730 μM; about 740 μM; about 750 μM; about 760 μM; about 770 μM; about 780 μM; about 790 μM; about 800 μM; about 810 μM; about 820 μM; about 830 μM; about 840 μM; about 850 μM; about 860 μM; about 870 μM; about 880 μM; about 890 μM; about 900 μM; about 910 μM; about 920 μM; about 930 μM; about 940 μM; about 950 μM; about 960 μM; about 970 μM; about 980 M; about 990 μM; or about 1000 μM.

As described herein, the biocompatible composition can have % polymer component (% w/v). The polymer component can be modulated to modulate NP cell adhesion and phenotype to mimic that of the healthy NP cell. As an example, the % polymer component can be greater than 0%, between about 2% and about 40%. As another example, the % polymer component can be greater than 0%, greater than about 4%, greater than about 15%, greater than about 20%, or greater than about 40%. As another example, the % polymer component can be about 1%; about 2%; about 3%; about 4%; about 5%; about 6%; about 7%; about 8%; about 9%; about 10%; about 11%; about 12%; about 13%; about 14%; about 15%; about 16%; about 17%; about 18%; about 19%; about 20%; about 21%; about 22%; about 23%; about 24%; about 25%; about 26%; about 27%; about 28%; about 29%; about 30%; about 31%; about 32%; about 33%; about 34%; about 35%; about 36%; about 37%; about 38%; about 39%; about 40%; about 41%; about 42%; about 43%; about 44%; about 45%; about 46%; about 47%; about 48%; about 49%; about 50%; about 51%; about 52%; about 53%; about 54%; about 55%; about 56%; about 57%; about 58%; about 59%; about 60%; about 61%; about 62%; about 63%; about 64%; about 65%; about 66%; about 67%; about 68%; about 69%; about 70%; about 71%; about 72%; about 73%; about 74%; about 75%; about 76%; about 77%; about 78%; about 79%; about 80%; about 81%; about 82%; about 83%; about 84%; about 85%; about 86%; about 87%; about 88%; about 89%; about 90%; about 91%; about 92%; about 93%; about 94%; about 95%; about 96%; about 97%; about 98%; about 99%; or about 100%.

Additional agents, such as a drug, a drug delivery agent, or factors, such as growth factors, can be incorporated into this biocompatible material. These additional agents can be incorporated before, during, or after incorporation of cells into the biocompatible material.

Biocompatible Polymer

A biocompatible polymer, as described herein can be a bioabsorbable, biodissolvable, meltable, biodegradable, or bioerrodable polymer. Some examples of biocompatible polymers that can be incorporated into the biomaterial can be polyether (e.g., polyethylene glycol (PEG), high molecular weight PEG is PEG3350, low molecular weight PEG is PEG400, PEG is aka polyethylene oxide (PEO) or polyoxyethylene (POE), poly(ethylene glycol) (PEG), poly(propylene glycol) (PPG), poly(tetrahydrofuran)); polyester (e.g., polycaprolactone (PCL), polylactide or polylactic acid (PLA), polyglycolide or polyglycolic acid (PGA), poly (lactide-glycolide) (PLGA), poly(propylene fumarate) (PPF), poly(caprolactone fumarate) (PCLF), poly(glycolide-co-caprolactone) (PGCL), poly(L-lactic acid) (PLLA), poly (D-lactic acid) (PDLA), poly(D,L-lactic acid) (PDLLA)—a racemic mixture of PLLA and PDLA, polyortho ester, polyhydroxobutyrate (PHB), meso-poly(lactic acid)); polyamino acids (e.g., poly(γ-glutamic acid) (γ-PGA) and poly(L-lysine), poly(L-glutamic acid) (L-PGA) and poly (aspartic acid) (PAA)); polysaccharides (e.g., hyaluronic acid (HA), chitin, alginate, chitosan); bioerodible polymers (e.g., polyphosphazenes (bulk or surface erosion), polyanhydrides (surface erosion)); vinyl polymer (e.g., polyethylene vinyl acetate (PEVA), polyvinylpyrrolidone (PVP)); natural polymer (e.g., elastin & elastin-like polypeptides, albumin, fibrin, collagen, fibronectin); and copolymers and combinations thereof.

Cell Adhesive Peptides

The biocompatible compositions, as described herein, can comprise a peptide-functionalized polymer material capable of facilitating cell attachment and intracellular signaling. The biocompatible compositions can be used for supporting a variety of cells such as NP cells, NP precursors, NP juvenile cells, pro-juvenile phenotype cells, pro-contractile phenotype cells, primary adult NP cells, induced pluripotent stem cells, mesenchymal stem cells, mesenchymal stromal cells, mesenchymal stem cells, bone marrow stem cells, adipose stem cells, umbilical cord-derived progenitor cells, or other progenitor cells or stem cells. The peptide in the peptide-functionalized hydrogel can comprise cell adhesive peptides, such as peptides derived from laminin (laminin mimetic peptides) (e.g., laminin-derived integrin-binding peptide, a laminin-derived syndecan-binding peptide, or combinations thereof). Laminin-derived cell adhesive peptides can promote cell attachment through syndecan and integrin binding.

As an example, any laminin-derived peptide known in the art can be incorporated into the biomaterial (e.g., conjugated to a polymer component, as described herein). For example, there are peptide sequences identified from the LM-111 protein. As described herein, peptides from LM-111 were used as well as other Laminins (e.g., LM-521 and LM-332). See e.g., Kikkawa et al. (2013) Laminin-111-derived peptides and cancer, Cell Adhesion & Migration, 7:1, 150-159, incorporated herein by reference.

Select combinations of laminin-derived integrin-binding peptide or laminin-derived syndecan-binding cell adhesive peptide can be coupled in precise molar ratios to a multi-arm maleimide-terminated poly(ethylene glycol) (PEG) star monomer (e.g., 4, 6, or 8 arms) via maleimide-thiol coupling to form the polymer-peptide precursor solution.

As an example, a syndecan-binding peptide can comprise the sequence RKRLQVQLSIRT (AG73, SEQ ID NO: 1) with a C terminal group coupled to a variable number of G residues at the N-terminus.

As another example, an integrin-binding peptide can comprise the sequences RARKQAASIKVAVSADR (IKVAV, SEQ ID NO: 2), PPFLMLLKGSTR (P4, SEQ ID NO: 3), EGYGEGYIGSR (YIGSR, SEQ ID NO: 4), AGQWHRVSRWG (A5G81, SEQ ID NO: 5), or KQNCLSSRASFRGCVRNLRLSR (GD6, SEQ ID NO: 6), all with a C terminal group and a variable number of G residues at the N-terminus.

The polymer or hydrogel can be functionalized with between about 50 µM and about 1000 µM peptide(s).

An example of a sequence of amino acids found in naturally occurring laminin includes the syndecan-binding peptide AG73 (ArgLysArgLeuGlnValGlnLeuSerIleArgThr) (SEQ ID NO: 1). Another example of a sequence of amino acids found in naturally occurring laminin includes the integrin-binding peptide IKVAV (ArgAlaArgLysGlnAlaAlaSerIleLysValArgValSerAlaAspArg) (SEQ ID NO: 2). Other examples of laminin mimetic peptides can be P4: PPFLMLLKGSTR (SEQ ID NO: 3); YIGSR: EGYGEGYIGSR (SEQ ID NO: 4); A5G81: AGQWHRVSRWG (SEQ ID NO: 5); or GD6: KQNCLSSRASFRGCVRNLRLSR (SEQ ID NO: 6).

Cells

As described herein, a variety of cells can be loaded, incorporated, cultured on, or cultured in the biocompatible material.

Intervertebral Disc (IVD) and Nucleus Pulposus (NP)

Described herein are compositions and methods for promoting cell attachment and NP-cell phenotype (e.g., progenitor cells, adult NP cells, pathological NP cells, primary adult cells, NP precursor cells) toward expression of nucleus pulposus (NP) cell-specific markers and biosynthesis.

Figure 7:
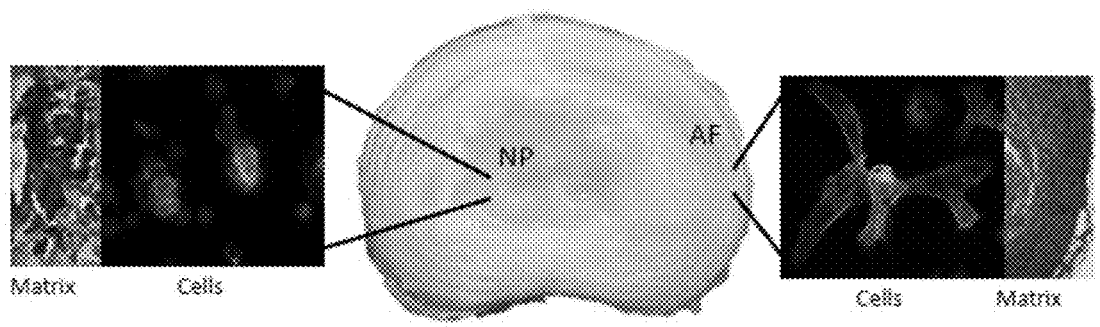
FIG. 7. Schematic of peptide functionalization and hydrogel formation process.

Structures of the intervertebral disc (IVD) function together to provide structural support to the axial skeleton. In the healthy state the nucleus pulposus (NP), located at the center of the IVD, is a highly hydrated (~90% water by wet weight) and soft (<1 KPa) structure which allows it to resist and distribute compressive loading (Choi, 2016; Roughley, 2004; Iatridis, 1996) (see e.g., FIG. 7).

With aging and degeneration however, altered extracellular matrix composition results in loss of hydration and stiffening of the matrix (about 10 kPa-20 kPa in moderately degenerated samples) which in turn leads to impaired function of the structure (Fearing, 2019; Iatridis, 1996; Iatridis, 1997; Clyod, 2007; Walter, 2017). Concomitantly, the cells in the NP, which are derived from the notochord, undergo a shift in phenotype towards a more fibroblastic state, and a reduction in cell density has been observed (Risbud, 2015; Chen, 2009).

The NP is an avascular and aneural tissue, and as such, has a limited intrinsic ability for repair or regeneration (Urban & Roberts 2003). Thus, a body of previous work has been dedicated to the development of biocompatible biomaterials with either bioconductive or bioinductive properties which can be used to serve as a scaffold for cell-delivery (Francisco 2013, Colombini 2014), replace, replicate and/or restore features of the healthy disc (US Patent Pub No. 2008/0071379 to Rydell, U.S. Pat. No. 9,011,545 to Nakamura, Du 2019, Sasson 2012), or can be used to provide particular cues to promote cells towards an NP cell-specific phenotype (Francisco 2014, Bridgen 2017, Zhou 2018). However, the previous studies fail to disclose or suggest the methods disclosed herein.

Prior studies provide strategies to differentiate progenitor cell sources towards the NP cell-specific phenotype using primarily growth factors or soluble mediators, alone or in combination with biomaterial design. Further, prior studies lack strategies based on specific ranges of mechanical stiffness or physical coupling residues that provide physical cues to differentiate progenitor cell sources towards an NP cell-specific phenotype and biosynthesis.

Nucleus Pulposus (NP) Cell-Specific Phenotype

As described herein, the biocompatible compositions as described herein can be used to manipulate cells into cells having a nucleus pulposus (NP) cell-specific phenotype. The NP cell-specific phenotype precursor cells can be an adult NP cell, such as a cell taken from the adult and degenerated intervertebral disc, or a progenitor cell, such as stem cells, induced pluripotent cells, pluripotent cells, precursor cells, or stromal cells.

For the purposes of the present disclosure, the NP cell-specific phenotype and biosynthesis will have been achieved with a rounded cellular morphology (on average circularity values greater than 0.4 or values that are equal to or surpass that seen in cells cultured atop polymerized hydrogels of PEG functionalized with full-length laminin, the "gold standard" for use of laminin-derived peptides), are characterized by fewer paxillin-rich focal adhesions (on average less than 40% of cells, or a value equal to or lesser than that observed by cells cultured atop polymerized hydrogels of PEG functionalized with full-length laminin), and reduced actin fiber coherency (i.e., alignment; on average less than 0.3 or a value equal to or lesser than that observed in cells cultured atop polymerized hydrogels of PEG functionalized with full-length laminin). Additionally, NP cell-specific phenotype will be characterized by gene expression profiles for Col2A1, ACAN, CDH2, and GLUT1, protein expression profiles for BASP1, N-Cadherin, Integrin $\alpha$6, and Cytokeratins (as measured with a pan-cytokeratin antibody), and s-GAG biosynthesis levels that are equal to or surpass that of human NP cells grown atop polymerized hydrogels of PEG functionalized with full-length laminin. Lastly, NP cell-specific phenotype may also be characterized by the vacuole expression of cells which should be greater than that observed in cells cultured on glass or tissue culture plastic.

Stem Cells

As described herein, cells, such as stem cells can be incorporated into the biocompatible composition (e.g., substrate, scaffold). These stem cells can secrete factors for use in in vivo delivery of the composition to the subjects. Examples of stem cells that can be incorporated into the biocompatible composition can be ADSCs, BMSCs, pluripotent stem cells (PSCs), embryonic stem (ES), non-embryonic (adult) stem cells (e.g., hematopoietic stem cells, a type of adult stem cell found in bone marrow; induced pluripotent stem (iPS) cells), cord blood stem cells, or amniotic fluid stem cells, and others.

In some embodiments, the biocompatible composition comprising a peptide-functionalized polymer can serve as a biomaterial for the delivery of stem cells or undifferentiated precursor cells (e.g., induced pluripotent stem cells (iPSCs), mesenchymal stromal cells, mesenchymal stem cells (MSCs), umbilical cord-derived progenitor cells, adipose stem cells, bone marrow stem cells, and other progenitor cells) that can promote cell attachment and also promote the secretion of inflammatory mediating and matrix degrading protease mediating factors including but not limited to: IL-1RA, SIL-6R, STNFRI, STNFRII, and TIMP 1, TIMP 2, TIMP 3, or TIMP 4.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutically active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 20° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, injection into the intervertebral disc space or other space in need thereof. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic, or other physical forces.

Sustained-release preparations may be formulated to extend the activity of the agent(s) and reduce dosage frequency. Controlled-release preparations can also be used to affect the time of onset of action or other characteristics, such as or intra-discal levels or blood levels of the agent, and consequently affect the occurrence of side effects. Sustained-release preparations may be designed to initially release an amount of an agent(s) that produces the desired therapeutic effect, and gradually and continually release other amounts of the agent to maintain the level of therapeutic effect over an extended period of time. The sustained-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating a degenerative disc disease, disorder, or condition in a subject in need of administration of a therapeutically effective amount of an NP-like biocompatible composition (e.g., a cell-free biocompatible composition or a biocompatible composition comprising autologous or allogeneic primary NP cells, precursors to NP cells, or pathological human NP cells).

Methods described herein are generally performed on a subject in need thereof. A subject in need of the therapeutic methods described herein can be a subject having, diagnosed with, suspected of having, or at risk for developing a degenerative disc disease, disorder, or condition (e.g., a defect in an intervertebral disc, disc herniation, stenosis, or degeneration). A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans. For example, the subject can be a human subject.

Generally, a safe and effective amount of an NP-like biocompatible composition is, for example, that amount that would cause the desired therapeutic effect in a subject while minimizing undesired side effects. In various embodiments, an effective amount of an NP-like biocompatible composition described herein can substantially inhibit a degenerative disc disease, disorder, or condition; reduce the symptoms of a degenerative disc disease, disorder, or condition; slow the progress of a degenerative disc disease, disorder, or condition; or limit the development of a degenerative disc disease, disorder, or condition.

According to the methods described herein, administration can be via direct injection into the intervertebral disc space or intra-discal injection.

When used in the treatments described herein, a therapeutically effective amount of an NP-like biocompatible composition can be employed in pure form or, where such forms exist, in pharmaceutically acceptable form, with or without a pharmaceutically acceptable excipient, or the polymeric composition and crosslinking agents can be administered separately to achieve gelation in situ. For example, the compounds or components of the present disclosure can be administered, at a reasonable benefit/risk ratio applicable to any medical treatment, in a sufficient amount to substantially inhibit a degenerative disc disease, disorder, or condition, slow the progress of a degenerative disc disease, disorder, or condition, or limit the development of a degenerative disc disease, disorder, or condition.

The amount of a biocompatible composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state and/or unwanted symptoms of the disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or a physician. The biocompatible compositions described herein can be disease-modifying, which can be measured by anatomic changes that can be difficult to detect in human subjects, but there can also be a therapeutic effect on symptoms of pain and motion.

Administration of an NP-like biocompatible composition can occur as a single event or over a time course of treatment. For example, an NP-like biocompatible composition can be administered at a frequency more than once per month (e.g., monthly, semi-annually, annually, or biannually).

Treatment in accord with the methods described herein can be performed prior to, concurrent with, or after conventional treatment modalities for a degenerative disc disease, disorder, or condition.

An NP-like biocompatible composition can be administered simultaneously or sequentially with another agent, such as an antibiotic, an anti-inflammatory, or another agent. For example, an NP-like biocompatible composition can be administered simultaneously with another agent, such as an antibiotic or an anti-inflammatory. Simultaneous administration can occur through administration of separate compositions, each containing one or more of an NP-like biocompatible composition, an antibiotic, an anti-inflammatory, or another agent. Simultaneous administration can occur through administration of one composition containing two or more of an NP-like biocompatible composition, an antibiotic, an anti-inflammatory, or another agent. An NP-like biocompatible composition can be administered sequentially with an antibiotic, an anti-inflammatory, or another agent. For example, an NP-like biocompatible composition can be administered before or after administration of an antibiotic, an anti-inflammatory, or another agent.

Administration

Agents and compositions described herein can be administered according to methods described herein in a variety of means known to the art. The agents, components, or biological compositions can be used therapeutically either as exogenous agents or as endogenous agents. Exogenous agents are those produced or manufactured outside of the body and administered to the body. Endogenous agents are those produced or manufactured inside the body (e.g., by a device or implant).

Administration of the biocompatible compositions can be via an intra-discal injection delivered either percutaneous with or without image guidance, and/or intra-discal injection delivered during a catheter-based surgical procedure or interventional procedure in the spine.

Administration of an exogenous agent can be intra-discal, intervertebral, parenteral, pulmonary, oral, topical, intradermal, intramuscular, intraperitoneal, intravenous, subcutaneous, intranasal, epidural, ophthalmic, buccal, or rectal administration.

Any route of administration of the biocompatible composition known in the art can be used. Implantation and injection of biomaterials into the IVD space or intra-discal space are well known; see e.g., Smith 2018 *JOR Spine* 1 (4) e1036; Frauchiger 2017 *Eur Cells Mat* 34 271-290; Bowles 2017 *Biomaterials* 129:54-67. Except as otherwise noted herein, therefore, the process of the present disclosure can be carried out in accordance with such processes.

Agents and compositions described herein can be administered in a variety of methods well known in the arts. Administration can include, for example, methods involving direct injection (e.g., systemic or stereotactic), implantation of cells, biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of sustained-release delivery of agents or compositions will be known to the skilled artisan and are within the scope of the present disclosure.

Delivery systems may include, for example, a syringe or an infusion pump which may be used to administer the agent or composition in a manner similar to that used for delivering insulin or chemotherapy to specific tissues or areas. Typically, using such a system, an agent or composition can be administered in combination with a biodegradable, biocompatible polymeric implant that releases the agent over a controlled period of time at a selected site. The biocompatible compositions as described herein can comprise any polymer suitable for a hydrogel and/or the hydrogel can also be delivered with therapeutic agents, thus requiring only a fraction of a systemic dosage.

Biocompatible compositions and agents (e.g., the hydrogel implants or components thereof) can be a drug delivery system or can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10:0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers. The precursor solutions can be mixed in advance of delivery through a single syringe and needle, or applied to a dual barrel syringe and applied as a single injection directly into the disc in order to achieve in situ crosslinking and gel formation in a timeframe ranging from on average several seconds to greater than 10 minutes (gelation time being controlled by several factors including the pH of the solution). Components include, but are not limited to monomers, polymers, buffers, cell media, adult cells, stem cells, progenitor cells, or laminin-mimetic peptides (e.g., integrin-binding peptides, syndecan-binding peptides). Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, or sterile saline each of which has been packaged under a neutral non-reacting gas, such as nitrogen. Ampules may consist of any suitable material, such as glass, organic polymers, such as polycarbonate, polystyrene, ceramic, metal, or any other material typically employed to hold reagents. Other examples of suitable containers include bottles that may be fabricated from similar substances as ampules and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronicreadable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10:0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41 (1), 207-234; Gellissen, ed. (2005) Production of Recombinant Proteins: Novel Microbial and Eukaryotic Expression Systems, Wiley-VCH, ISBN-10:3527310363; Baneyx (2004) Protein Expression Technologies, Taylor & Francis, ISBN-10:0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Polymer-Peptide Conjugate Supporting Human Nucleus Pulposus Cell Attachment The following example describes the biocompatible composition's mechanical properties and ability to support attachment of human primary nucleus pulposus (NP) cells.

Methods

Formulation of Hydrogels

Maleimide terminated 8-arm poly(ethylene glycol) (8-arm PEG-MAL) monomers were pre-conjugated with cell adhesive peptides (e.g. integrin binding IKVAV and syndecan binding AG73) at pH 3.25. Following the pre-conjugation step, 8-arm PEG-MAL was crosslinked using PEG dithiol (SH-PEG-SH) in a Michael type addition reaction to form a peptide presenting hydrogel. Variations in stoichiometry (ratio of MAL:SH) and percentage of total PEG (w/v) allowed for control of hydrogel stiffness and reactive group availability. Experimental conditions included formulations that yielded soft (~0.5 kPa) and stiff (~10 kPa) hydrogels, as well as variable peptide densities (50, 100, 200, and 400 µM). The hydrogels were allowed to swell in phosphate buffered saline (PBS) for on average 10-24 hours before use in further experimentation.

Characterization of Composition, Mechanical Properties, and Chemical Coupling

Hydrogels were formulated as described herein before being cut into discs 8 mm in diameter and approximately 2 mm thick. Discs were subjected to oscillatory shear using an AR-G2 Rheometer (TA instruments). Samples were pre-heated to 37° C. and underwent a pre-loading step of 0.015 N after which 10% compressive strain was applied. Then samples were allowed a 2-minute conditioning step for relaxation before undergoing oscillatory torsional strains (1-10 rad/s with constant shear strain of 0.01) and complex shear modulus was reported for all samples at an angular frequency of 10 rad/s.

Efficiency of cross-linking was determined by adding 775 µM SH-PEG-FITC (MW 10K) to an 8-arm PEG-MAL and allowed to react for 1 hour at room temperature in 1×PBS (pH 7.4). The conjugated solution was then filtered through a 10K spin column four times to remove unconjugated reactants. The fluorescence of the hydrogel was measured (excitation 488 nm, emission 525 nm) using a plate reader in order to calculate the concentration of conjugated PEG-8MAL-FITC.

Cell Attachment and Morphology

Adult primary nucleus pulposus cells were cultured atop the hydrogel formations described at a density of 25,000-30,000 cells/cm$^2$ for 24 hours at 37° C.+5% $CO_2$. To quantify cell attachment, cells were lysed, and percent cell adhesion was determined using the Cell-Titer GLO® (Promega, Madison, WI) plate reader assay following manufacturer protocols in a PerkinElmer EnSpire Multimode plate reader (Waltham, MA).

Results

Characterization of Composition Mechanical Properties and Chemical Coupling

FIG. 1 shows results for mechanical testing of the compositions made with on average 4% or on average 15% PEG, as well as functionalization efficiency.

Cell Attachment and Morphology

Figures 2A, 2B, 2C:
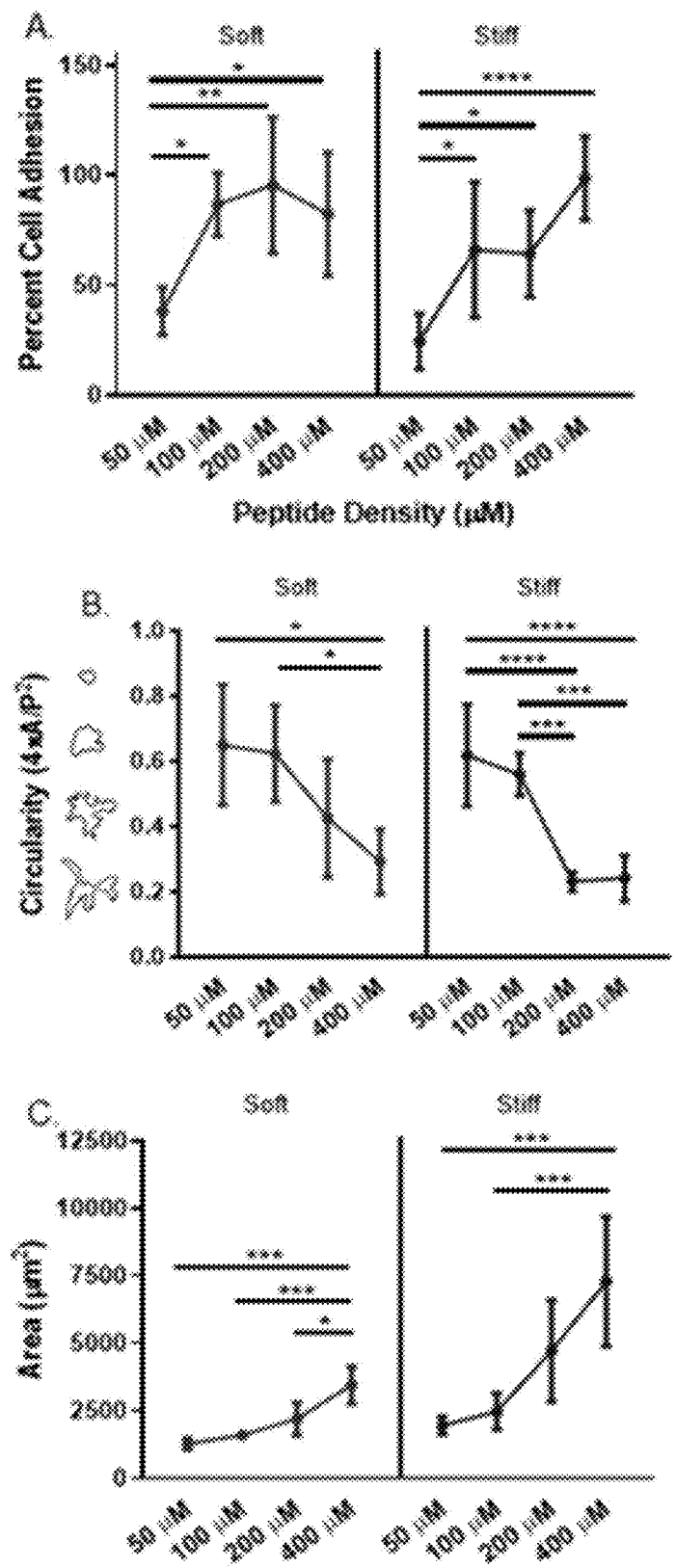
FIG. 2A-FIG. 2F. Morphological data presented as mean+/−standard deviation for cell adhesion, circularity, area, and actin coherency (A, B, C, D, F), and (E) shows representative images of F-actin staining for cells cultured on various substrates (top) and color survey of fiber orientation (bottom). A) Increasing peptide density leads to increased cell adhesion. B-C) Increases in cell spreading and paralleled decreases in cell circularity for both soft and stiff hydrogels. (D-E) Stiff 400 UM substrates lead to increased actin fiber alignment, while soft substrates and stiff 100 μM substrates lead to more cortical actin. Dashed lines show values of cells upon tissue culture polystyrene (TCPS) (gray) and 4% PEG-laminin (PEG-LM, green) for reference. For immunostaining, green is actin, blue is nuclei, scale bar is 20 μm. Bottom row shows color map of actin alignment. F) Stiff 100 μM substrates demonstrate no significant differences in cell spreading and circularity versus soft gels at 100, 200, or 400 μM. * $p<0.05$,  $p<0.01$, * $p<0.001$, **** $p<0.0001$, using one-way ANOVA with Tukey's multiple comparison's test (A, B, C, D), or Dunnett's multiple comparison's test (F).
Figures 2D, 2E:
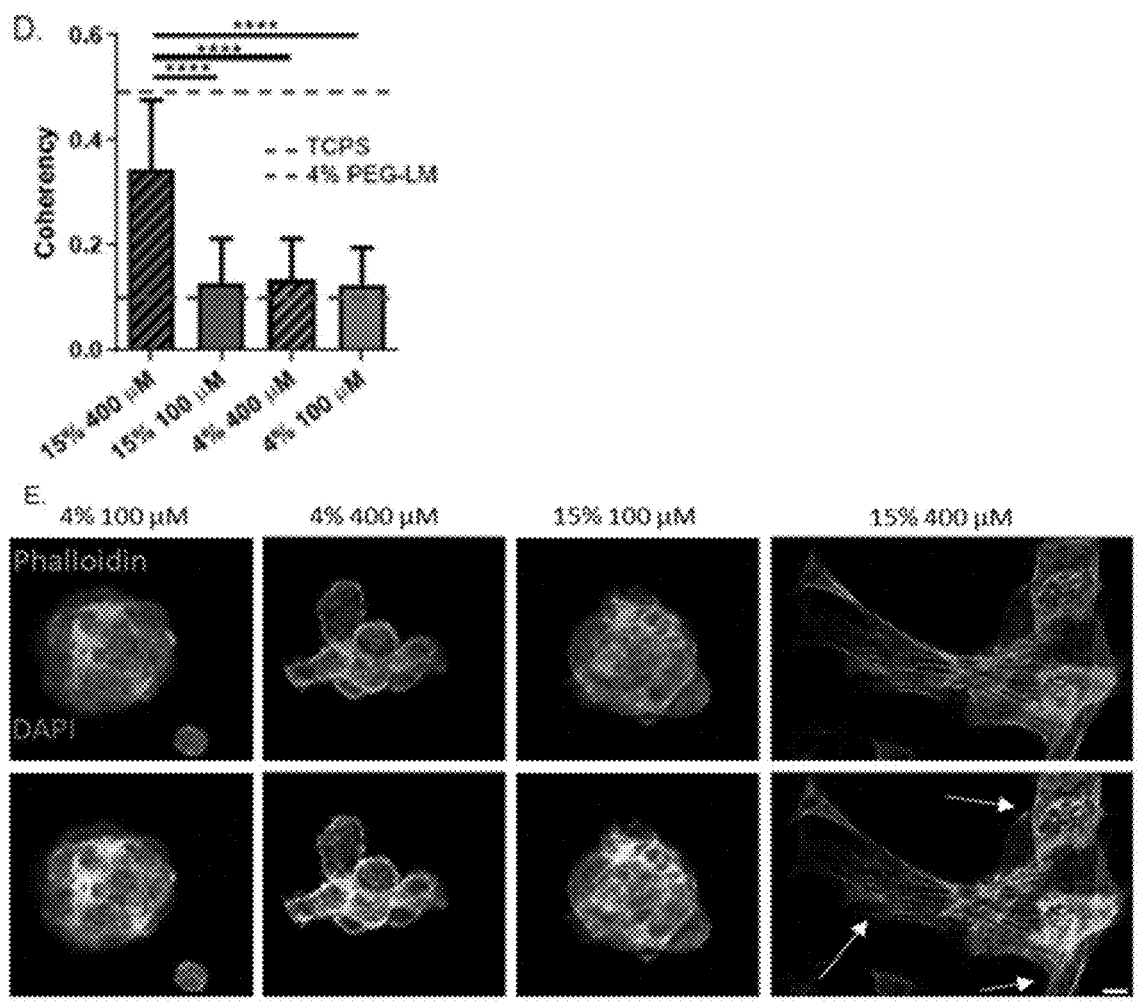

FIG. 2A shows that peptide (ligand) density controls cell attachment behaviors in both soft (red) and stiff (blue) hydrogel systems. Significant differences in cell attachment can be observed between 50 µM peptide density and all densities>100 UM (see e.g., FIG. 2A). FIG. 2 further shows that stiff hydrogels with low peptide density may mimic soft hydrogel systems. Importantly, this shows that we can make stiff hydrogels look like soft hydrogels biologically, by controlling peptide density.

Sequence Listing

| | |
|---|---|
| AG73: RKRLQVQLSIRT | (SEQ ID NO: 1) |
| IKVAV: RARKQAASIKVAVSADR | (SEQ ID NO: 2) |
| P4: PPFLMLLKGSTR | (SEQ ID NO: 3) |
| YIGSR: EGYGEGYIGSR | (SEQ ID NO: 4) |
| A5G81: AGQWHRVSRWG | (SEQ ID NO: 5) |
| GD6: KQNCLSSRASFRGCVRNLRLSR | (SEQ ID NO: 6) |

Example 2: Regulating the Phenotype of Nucleus Pulposus Cells by Laminin-Mimetic Peptide-Coupled Substrates The following example describes the use of a polymer-peptide hydrogel scaffold with tunable stiffness and adhesive group presentation using laminin-mimetic peptides. The polymer-peptide hydrogels were evaluated to identify an optimal formulation that will modulate NP cell adhesion and phenotype to mimic that of the healthy NP cell.

Introduction

Intervertebral disc (IVD) aging is associated with changes in extracellular matrix (ECM) biochemistry and cellular phenotype that contribute to pathologies of disc herniation, stenosis, and degeneration. Specifically, nucleus pulposus (NP) cells that originate from the embryonic notochord undergo a differentiation to a fibroblast-like state with aging. In juvenile NP, cells reside in soft laminin-rich extracellular matrix (ECM). However, with aging and degeneration, there is a significant decrease in the expression of the multiple different laminin isoforms, which is believed to be correlated with the phenotypic change of the NP cells. We have previously shown that soft polyacrylamide substrates (~0.3 kPa) conjugated with full length laminin (LM-111) protein promote expression of healthy NP molecular markers. However, the presence of the multiple different laminin isoforms and their bioinductive differences leads to difficulties in fine-tuning and eliciting controlled cellular responses.

Methods

Morphological Assessment

As previously discussed in Example 1, maleimide terminated 8-arm poly(ethylene glycol) (8-arm PEG-MAL) monomers were pre-conjugated with cell adhesive peptides (e.g., integrin binding IKVAV and syndecan binding AG73) at pH 3.25. Following the pre-conjugation step, 8-arm PEG-MAL was crosslinked using PEG dithiol (SH-PEG-SH) to form a peptide presenting hydrogel. Experimental conditions included soft (~0.5 kPa) and stiff (~10 kPa) substrates, as well as variable peptide densities (50, 100, 200, and 400 µM). NP cells (human NP from to-be-discarded surgical waste) were seeded atop the hydrogels at a density of 25,000-30,000 cells/cm$^2$ and cultured at 37° C.+5% $CO_2$. For 3D culture conditions, cells were trypsinized, pelleted, and resuspended directly in PEG-dithiol monomer solution (PEG-dithiol in 1×PBS pH 7.4). PicoGreen and DMMB assays were used to quantify DNA and glycosaminoglycan production respectively. Cells were immunostained and imaged to quantify cell body circularity and spread area, as well as a number of nuclei per cytoskeletal structure (Cell-Profiler™). Evidence of differences in these parameters amongst substrates of different stiffness and peptide concentrations was tested using a one-way ANOVA with Tukey's multiple comparisons test ($\alpha<0.05$) (GraphPad Prism).

Phenotypic Expression (Gene and Protein)

Gene expression was assayed using qPCR on an Applied Biosystems™ StepOnePlus™ Real-Time PCR System (Software v2.3, Foster City, CA). Briefly, primary adult human NP cells were seeded on the appropriate gels at a density of 100,000-150,000 cells/cm$^2$ and cultured for 4 days at 37° C. and 5% $CO_2$. Following the incubation period, the cells were lysed using RLT buffer (Qiagen, Hilden, Germany)+1% mercaptoethanol. RNA isolation was done using the QIAGEN™ Mini kit (Qiagen) following manufacturer instructions. RNA concentration and purity were determined using the 260/280 ratio in a NanoDrop™ system (ThermoFisher Scientific, Waltham, MA). RNA was then converted to cDNA using the iScript cDNA Synthesis Kit (BioRad, Hercules, CA). qPCR was used to detect amplification of aggrecan (ACAN), collagen 2 (COL2A1), N-Cadherin (CDH2), and glucose transporter 1 (GLUT1) using the $\Delta\Delta C_t$ method, with the first $\Delta$ being normalization of the gene to housekeeping genes 18S and GAPDH, and the second $\Delta$ being normalization to a control substrate, in this case tissue culture polystyrene (TCPS, FIG. 4) or soft PEG laminin hydrogels (see e.g., FIG. 5).

For the quantification of protein expression adult primary nucleus pulposus cells were cultured atop the hydrogel formations described at a density of 25,000-30,000 cells/cm$^2$ for 24 hours at 37° C.+5% $CO_2$. Cells were then fixed in 4% paraformaldehyde and stained with antibodies targeting the proteins BASP1, Cytokeratins (using a pan-cytokeratin antibody), N-Cadherin, and Integrin α6; nuclei were counterstained using DAPI. The samples were then imaged via confocal fluorescence microscopy. Expression of the proteins were quantified using ImageJ software (National Institutes of Health, Bethesda, MD).

Focal Adhesion and Contractility

Adult primary nucleus pulposus cells were cultured atop the hydrogel formations described at a density of 25,000-30,000 cells/cm$^2$ for 24 hours at 37° C.+5% $CO_2$. Cells were then fixed in 4% paraformaldehyde and stained with Phalloidin to label F-actin structures, DAPI to label nuclei, and either a rabbit-anti-phospho myosin light chain 2 (pMLC) or rabbit-anti-paxillin. Percent cells immunopositive for pMLC as a measure of cell contractility, number of paxillin puncta, and overall paxillin area were quantified using ImageJ software.

Vacuole Expression

Adult primary nucleus pulposus cells were cultured atop the hydrogel formulations described. Monodansylcadaverine (MDC) was used as a plate reader assay to quantify fluorescence associated with transient formation of vacuoles. Brightfield imaging was applied in parallel to visualize these structures.

Quantification of Biosynthesis sGAG production was assayed using 1,9-dimethyl-methylene blue zinc chloride (DMMB, Sigma-Aldrich). Briefly, primary human NP cells were seeded on gels made in wells of a 96 well plate and cultured for 4 days at 37° C. and 5% $CO_2$. The entire cell-gel construct was then digested in papain buffer (5 mM EDTA, 5 mM L-Cysteine, 125 µg/mL papain in PBS) overnight at 60° C. sGAG concentration in the digested constructs+supernatant media was determined against chondroitin sulfate (Sigma-Aldrich) standards and normalized to DNA content obtained using the Quant-iT™ PicoGreen® dsDNA kit (Invitrogen) following manufacturer recommendations. Hydrogel constructs without cells were used as negative controls to correct for any colorimetric interference introduced by the gels.

Results

Morphological Assessments

Figure 2F:
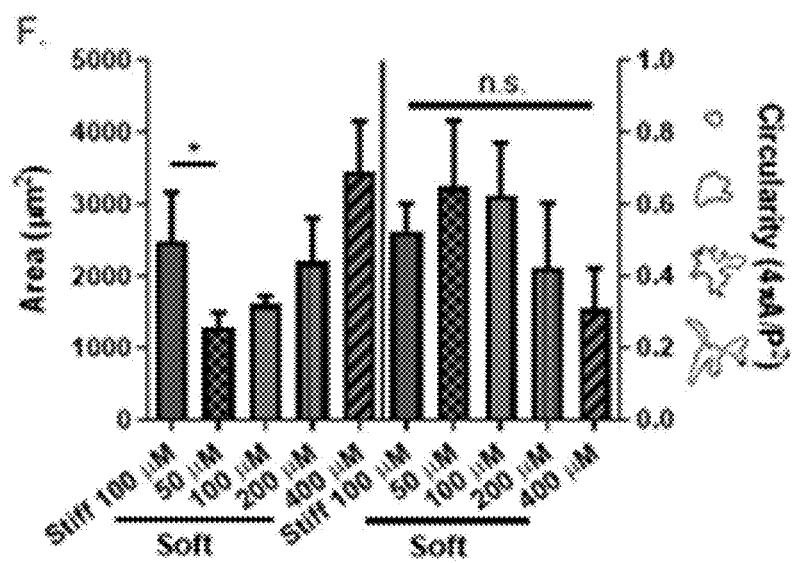
Figures 3A, 3B, 3C, 3D:
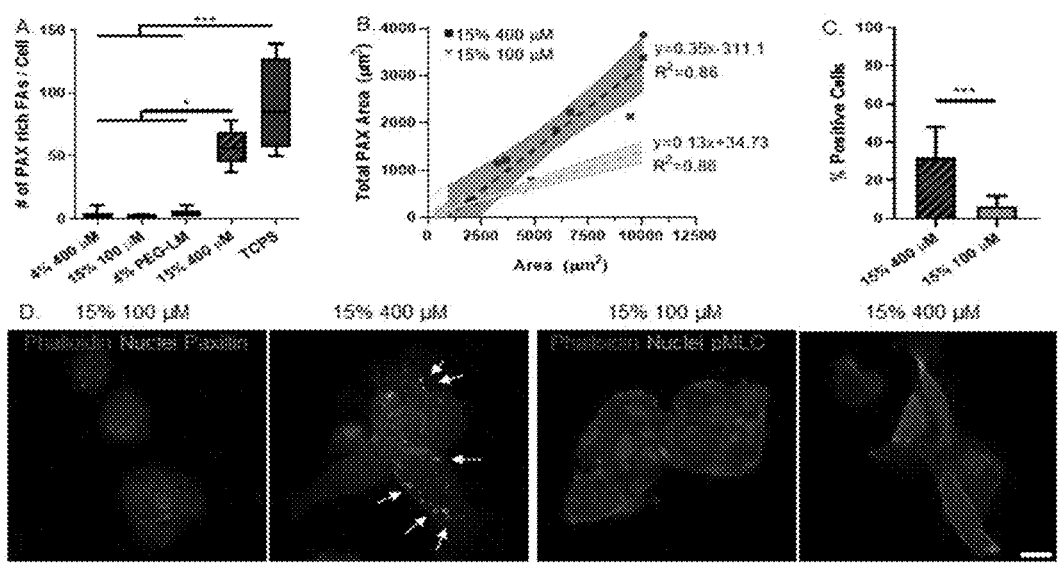
FIG. 3A-FIG. 3D. Quantification of paxillin staining quantified as # of paxillin rich focal adhesions per cell (A), total paxillin area plotted against cell area (B), % cells positive for paxillin (C), and representative images (D). Where appropriate, values were plotted as mean+/−standard deviation. A) Quantification of paxillin rich focal adhesions per condition. B) Linear regression for stiff 100 μM and 400 μM substrates suggests correlation between cell spreading and paxillin presence. C) Immunopositivity of phospho Myosin Light Chain (pMLC) in primary adult human NP cells. D) Representative immunostaining of paxillin and pMLC. * $p<0.05$, *** $p<0.001$, using one-way ANOVA with Tukey's multiple comparison's test (A), or t-test (C). Scale bar is 20 μm.

An increase in cell spreading can be observed as peptide density increases in both soft and stiff substrates (see e.g., FIG. 2C, FIG. 2F). These values are accompanied by a decrease in cell circularity (see e.g., FIG. 2B, FIG. 2F, FIG. 2E) and a shift towards a more contractile phenotype as demonstrated by the formation of more paxillin-rich focal adhesions (number and area of focal adhesions) that are more pMLC positive (see e.g., FIG. 3). At lower peptide densities, cells form more rounded clusters with a lesser degree of spreading regardless of substrate stiffness (see e.g., FIGS. 2B, 2C, 2E, and 2F). Additionally, the cells cultured on stiff gels with low peptide density or soft gels with high or low density exhibited less F-actin fiber alignment (see e.g., FIGS. 2D and 2E).

Phenotypic Expression (Gene and Protein)

Figure 4A:
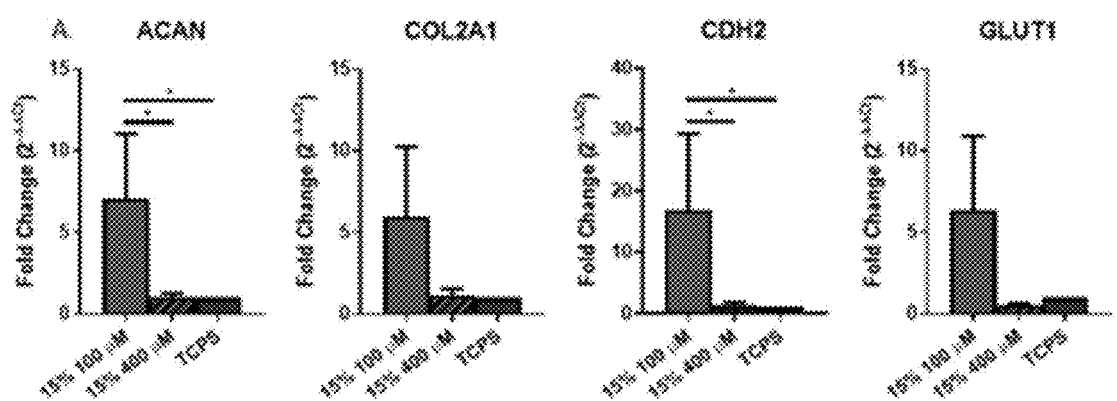
FIG. 4A-FIG. 4C. Phenotypic assessment (gene and protein expression) of cells cultured on stiff hydrogels. A) qPCR for a panel of genes associated with the NP-cell specific phenotype. B-C) Quantification of protein expression and representative images of a panel of proteins associated with the cell-specific NP phenotype. * $p<0.05$,  $p<0.01$, * $p<0.001$, **** $p<0.0001$. One-way ANOVA with Tukey's multiple comparison's test (A, B). Scale bar is 50 μm.
Figure 4B:
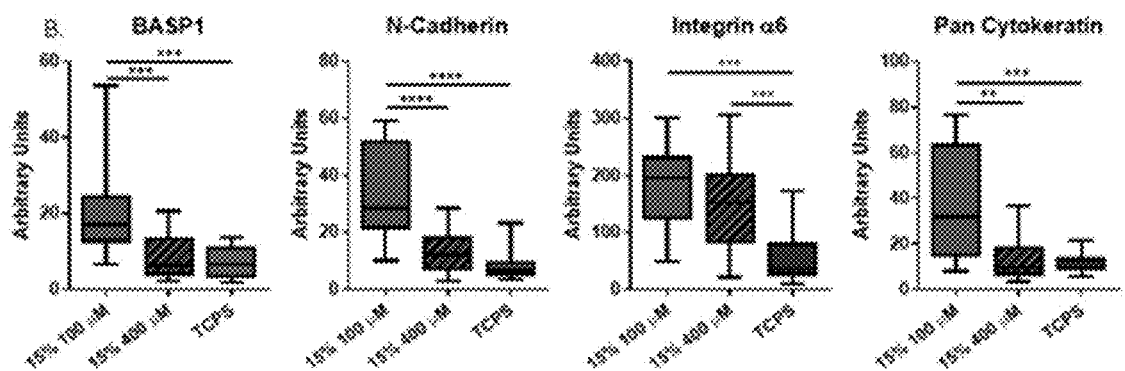
Figure 4C:
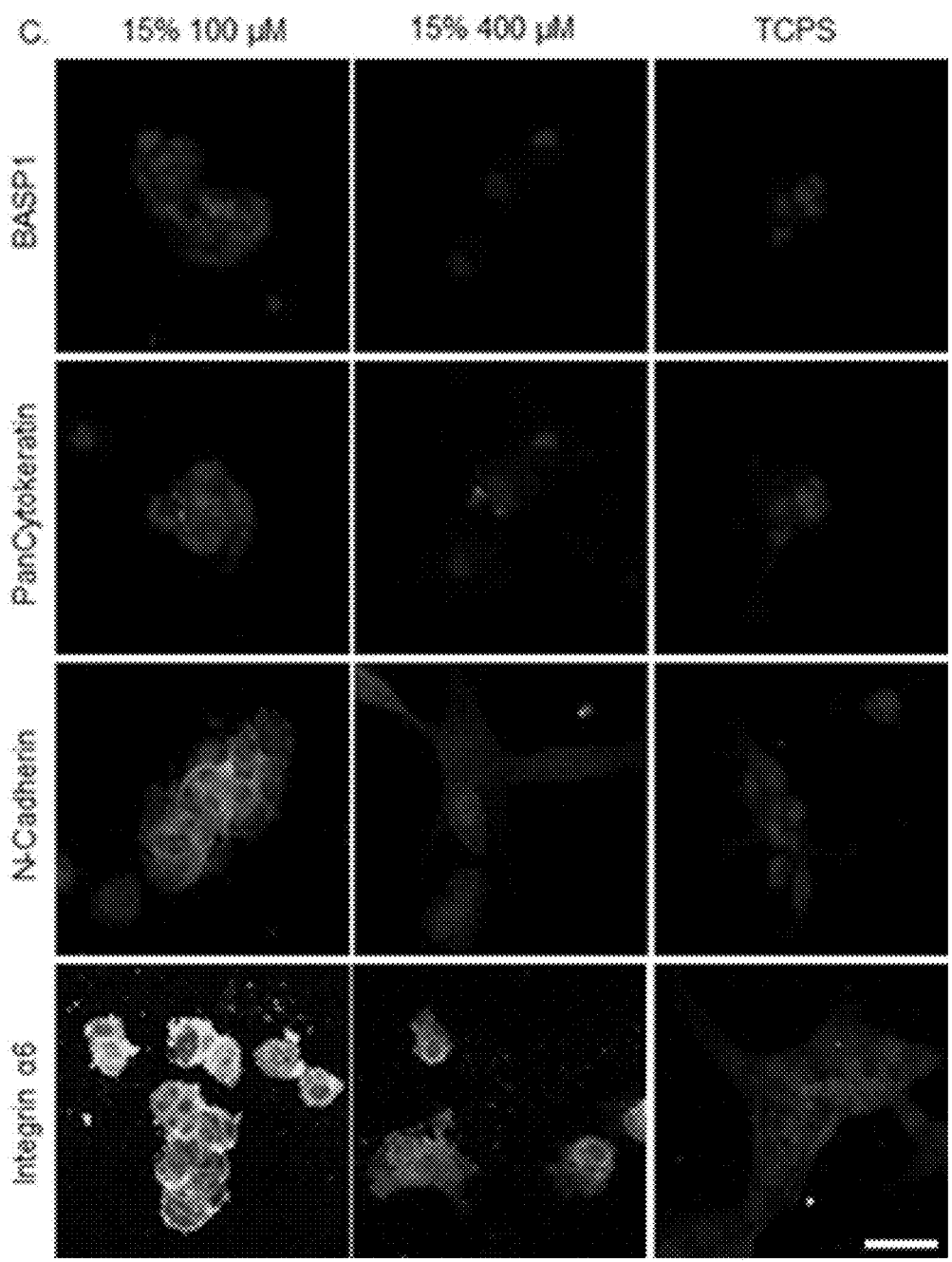
Figures 5A, 5B:
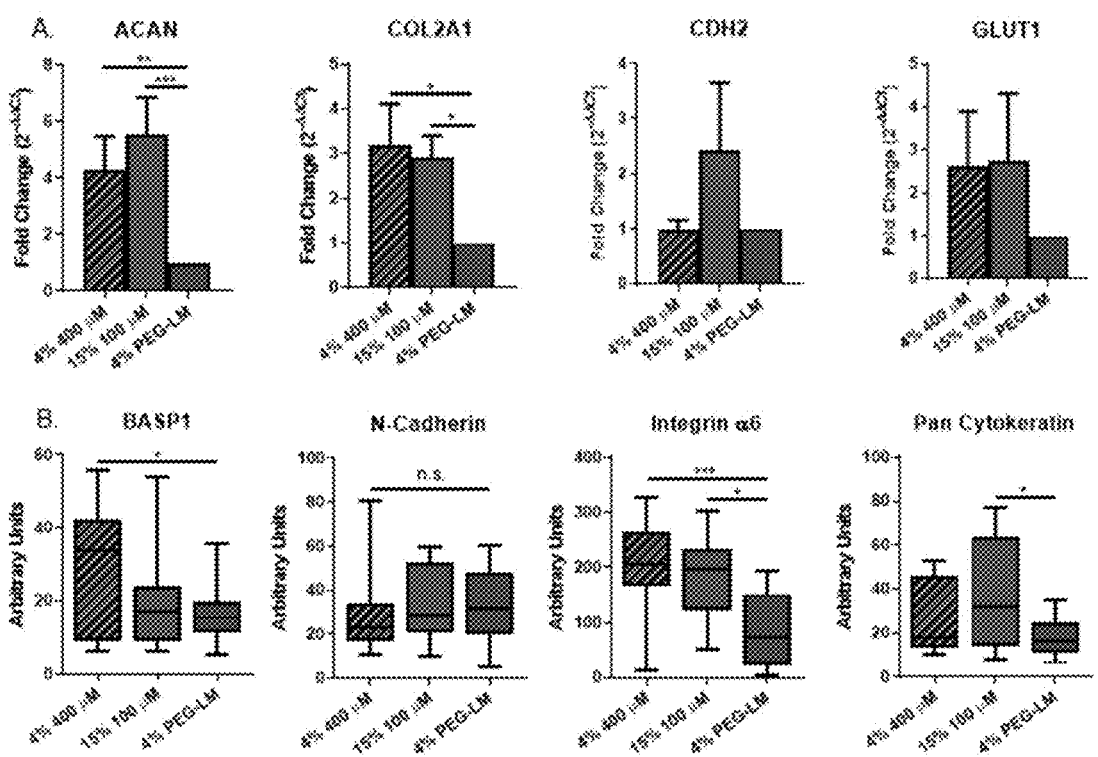
FIG. 5A-FIG. 5D. Phenotypic assessment (gene and protein expression) of cells cultured on soft and stiff substrates. A) qPCR for a panel of genes associated with the cell-specific NP phenotype. B-C) Quantification of protein expression and representative images of a panel of proteins associated with juvenile NP cells. D) Deposition of sulfated glycosaminoglycans (sGAGs) and cell viability upon culture on different substrates. * $p<0.05$,  $p<0.01$, * $p<0.001$, using one-way ANOVA with Tukey's multiple comparison's test (A, B, D). Scale bar is 50 μm.
Figure 5C:
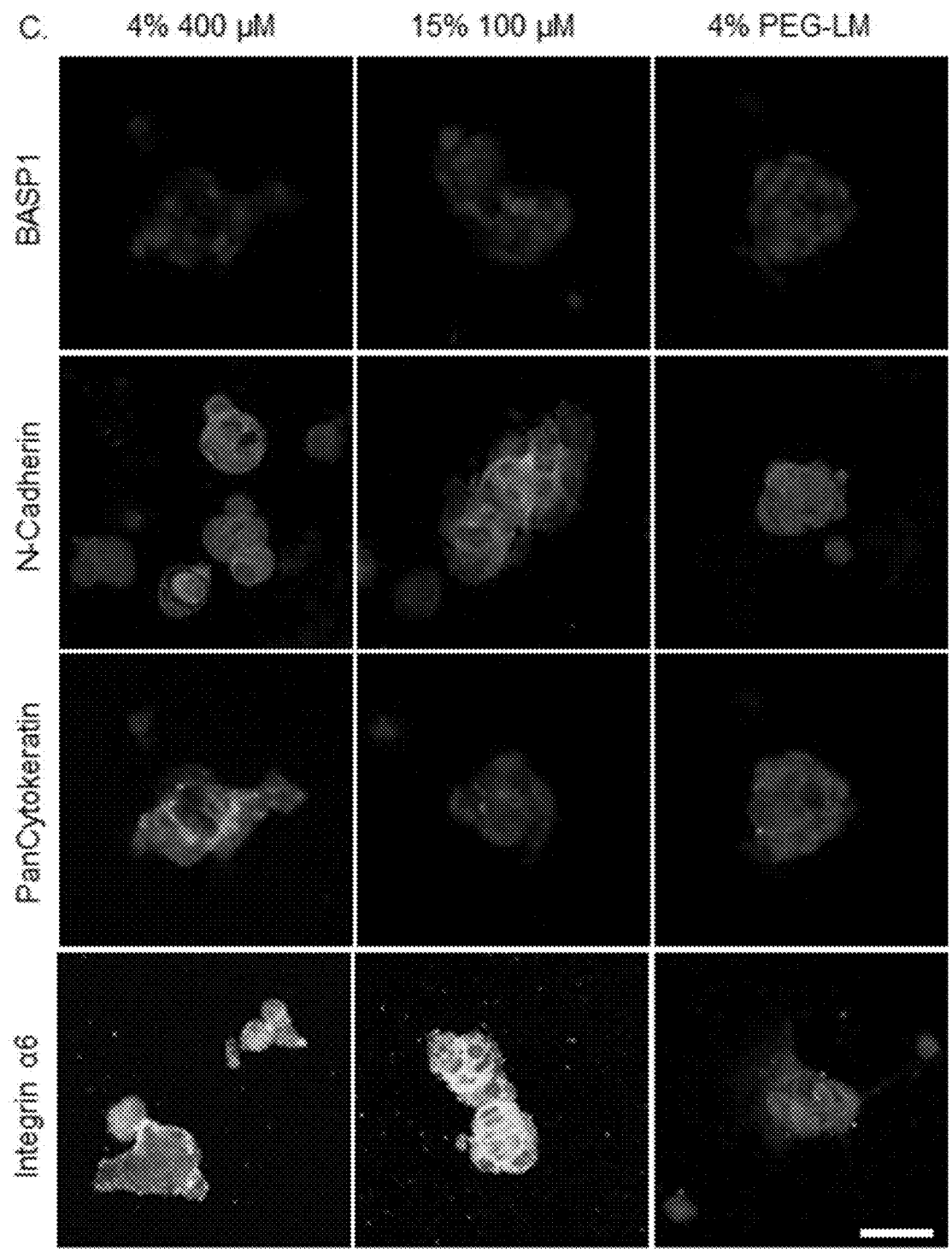

FIG. 4 demonstrates that stiff 100 µM substrates promote NP cell-specific phenotype than similar stiffness hydrogels at higher peptide densities. Cells cultured on the stiff 100 µM condition exhibited increased gene expression of NP cell-specific genes (ACAN, COL2A1, CDH2, and GLUT1) compared to either similarly stiff hydrogels or to tissue culture plastic (TCPS) (see e.g., FIG. 4A). This effect was also confirmed at the protein level where cells cultured on stiff 100 µM substrates exhibited increased protein expression for BASP1, N-Cadherin, Integrin α6, and Cytokeratins (see e.g., FIGS. 4B and 4C). Additionally, FIG. 5 confirms that stiff 100 µM substrates promote an NP cell-specific phenotype similar to that observed in soft hydrogel systems and the soft PEG-laminin "gold standard". This can be observed by similar gene expression profiles between stiff low peptide, soft high peptide, and soft PEG-LM (see e.g., FIG. 5A), and by similar levels of protein expression or higher protein expression in stiff low peptide than in the soft PEG-LM gold standard (see e.g., FIG. 5B, FIG. 5C).

Biosynthesis and Cell Viability

Figure 5D:
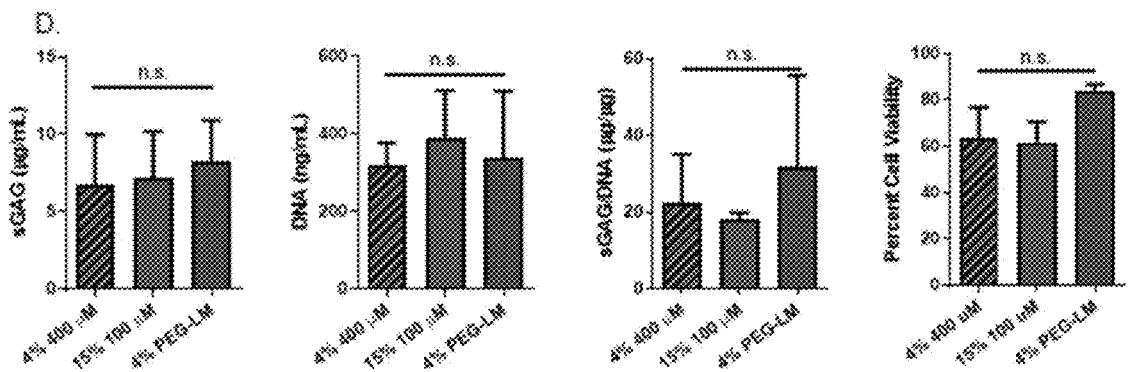

FIG. 5D further demonstrates that the stiff low peptide gels promote similar degrees of biosynthesis (sGAG deposition) as the soft high peptide and the soft PEG-LM conditions. Additionally, cell viability was not decreased on the stiff low peptide gel compared to either of the soft conditions (soft PEG-LM or soft high peptide).

Vacuole Expression

Figures 6A, 6B:
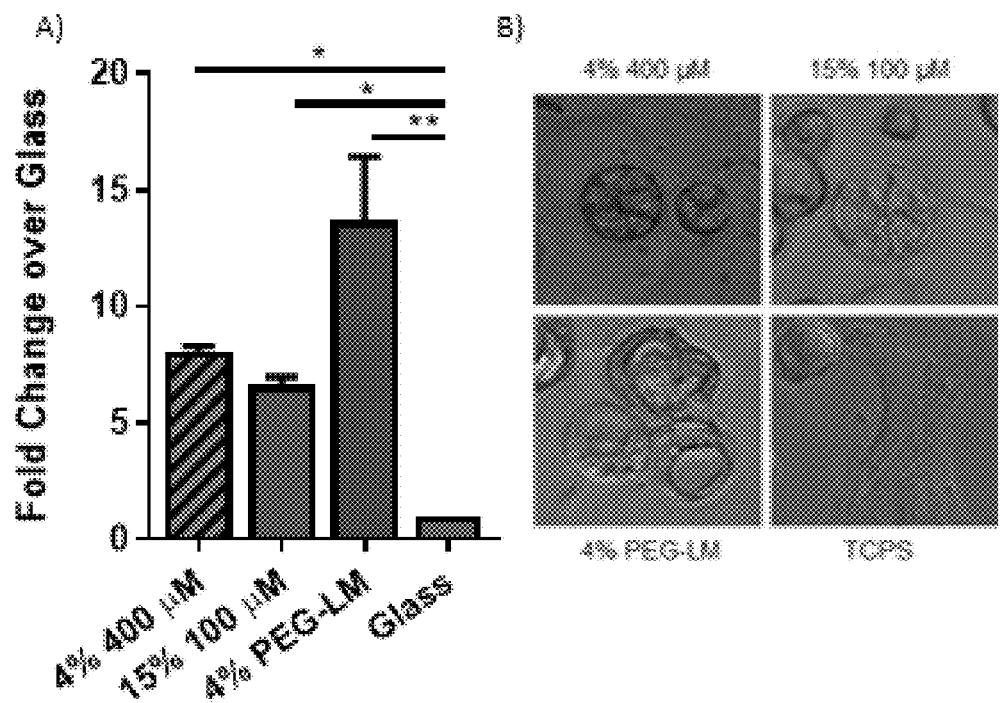
FIG. 6A-FIG. 6B. Quantification of vacuoles and photographic images of cells cultured on hydrogels. A) All substrates promoted significantly increased vacuole formation versus cells cultured on tissue culture glass, as quantified via monodansylcadaverine (MDC) staining. B) Brightfield images of vacuole formation. * $p<0.05$, ** $p<0.01$, using one-way ANOVA with Dunnett's multiple comparisons test.

FIG. 6 shows evidence of vacuole re-expression upon culture on stiff low peptide density and on soft substrates consistent with the expected expression seen in juvenile NP cells.

Discussion

These results provide evidence of the ability to control cell morphology and phenotype by variations in substrate stiffness and peptide (ligand) density using peptide-hydrogel systems. Furthermore, this system provides an ability to promote cellular morphologies/phenotypes consistent with those seen in native juvenile NP tissue (see e.g., FIG. 7) and in cells cultured on the previous "gold standard" PEG-LM.

Clinical Relevance

Peptide-polymer hydrogels can allow for bioinductive materials that promote re-expression of the healthy NP cell morphology and phenotype. A materials-based approach at restoring both the mechanical properties of the disc as well as cellular bioactivity may provide a new approach for treating degenerative disc disease.

Example 3: Engineering Laminin-Mimetic Peptide Systems for Np Cell Culture in 3D This example describes the use of peptide-functionalized hydrogel substrates capable of supporting 3D cell culture of NP cells and promoting the expression of an NP cell-specific phenotype.

Methods 8-arm maleimide-terminated poly(ethylene glycol) (PEG-8MAL) were pre-conjugated with cysteine terminated peptides (100 μM-400 μM total peptide) and crosslinked with PEG-dithiol (SH-PEG-SH as previously described with the following modifications for 3D culture: lyophilized peptides were dissolved in the appropriate volume of cell culture media and added to the PEG-MAL solution in order to couple peptides to the PEG-backbone. Following, human NP cells were trypsinized, spun down for ~10 minutes at ~400 rcf to form a pellet, and then resuspended in cell culture media (volume variable depending on cell counts; volume used should lead to a final in-gel cell concentration of 5-10 million cells/mL). The cell-containing pre-cursor was then mixed with the PEG-MAL-peptide solution directly in the wells of a 96 well plate to form a 3D cell-laden hydrogel. Suspension of all precursor solutions in neutral buffered cell culture media (~pH 7.1) allows for rapid hydrogel formation (on average <10 seconds) and cell encapsulation. Cells in contact with 2D or 3D hydrogels were incubated for 96 hours prior to qPCR analysis or Live-Dead staining.

Results

Figures 8A, 8B, 8C:
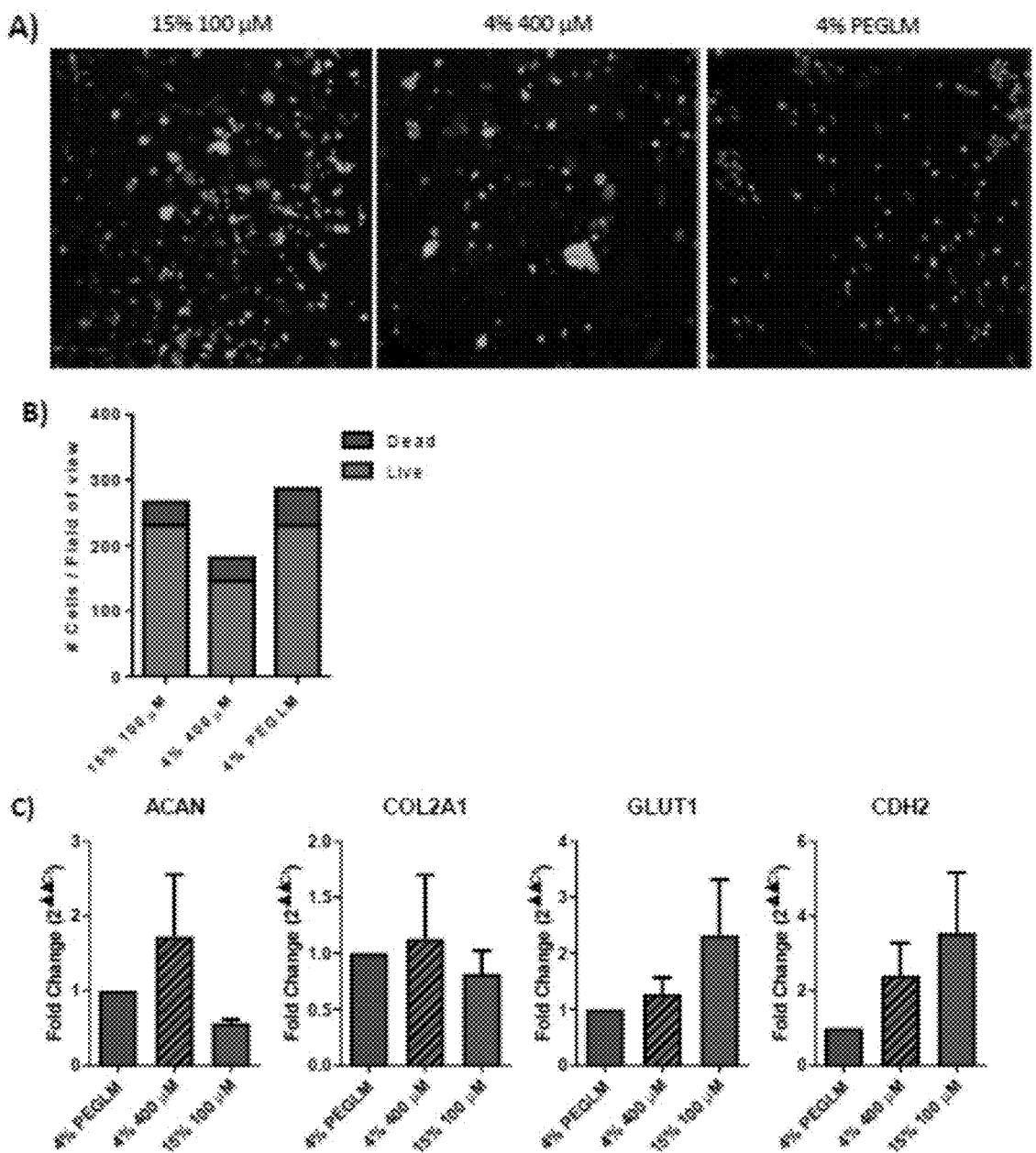
FIG. 8A-FIG. 8C. Peptide functionalized substrates support 3D viability and bioactivity. Live dead staining and respective quantifications seen in (A) and (B). C) mRNA levels following 3D culture within the three different hydrogels, quantified via the $\Delta\Delta C_t$ method using RT-qPCR. Green is live cells, red is dead.
Figure 9:
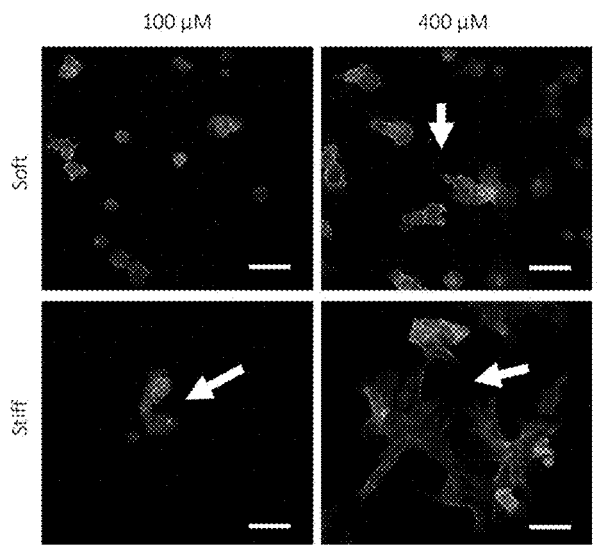
FIG. 9. A. Representative immunostaining images of NP cells cultured for 24 hours on substrates of variable stiffness and peptide density. Green is actin, blue is nuclei. Scale bar is 50 μm. B. Increasing peptide density leads to increased cluster formation, but has no effect on cell adhesion above 50 μM total peptide. C-D. Stiff low peptide systems have similar degrees of spreading and circularity as soft high peptide gels, as well as decreased actin alignment to levels similar to that of soft PEG-LM. E. Systems functionalized with different integrin binding peptides elicit similar degrees of cell spreading but different degrees of circularity (one-way ANOVA, $p<0.05$).
Figure 9:
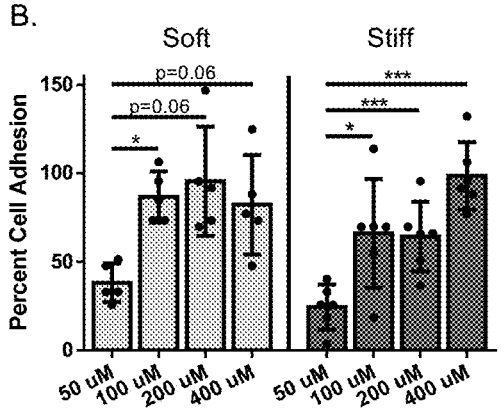
Figure 9:
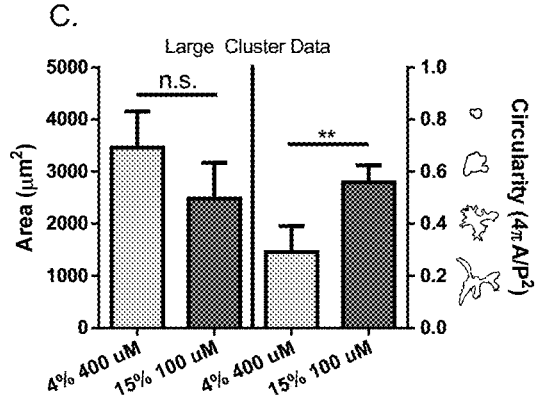
Figure 9:
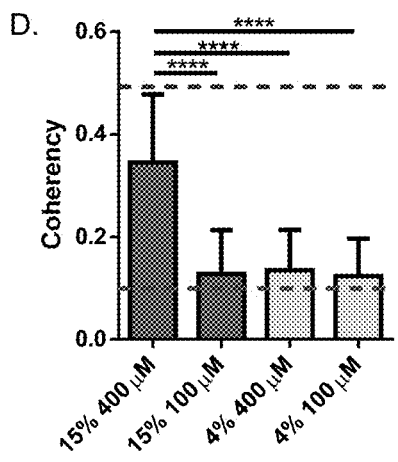
Figure 9:
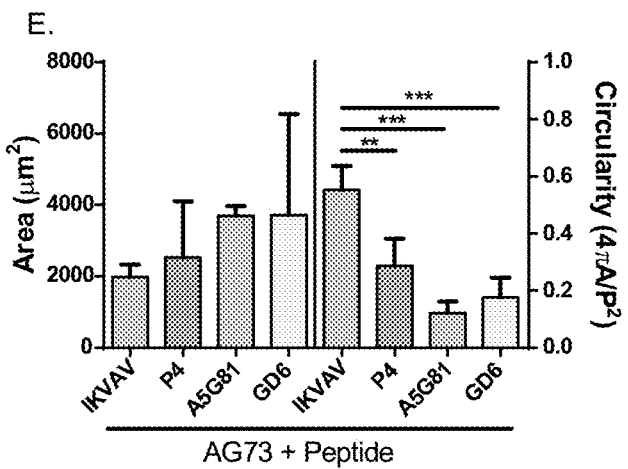

Stiff low peptide density and soft high peptide density hydrogels both support cell viability in 3D to similar degrees as soft PEG-LM (see e.g., FIG. 8A, FIG. 8B). The stiff low peptide density and soft high peptide density hydrogels both exhibited gene expression profiles for NP-specific phenotypic markers (e.g., ACAN, COL2A1, GLUT1, CDH2) which were generally equal to or greater than that exhibited by cells cultured in 4% PEGLM gels (see e.g., FIG. 8C).

Discussion

The data suggest the ability of the peptide-functionalized hydrogel system (both soft high peptide density and stiff low peptide density) to support 3D culture of human adult NP cells. Furthermore, the gene expression data demonstrates the ability of these formulations to promote cells to express NP cell-specific markers of phenotype at levels similar to or greater than cells cultured in soft PEG-LM gels.

Thus, stiff, low peptide density substrates may have applicability for in vitro as a cell culture system or for in vivo applications as cell-laden or cell-less constructs.

Example 4: Engineering Laminin-Mimetic Peptide Systems for 2D and 3D Support of NP Cell Culture The following example describes the characterization of cell morphology using some of the peptides described herein.

Introduction

Intervertebral disc (IVD) aging is associated with changes in extracellular matrix (ECM) biochemistry and cellular phenotype that may contribute to pathologies of disc herniation, stenosis, and degeneration. Specifically, nucleus pulposus (NP) cells that originate from the embryonic notochord undergo a differentiation to a fibroblast-like state with aging[1, 2, 3]. Biomaterials have been developed with the goal of promoting the re-expression of particular features of the juvenile cellular phenotype for human degenerative IVD cells[4, 5]. We have previously shown that soft substrates (~0.3 kPa) conjugated with full length laminin (LM-111) protein promote increased sGAG deposition, increased metabolic activity, and increased mRNA of a panel of genes associated with the healthy NP state[4, 5]. However, the engineering of biomaterials with a single isoform of full-length laminin is associated with variability in functionality of the protein and difficulties in achieving precise control over biomaterial structure. In the current work, we seek to develop 2D and 3D polymeric systems using laminin-mimetic peptides derived from multiple laminin isoforms in order to have greater control over NP cellular phenotype in a more precise manner.

Methods

Maleimide terminated 8-arm poly(ethylene glycol) (8-arm PEG-MAL) monomers were pre-conjugated with cell adhesive peptides (syndecan-binding AG73, and integrin-binding IKVAV, P4, A5G81, and GD6, all of which are localized to the LG domains of different full length laminin isoforms). Following pre-conjugation, 8-arm PEG-MAL was crosslinked using PEG dithiol (SH-PEG-SH) in a Michael type addition reaction to form a peptide presenting hydrogel. Variations in stoichiometry (ratio of MAL:SH) and percentage of total PEG (w/v) allowed for control of hydrogel stiffness and reactive group availability. Experimental conditions included soft (~0.5 kPa) and stiff (~10 kPa) substrates, as well as variable peptide densities (50, 100, 200, and 400 μM). Adult human NP cells from to-be-discarded surgical tissue were isolated as previously described[5], seeded atop the hydrogels, and cultured at 37° C. For 3D culture conditions, cells were resuspended directly in PEG-dithiol solution (PEG-dithiol in 1×PBS pH 7.4) prior to reacting with PEG-MAL-peptide to form the 3D cell-laden constructs. PicoGreen and DMMB assays were used to quantify DNA and glycosaminoglycan production respectively. Cells were immunostained and imaged to quantify cell body circularity and spread area, as well as relative expression of different proteins associated with the juvenile NP phenotype (CellProfiler™, ImageJ). Gene expression of select targets associated with the juvenile NP were also quantified using qPCR. Evidence of differences in these parameters amongst substrates were tested using a one-way ANOVA with Tukey's multiple comparisons test ($\alpha<0.05$, GraphPad Prism).

Results

Figure 10:
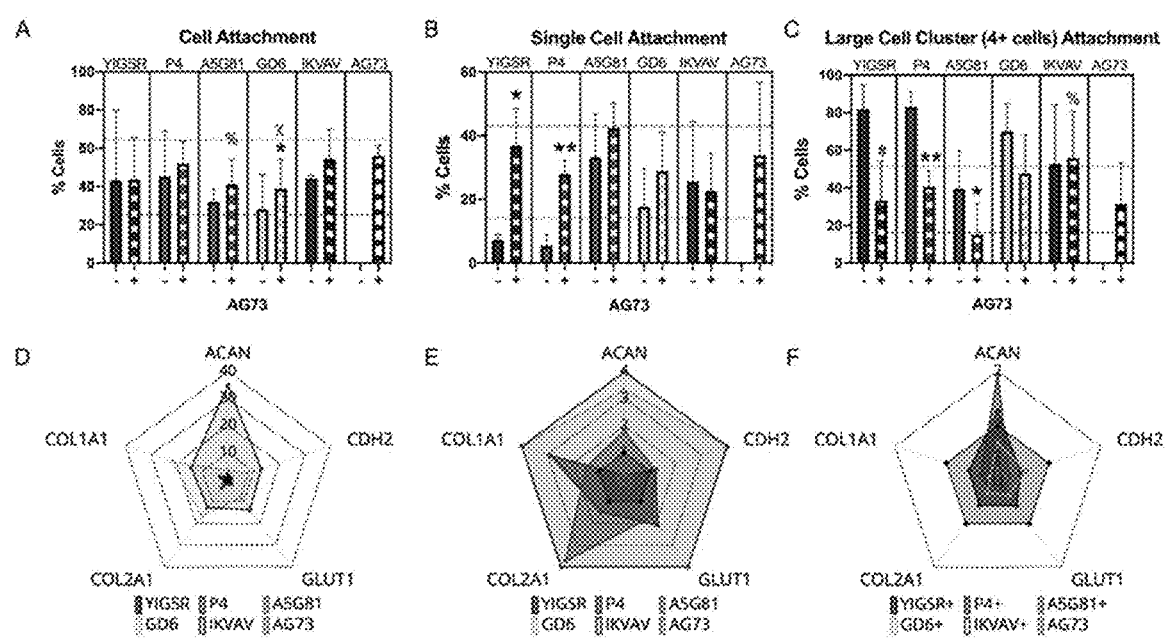
FIG. 10. Characterization of PEG gels conjugated with integrin-binding and/or syndecan binding peptide A) NP Cell attachment B) % of NP cells attaching to gels as single cells C) % of NP cells attaching to gels as large clusters (4+ cells) D) Relative expression of phenotypic markers for cells cultured on gels functionalized with a single peptide. E) Relative expression of phenotypic markers for cells cultured on gels functionalized with a single peptide, axes scaled to visualize lower expressing genes. F) Relative expression of phenotypic markers for cells cultured on gels functionalized with an integrin binding peptide in combination with a syndecan-binding peptide AG73 (+). Axes (D-F)=relative gene expression. Relative gene expression was calculated via $2^{-\Delta\Delta C_t}$ method comparing gene expression to household genes 18S and GAPDH and then to cells cultured on AG73 gels. For all plots: Data from n≥3 patients; dotted line=average value on 4% PEGLM; dashed line=average value on polystyrene; t-tests comparing single peptide to dual peptide gels: ** p<0.0001,  p<0.01, * p<0.05, #p<0.09; comparing dual peptide gels to syndecan-binding peptide: % p<0.05, χp<0.09.

We observed an ability to mimic the behaviors of laminin-presenting substrates with culture of cells atop high peptide density/soft hydrogel (soft/high), as well as low peptide density/stiff systems (stiff/low). In both of these conditions, cell morphologies were indistinct, yet different from the increased cell spread area and high actin alignment observed when cultured atop stiff/high and tissue culture glass, which led to a more fibroblast-like behavior (FIG. 10A, FIG. 10C, FIG. 10D). Additionally, both soft/high and stiff/low substrates led to gene expression profiles and sGAG deposition levels that were similar to or higher than what was observed for cells cultured on soft PEG-laminin. Cells exhibited similar morphologies when cultured atop hydrogels functionalized with the combination of any LG-domain-localized integrin-binding peptide and syndecan-binding AG73 (FIG. 10 E). For cells cultured in 3D (soft/high and stiff/low), we observed an increase in luminescence, suggesting slight cell proliferation over the two-week culture period (data not shown).

Discussion

These results suggest an ability to manipulate cell phenotype using both soft and stiff hydrogel systems by control of ligand density using peptide-hydrogel substrates. We observed an ability to create peptide-presenting substrates with bioinductive properties that promote re-expression of a panel of markers associated with the healthy NP cell phenotype. We benchmarked our data against a soft PEG-LM system as this has been previously shown to promote rejuvenation of NP cells[4]. Furthermore, integration of adhesive domains that promote differential cellular interactions (i.e., via engagement of different integrins, syndecans) can provide phenotypic control. Ongoing studies will determine our ability to apply these systems to 3D cell culture, as well as to study biomaterial effects on metabolic activity and biosynthesis of our cells.

Clinical Relevance

Materials-based approaches for restoring both mechanical properties as well as cellular bioactivity to the disc may provide a new approach for treating degenerative disc disease. The ability to promote specific juvenile cell behaviors using in situ crosslinking, injectable stiff biomaterials presents the added benefit of providing improved mechanical stability to a hydrogel system which may be used as an implantable device.

REFERENCES

1) Setton, *J Bone and Joint Surgery* 2006
2) Urban et al. *Arthritis Research & Therapy* 2003
3) Trout et al. *Tissue & Cell* 1982
4) Francisco et al. *Acta Biomaterialia* 2014
5) Bridgen et al. *Acta Biomaterialia* 2017

Example 5: Characterization of PEG Gels Conjugated with Integrin-Binding and/or Syndecan Binding Peptides This example describes the ability to conjugate laminin-mimetic peptides to a PEG backbone in order to create hydrogels that support cell attachment, cluster formation, and phenotype of NP cells.

Data on the following peptides and combinations of peptides have been obtained: YIGSR, P4, A5G81, GD6, IKVAV, AG73, YIGSR+AG73, P4+AG73, A5G81+AG73, GD6+AG73, and IKVAV+AG73. FIG. 10 is a representative example of this data.

FIG. 10 shows how dual peptide materials (e.g., PEG gels conjugated with integrin-binding and/or syndecan binding peptides) can regulate cell phenotype and attachment.

Example 6: Engineered Peptide-Functionalized Hydrogels Modulate RNA Transcriptome of Human Nucleus Pulposus Cells In Vitro The following example describes transcriptome changes for cells cultured on the IKVAV+AG73 gels.

Abstract

Degeneration and aging of the nucleus pulposus (NP) of the intervertebral disc (IVD) is accompanied by alterations in NP cell phenotype marked by reduced cellularity and a shift towards a fibroblast-like state. We have recently demonstrated an ability to manipulate the phenotypic expression of adult degenerative NP cells by culture upon poly(ethylene glycol) (PEG) based hydrogels dually functionalized with integrin- and syndecan-binding laminin-mimetic peptides. Periods of culture for human NP cells derived from degenerative tissue upon PEG-peptide gels led cells to assume phenotypes more consistent with the cells of the healthy NP. In the present study, we seek to understand the transcriptome changes elicited by NP cell interactions with the presented hydrogel system. The data corroborate and expand on the previous findings by demonstrating that degenerative adult human NP cells cultured upon these gels have upregulations in some markers of NP and notochordal cells but also downregulations of some NP-specific markers and several fibroblastic markers. Furthermore, through gene set enrichment analysis we have shown that pathways related to cell differentiation and notochord morphogenesis were upregulated in the gel condition. Additionally, 13 genes associated with G protein-coupled receptors, many of which are known drug targets, were identified as up or downregulated following periods of culture upon the gel condition.

Statement of Significance

Cells of the nucleus pulposus (NP) of the intervertebral disc undergo phenotypic changes with age and degeneration. Previous studies for NP and other cell types suggest an ability to control cell phenotype by varying microenvironmental cues of stiffness and ligand presentation of the cell culture substrate. The current study explores how an engineered peptide-polymer material can modulate gene expression and pathway activation in human NP cells. RNA-seq profiling demonstrates an ability for the peptide-polymer material to elicit elevated expression for some, but not all markers of the NP cell, and shed light on unstudied pathways that may be regulated by microenvironmental cues.

Introduction

The nucleus pulposus (NP) of the intervertebral disc has been observed to undergo considerable changes in matrix composition and overall biochemical makeup with age and maturation [1-5]. The cells of the NP are derived from the embryonic notochord, which expresses an array of signaling molecules and transcription factors such as brachyury (T), noggin (NOG), and notochord homeobox (NOTO), some of which are observed to disappear during early developmental stages [4,6]. These cells secrete a matrix rich in collagens, predominantly collagen type II, proteoglycans, and other proteins such as laminins and fibronectin [2,7,8]. With degeneration, there is a loss of hydration in the NP of the IVD that contributes to tissue stiffening and reduced IVD height, with NP shear moduli values increasing from <1 kPa in healthy NP to 10-20 kPa in moderately degenerated NP [1,7,9-11]. These changes are associated with a decrease in NP cellularity and a shift towards more fibroblast-like cell phenotype with altered biosynthesis including secretion of a matrix with decreased sulfated glycosaminoglycans (sGAGs), decreased collagen type II, and increased collagen type I [12-14]. Changes have also been observed in the presence of matrix degrading enzymes such as the MMP and ADAMTS families, which results in an altered cellular microenvironment and a decreased ability for tissue repair and homeostasis [4,15-17]. Literature has suggested that culture of NP cells upon soft (~500 Pa) hydrogel substrates functionalized with laminin-111 can lead to a partial re-expression of markers of the juvenile NP, while stiff (10-20 kPa) hydrogel substrates or tissue culture plastic will shift cells towards the fibroblast-like phenotype over time [9,18,19].

There exists a large body of work describing substrate control for regulation of cell phenotype using an assortment of materials with varied stiffness and elasticity, porosity and type and extent of functionalization [20-24]. Within the field of studies performed with IVD cells, investigators have used cell culture scaffolds composed of hyaluronic acid, alginate, and PEG amongst others to control cell phenotype [9,18,25,26]. In the case of NP cells, while it has been suggested that stiff biomaterials promote a more fibroblastic cell phenotype, recent work has suggested that density of ligand presentation in the biomaterial can also be an important factor regulating cell phenotype [14]. In particular, we previously demonstrated that functionalization of a stiff poly(ethylene glycol) (PEG) with a precise combination of laminin-derived peptides, IKVAV and AG73, could lead to a partial re-expression of a panel of juvenile markers for human degenerate NP cells [14]. In the current work we sought to better understand the gene expression profiles and pathway activation in human NP cells induced by periods of culture upon these stiff, peptide-functionalized PEG hydrogels [14]. RNA-sequencing of RNA isolated from human degenerate NP cells was performed after periods of culture upon PEG-peptide hydrogels or tissue culture polystyrene (TCPS) in order to better understand the unique contributions of adhesive ligand presentation to regulating NP cell phenotype in vitro.

Materials and Methods

NP Cell Isolation

Primary adult human NP cells were isolated from to-be-discarded surgical tissue of patients with degeneration-associated complications (n=3, both sexes, ages 24-55, in accordance with procedures from Washington University Institutional Review Board) as previously described [19]. NP fragments were identified, separated from AF and cartilaginous tissues, and digested for 2-4 h at 37° C. and 5% $CO_2$ in digestion medium containing 0.4% type 2 collagenase (Worthington Biochemical, Lakewood, NK) and 0.2% pronase (Roche, Basel, Switzerland). Following, the tissue digest was passed through a 70 µm filter, and cells were pelleted (in centrifuge for 10 minutes at 400 rcf), resuspended, and cultured in Ham's F12 medium (Thermo Fisher Scientific, Waltham, MA) supplemented with 10% fetal bovine serum (FBS) and 1% penicillin-streptomycin. Cells were expanded in normoxic culture on tissue culture polystyrene (TCPS) in F12 media supplemented with 10% FBS and 1% penicillin-streptomycin; all cells used for experiments were low passage numbers (passage 2: 55M, passage 3: 53F and 24F).

Hydrogel Preparation

Hydrogels were prepared as previously described [14]. Briefly, lyophilized, cysteine terminated IKVAV and AG73 peptides (full sequences for IKVAV and AG73: CSRARKQAASIKVAVSADR (C terminated SEQ ID NO: 2), and CGGGRKRLQVQLSIRT (CGG-terminated SEQ ID NO: 1) respectively, GenScript, Piscataway, NJ) were dissolved in 1xPBS pH 3.25. The GG is a spacer, any suitable spacer can be used. Peptide solutions were added to a maleimide terminated 8-arm star poly(ethylene glycol) (PEG-8MAL, MW 20K, Creative PEGWorks, Durham, NC) for the functionalization of the 8-arm PEG backbone [27]. A small PEG-dithiol (SH-PEG-SH, MW 600, Creative PEG-Works) was likewise dissolved in 1xPBS pH 3.25, and then added to the peptide-PEG-8MAL solution to initiate cross-linking and hydrogel formation.

Gels were permitted to crosslink for 1 hour, then neutralized with 1xPBS pH 7.4 and allowed to swell to equilibrium volume. PEG-peptide gels were made at 15% PEG w/v, previously measured to have a stiffness ~10 kPa, and functionalized with 100 µM total peptide using equimolar amounts of IKVAV and AG73 [14].

RNA Sequencing

Primary adult human NP cells from three patients (55-year-old male, 24-year-old female, and 53-year-old female) were seeded in triplicate upon PEG-peptide gels or TCPS at a density of 100,000 cells per well using a 4-well chamber slide (Nunc Lab-Tek Chamber Slide Systems™, ThermoFisher Scientific, Waltham, MA), consistent with previously published protocols [14,28]. Cells were cultured for 4 days at 37° C. and 5% $CO_2$. Following the incubation period, the cells were lysed using RLT buffer (Qiagen, Hilden, Germany)+1% mercaptoethanol and stored at −80° C. until ready for RNA isolation. Isolation was done using the Qiagen Mini Kit following manufacturer instructions (Qiagen, Hilden, Germany). RNA qualities were measured using a Bioanalyzer (Agilent, Santa Clara, CA), and all samples used had an RNA integrity number (RIN)>9. ds-cDNA was made using Clontech SMARTer® Ultra Low RNA Kit (Clontech, Mountain View, CA) following manufacturer's recommendations. cDNA was fragmented using a Covaris E220 sonicator (peak incident power=18, duty factor=20%, cycles per burst=50, for 120 seconds). Ligated fragments were amplified for 12 cycles using primers incorporating dual index tags. Fragments were then run on an Illumina NovaSeq (San Diego, CA) reading 150 bases from both ends to a depth of 30 million reads. Using Partek Flow® (Partek Inc., St. Louis, MO), unaligned reads were trimmed prior to alignment to the human genome (STAR 2.6.1d and referencing to the human genome hg19). Gene Specific Analysis was conducted in Partek Flow® and used to perform downstream analysis (identification of differentially expressed genes, principal component analysis, hierarchical clustering, and gene set enrichment) using the same methodology as previously described [28]. Fold change (Gel/TCPS) was computed as the average normalized count for all 3 patients in the Gel group and divided by the average normalized count for all 3 patients in the TCPS group. The fold change values were thus presented as a single data point which reflects the inputs from 3 separate human patients [28]. The RNA sequencing dataset generated during this study was deposited in the NCBI Gene Expression Omnibus (GEO) repository (GSE154044).

Statistical Analysis

Statistical analyses were performed within Partek Flow®. Fold change values for each gene were calculated as an average normalized count for the 3 patients cultured on the PEG-peptide gel divided by the average normalized count for the 3 patients cultured on TCPS. Therefore, for each gene a single fold change value was presented, although this reflects inputs from 3 separate human patients. Genes were considered significant at a fold change value (PEG-peptide gel/TCPS)≥2 (upregulated) or ≤−2 (downregulated). The most up- and down-regulated genes were identified as those with the highest or lowest fold change values, p-values<0.05, and with known molecular function and/or biologic process gene ontology terms (UniProt database).

Results

Global Gene Expression of NP Cells is Altered by Culture on PEG Gels Functionalized with IKVAV and AG73

Figure 11:
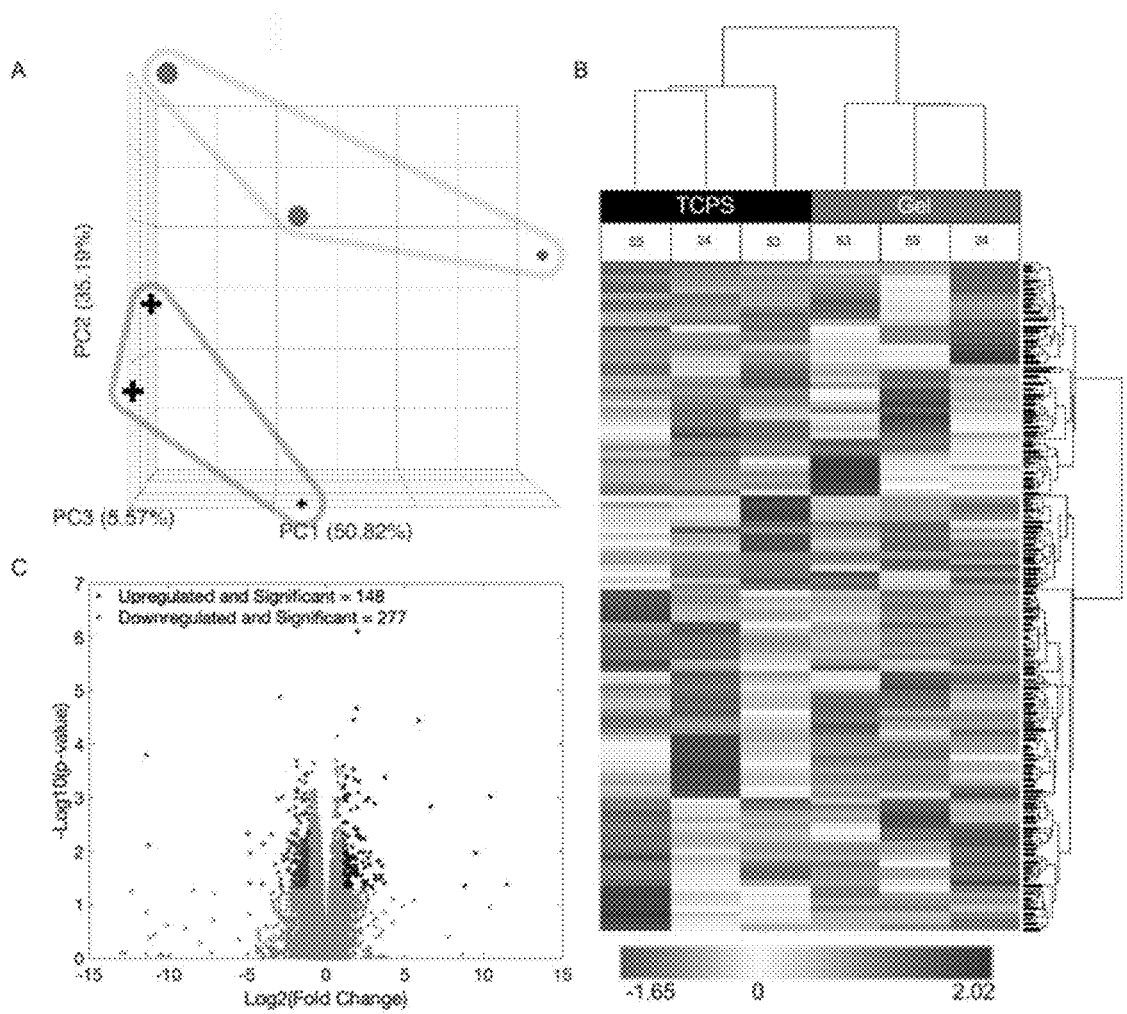
FIG. 11. A. PCA analysis of cells cultured on 15% 100 μM AG73+IKVAV conjugated gels (green circles) or uncoated tissue culture polystyrene (TCPS; black crosses). Each dot represents NP cells from a human patient (24, 53, 54-year-old, size of symbol increases with patient age). B. Hierarchical clustering of RNA-sequencing data from cells on the TCPS or gel. Each column shows data from a given patient as indicated by patient age (55, 24, or 53), z-score of gene expression is plotted across rows (downregulated genes=red, upregulated genes=blue). C. Volcano plot shows differentially regulated genes (downregulated=red, upregulated=blue) and genes which are not differentially regulated (grey).

PCA analysis revealed that while there was some separation of data due to inter-patient variability, the RNA samples from cells cultured on PEG-peptide gels clustered distinctly from cells cultured on TCPS (FIG. 11A). Hierarchical clustering further confirmed separation in gene expression between cells cultured on the gel and TCPS conditions (FIG. 11B). Compared to cells on TCPS, culture on PEG-peptide gels resulted in 425 differentially regulated genes-148 upregulated and 277 downregulated genes (FIG. 11C).

Figure 12:
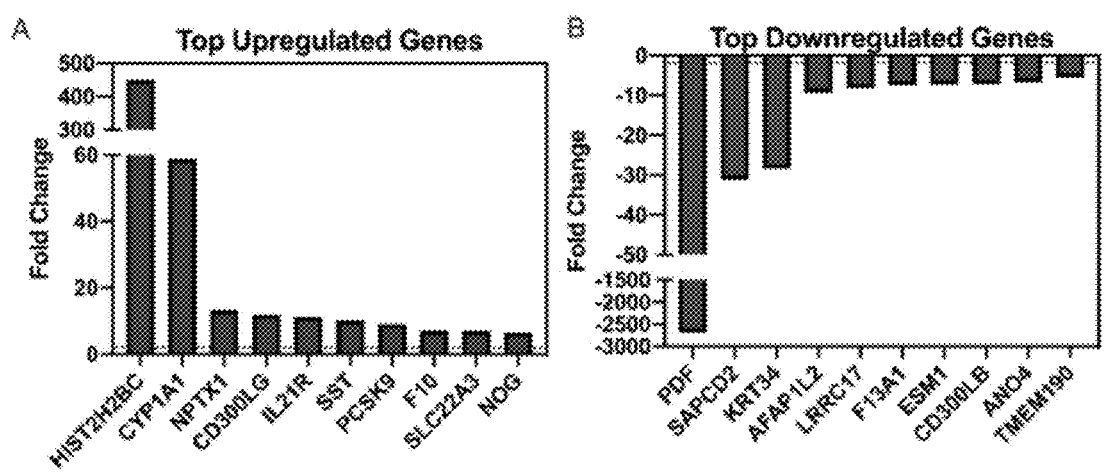
FIG. 12. A. Fold change values of 10 most upregulated genes (gel v. TCPS) B. Fold change values of 10 most downregulated genes (gel v. TCPS). Horizontal dotted lines denote 2 and −2-fold change, respectively.

The most upregulated genes (with significant p-values) are given in FIG. 12A and TABLE 1 and include noggin (NOG), an important protein involved in regulating musculoskeletal system development. Many of the most upregulated genes were associated with intra-cellular signaling including Somatostatin (SST), Proprotein convertase subtilisin/kexin type 9 (PCSK9), and Solute carrier family 22 member 3 (SLC22A3). The most downregulated genes (with significant p-values) are given in TABLE 2 and shown in FIG. 12B and also include genes regulating intra-cellular signaling such as mitochondrial peptide deformylase (PDF), Suppressor APC domain-containing protein 2 (SAPCD2), Actin filament-associated protein 1-like 2 (AFAP1L2), Leucine-rich repeat-containing protein 17 (LRRC17), Coagulation factor XIII A chain (F13A1), Endothelial cell-specific molecule 1 (ESM1), CMRF35-like molecule 7 (CD300LB), Anoctamin-4 (ANO4), and Transmembrane protein 190 (TMEM190).

TABLE 1

Gene symbol, name, fold change, and p-value of 10 most upregulated genes (gels v. TCPS).

| Gene Symbol | Gene Name | Fold Change | P-value |
| --- | --- | --- | --- |
| HIST2H2BC | Putative histone H2B type 2-C | 451.39 | 4.5e−2 |
| CYP1A1 | Cytochrome p450 1A1 | 58.79 | 3.6e−5 |
| NPTX1 | Neuronal pentraxin-1 | 13.33 | 4.1e−4 |
| CD300LG | CMRF35-like molecule 9 | 11.93 | 1.9e−2 |
| IL21R | Interleukin-21 receptor | 11.23 | 2.8e−2 |
| SST | Somatostatin | 10.10 | 1.5e−2 |
| PCSK9 | Proprotein convertase subtilisin/kexin type 9 | 8.99 | 3.3e−2 |
| F10 | Coagulation factor X | 7.08 | 4.4e−2 |
| SLC22A3 | Solute carrier family 22 member 3 | 6.97 | 1.1e−2 |
| NOG | Noggin | 6.48 | 1.0e−3 |

TABLE 2

Gene symbol, name, fold change, and p-value of 10 most downregulated genes (gels v. TCPS).

| Gene Symbol | Gene Name | Fold Change | P-value |
| --- | --- | --- | --- |
| PDF | Peptide deformylase, Mitochondrial | −2683 | 1.6e−4 |
| SAPCD2 | Suppressor APC domain-containing protein 2 | −31.2 | 4.7e−3 |
| KRT34 | Keratin, type I cuticular Ha4 | −28.35 | 3.9e−2 |
| AFAP1L2 | Actin filament-associated protein 1-like 2 | −9.36 | 1.7e−2 |
| LRRC17 | Leucine-rich repeat-containing protein 17 | −8.25 | 1.1e−3 |
| F13A1 | Coagulation factor XIII A chain | −7.45 | 1.3e−5 |
| ESM1 | Endothelial cell-specific molecule 1 | −7.25 | 4.0e−2 |
| CD300LB | CMRF35-like molecule 7 | −7.13 | 4.6e−2 |
| ANO4 | Anoctamin-4 | −6.68 | 9.5e−4 |
| TMEM190 | Transmembrane protein 190 | −5.56 | 1.4e−2 |

Figure 13:
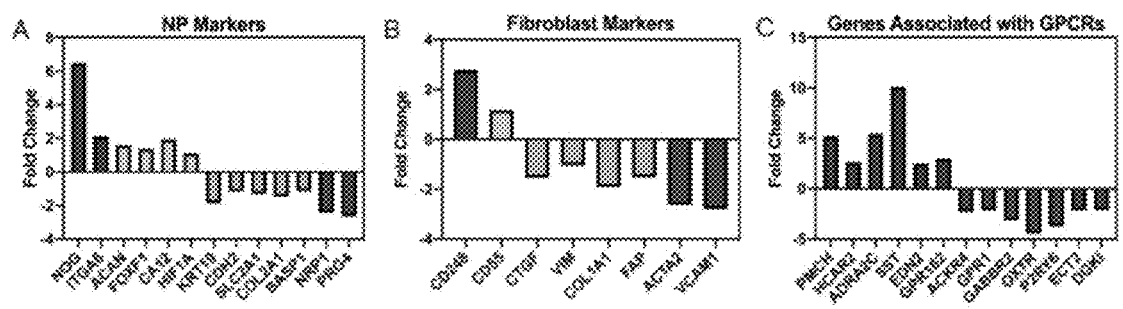
FIG. 13. A. Expression of a panel of NP phenotypic markers. B. Expression of a panel fibroblast markers C. Up- and downregulated genes associated with G protein coupled receptors (GPCRs). (Fold change=gel v. TCPS; bars with opaque color had fold change values greater than or equal to 2 or less than or equal to −2).

Markers of NP Cell and Fibroblast Phenotype were Differentially Regulated Through Culture on PEG-Peptide Hydrogels When cells were cultured on the gel substrate, several markers of NP cell phenotype were upregulated including Noggin (NOG) and Integrin α6 (ITGA6) (FIG. 13A). Other markers of the NP phenotype that were moderately increased (but did not exceed a fold change value of 2) included Aggrecan (ACAN), Forkhead Box F1 (FOXF1), Carbonic anhydrase 12 (CA12), and Hypoxia-inducible factor 1 (HIF1A). Markers including Neuropilin 1 (NRP1) and Proteoglycan 4 (PRG4) were downregulated (FIG. 13A) while others were modestly reduced in expression (but did not reach a fold change value of −2) including: Cytokeratin 19 (KRT19), N-cadherin (CDH2), Solute carrier family 2, facilitated glucose transporter member 1 (SLC2A1), Collagen alpha-1 (II) chain (COL2A1), and Brain acid soluble protein 1 (BASP1). Expression of a panel of fibroblast markers was also examined (FIG. 13B). While some genes in the cells cultured on gels were observed to be upregulated (CD55 molecule (CD55), and Endosialin (CD248)), others were downregulated including: CCN family member 2 (CTGF), Vimentin (VIM), Collagen alpha-1 (I) chain (COL1A1), Prolyl endopeptidase FAP (FAP), Actin, aortic smooth muscle (ACTA2), and Vascular cell adhesion protein 1 (VCAM1).

Genes Related to G Protein-Coupled Receptors were Among Both Upregulated and Downregulated Genes Amongst the up- and down-regulated genes, 13 genes associated with G protein-coupled receptors (GPCR) were identified (FIG. 13C). These genes were: Pro-MCH (PMCH), Hydroxycarboxylic acid receptor 2 (HCAR2), Alpha-2C adrenergic receptor (ADRA2C), Somatostatin (SST), Endothelin-2 (EDN2), and Probable G-protein coupled receptor 162 (GPR162). Other GPCR-associated genes were downregulated and included: Atypical chemokine receptor 4 (ACKR4), G-protein coupled receptor 1 (GPR1), Gamma-aminobutyric acid type B receptor subunit 2 (GABBR2), Oxytocin receptor (OXTR), P2Y purinoceptor 6 (P2RY6), Protein ECT2 (ECT2), and Diacylglycerol kinase iota (DGKI).

Figure 14:
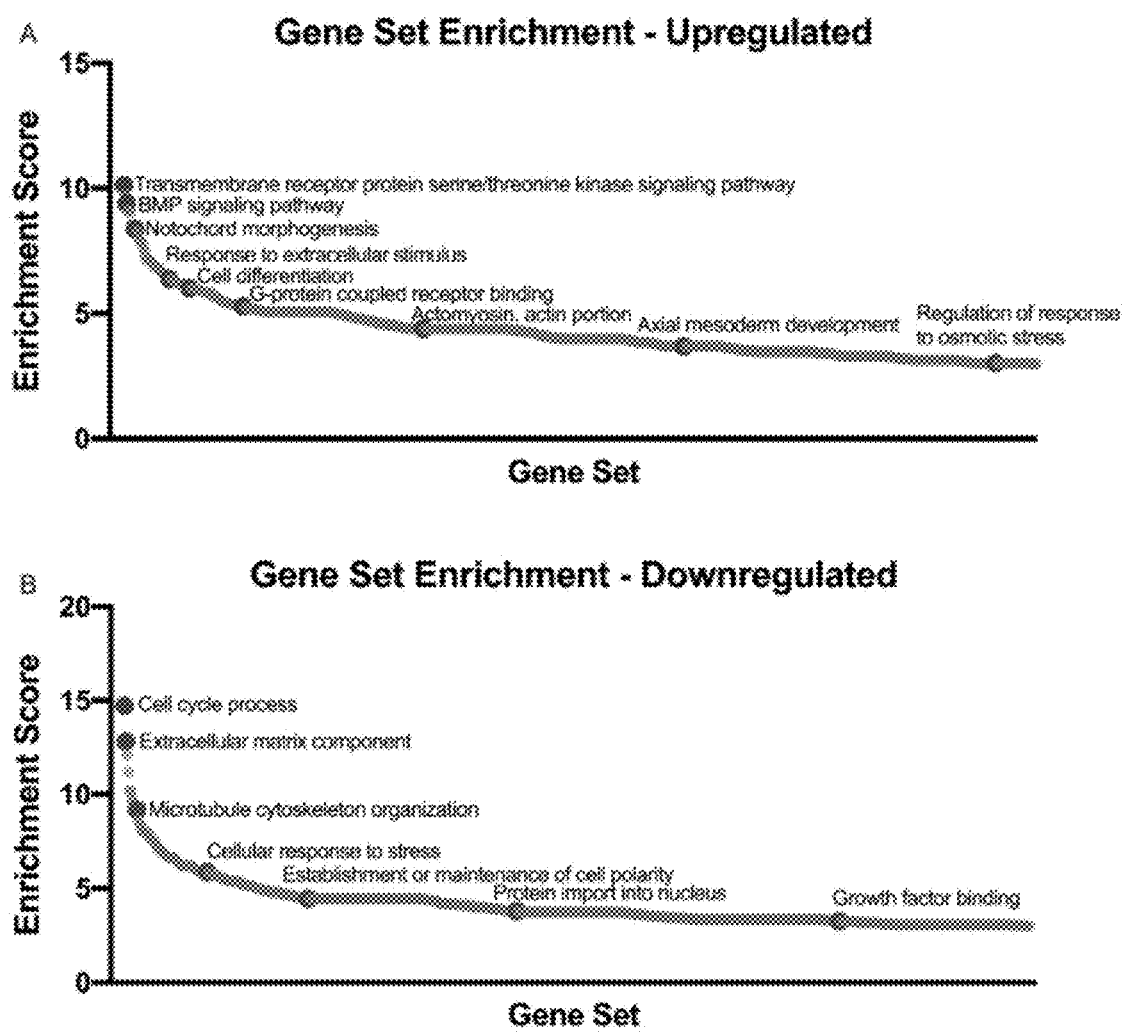
FIG. 14. Enriched gene sets in the upregulated (A) and downregulated genes (B) with notable gene sets labeled.
Figure 15:
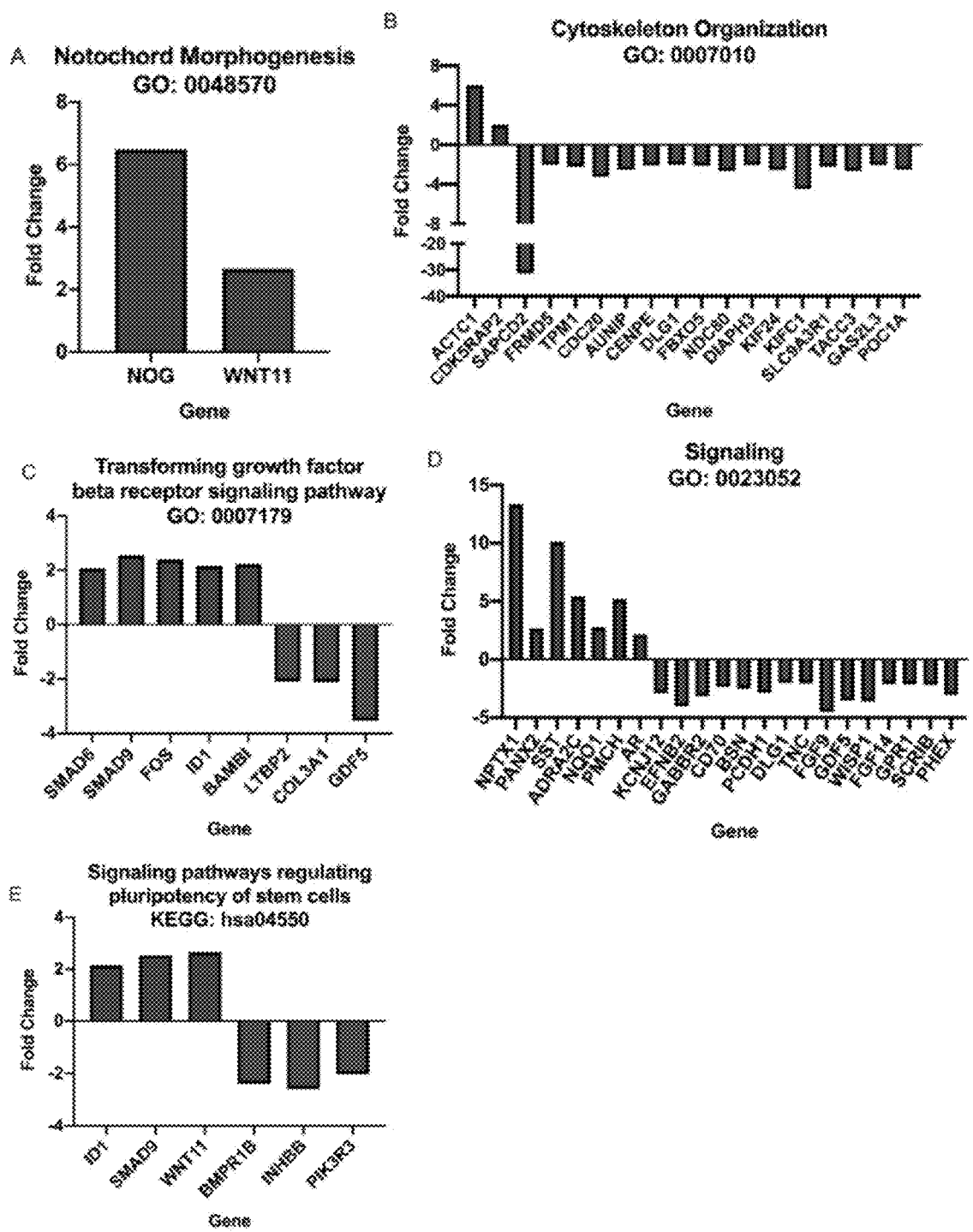
FIG. 15. Fold change values (gel v. TCPS) of genes associated with gene ontology terms A. Notochord morphogenesis B. Cytoskeleton Organization C. Transforming growth factor beta receptor signaling pathway D. Signaling E. Signaling pathways regulating pluripotency of stem cells.

Gene Set Enrichment Analysis Reveals Pathways and Cellular Components Implicated in NP Cell Culture on PEG-Peptide Gels Gene set enrichment was performed on the list of upregulated and downregulated genes and yielded 721 and 716 significantly enriched gene sets respectively. The enriched gene sets within the upregulated genes represented cellular processes including cellular differentiation, cell signaling, and cytoskeletal regulation (FIG. 14A). The top 10 enriched pathways from the upregulated genes include pathways related to organ morphogenesis, including notochord morphogenesis, intracellular signaling pathways (including transforming growth factor beta receptor, TGFb, and bone morphogenic protein, BMP) and transport of solutes and ions (TABLE 3). The gene sets enriched from the downregulated genes included those around themes including cell cycle and DNA processes, extracellular matrix components, and cytoskeletal organization particularly related to cellular division (FIG. 14B and TABLE 3). Furthermore, genes implicated in these gene sets (gene ontology, GO, terms) were examined. In the notochord morphogenesis (GO term: 0048570) gene set, noggin (NOG) and protein WNT-11 (WNT11) were upregulated while this pathway was not associated with the significantly downregulated genes (FIG. 15A). Other gene sets including Cytoskeleton Organization (GO: 0007010), Transforming growth factor beta receptor signaling pathway (GO: 0007179), Signaling (GO: 0023052), and the KEGG pathway Signaling pathways regulating pluripotency of stem cells (hsa04550) were associated with both significantly upregulated and downregulated genes (FIG. 15B-E).

TABLE 3

Top 10 most enriched gene sets associated with the upregulated and downregulated genes.

| | Top Gene Sets Enriched-Upregulated gel v. TCPS |
|---|---|
| 1 | transmembrane receptor protein serine/threonine kinase signaling pathway |
| 2 | antiporter activity |
| 3 | solute:proton antiporter activity |
| 4 | formation of primary germ layer |
| 5 | BMP signaling pathway |
| 6 | zygotic specification of dorsal/ventral axis |
| 7 | ion antiporter activity |
| 8 | transforming growth factor beta receptor signaling pathway |
| 9 | notochord morphogenesis |
| 10 | alpha-2A adrenergic receptor binding |
| | Top Gene Sets Enriched-Downregulated gel vs. TCPS |
| 1 | cell cycle process |
| 2 | extracellular matrix component |
| 3 | DNA metabolic process |
| 4 | chromosomal region |
| 5 | mitotic cell cycle process |
| 6 | spindle organization |
| 7 | microtubule cytoskeleton organization involved in mitosis |
| 8 | DNA replication initiation |
| 9 | DNA replication |
| 10 | microtubule cytoskeleton organization |

Discussion

It has widely been demonstrated that many cell types are able to robustly sense and respond to physical and chemical features of their environment. These responses can be harnessed by using engineered substrates with defined features, such as the PEG-peptide gel studied here, to promote cell differentiation or phenotypes in vitro or for treatment of diseases in vivo. Characteristics that have been shown to modulate cell behavior in 2D include the stiffness of the underlying substrate, ligand presentation, geometry of adhesive area, and ligand density [9,19,20,28-34]. A particular role of ligand density in controlling NP cell behavior was recently reported [14]. That study suggested that a stiff gel (15% PEG) conjugated with equimolar amounts of the laminin-mimetic peptides AG73 and IKVAV at a total density of 100 µM could promote degenerative cells to assume a phenotype consistent with healthy, juvenile NP cells [14]. Healthy phenotype cells can be produced in a material of any variety of cell-adhesive peptide and polymer concentrations. For example, the cell-adhesive peptide or a combination of one or more cell-adhesive peptide can be between 10 µM and 400 µM or between 10 µM and 1000 µM. As another example, a total polymer or polymer-peptide density can be between about 2% and 40% (w/v). In particular, this work demonstrated an ability for peptide-presenting substrates to promote an increase in gene expression of ACAN and CDH2 as well as an increase in protein expression of BASP1, N-Cadherin, integrin alpha 6, and pan-cytokeratin in cells compared to cells cultured upon TCPS [14]. Rather than only focus on pre-selected molecular targets, we sought in the current study to examine the broader profile of differential mRNA expression for degenerative NP cells cultured on these substrates. Results suggest an ability for the biomaterial to alter pathways and cellular function in ways that corroborate, as well as expand on, the previous study. Hierarchical clustering and PCA analysis demonstrate separation in the transcriptomes of degenerative NP cells cultured on the gel compared to TCPS, a finding that was consistent across samples. These findings, like prior literature, suggest that features of the underlying substrate can control global gene expression in cells [20,35,36].

The data further demonstrate that culture of degenerative adult human NP cells on the gel may cause an increased expression of markers associated with juvenile NP cells, including NOG and ITGA6. Furthermore, expression of many fibroblastic markers including CTGF, ACTA2, VCAM1, and FAP were downregulated. Taken together with data from Barcellona and co-workers, these findings suggest that adult degenerative NP cell phenotype may be modulated to shift towards a more juvenile NP state [14]. However, interactions with the gel may be unable to completely alter cell phenotype—this is consistent with previous studies which have shown substrate parameters such as geometry have been able to promote MSC differentiation towards a particular lineage but may be insufficient to fully promote cell differentiation [35]. The NP marker NOG which is associated with notochord development was amongst the most highly upregulated genes [6]. Other highly upregulated terms included genes associated with differentiation including epigenetic regulation (HIST2H2BC) and nervous system development (NPTX1). NPTX1 has been shown to be upregulated in MSCs as well as being differentially regulated in notochordal, nucleus pulposus, and anulus fibrosus samples [38-40]. Here, the receptor for somatostatin (SST) was also upregulated following culture upon the PEG-peptide gels which is of interest as the ligand SST has been identified as a potential target for the prevention of IVD cell senescence [41,42]. Amongst the most highly downregulated genes, several have been associated with angiogenesis, musculoskeletal development, inflammation, and immune response. AFAP1L2 (also known as XB130), one of the most highly downregulated genes in this data set, codes for an adaptor protein that mediates intracellular signal transduction through the PI3K/AKT signaling pathway to regulate proliferation, motility and cell survival as well as having implications in inflammation through Src and IL-8 signaling [43,44]. Also downregulated by the gel was LRRC1, a known negative regulator of RANKL (receptor activator of NF-kappaB ligand) that has also been shown to be differentially regulated in the context of both nucleus pulposus and chondrocytes [39,46]. A marker of angiogenesis, ESM1, has likewise been shown to be differentially regulated in a study that directed the differentiation of human pluripotent stem cells towards notochord- and nucleus pulposus-like populations [39]. The identification of these up- and down-regulated genes provides targets for further analysis including quantification of protein expression, cellular localization, as well as the elucidation of their role in regulating NP cell phenotypes.

Other targets examined in the present study were genes associated with G protein-coupled receptors (GPCRs) as these are not only regulators of diverse cellular functions, but also a class of receptors that are often druggable targets. The data presented 6 genes that were upregulated and 7 that were downregulated which had GO terms associating them with GPCRs. Interestingly, several of these have been associated previously with the musculoskeletal system and specifically IVD or cartilage. PMCH has not previously been associated with NP phenotype, however studies have shown a role for this GPCR-related gene in early neurogenesis, chondrogenesis, and regeneration as well as in neuropathic and inflammatory pain in a murine animal model [47-50]. HCAR2 has been implicated in macrophage recruitment and inflammatory responses. Protein expression hydroxycarboxylic acid receptor-2 has been found in chondrocytes and peripheral nerve among other tissues [51-53]. Similarly, ADRA2C and SST have been found to be biomarkers in chronic pain for temporomandibular disorder and low back pain [54-56]. Although a study found low ADRA2C expression in cartilage, a recent report found a decrease in expression of the same with IVD degeneration [57,58]. GPR162 (also known as GRCA) has been found in neurons, cartilage, and NP cells [50,53,59,60]. Though the function of this gene is largely unknown, it has been shown to have a role in cytoskeletal organization and to interact with other G protein-coupled receptors (STRING database v11) [61,62]. EDN2 has been found to be involved in the inhibition of vascularization in the retina and other tissues including the IVD. Interestingly, EDN2 has been suggested to be a master regulator of notochordal cell gene expression [63-66]. The upregulation of these genes, some of which have been previously implicated in notochord and healthy features of the NP, provide further data to suggest that culture of degenerative human NP cells upon PEG-peptide hydrogels may promote a shift towards expression of a more juvenile-like NP phenotype.

Examination of the GPCR-associated genes which were downregulated in cells cultured on the gels points to several genes previously shown to have a role in musculoskeletal tissue development or pathology. ACKR4 (also referred to as CCRL1, CCR11, CCX CKR) is a member of the Atypical chemokine receptors family that plays a role in regulating inflammatory responses, yet also shown to be present embryonically during NP development and in musculoskeletal diseases such as rheumatoid arthritis [67-71]. GPR1, downregulated here by periods of culture upon the gel, was found to be upregulated in a study of IVD cells subjected to increased osmolarity [44]. Several studies in bone have shown that GPR1 deficient mice had decreased bone mass and bone marrow density in addition to increased markers of inflammation, although GPR1's role in NP and IVD health has not been elucidated [72,73]. DGKI was also reported to be increased in IVD samples subjected to increased osmolarity and has been implicated in rheumatoid arthritis and osteoarthritis [44,74-77]. Other downregulated GPCR-associated genes (P2RY6, OXTR, GABBR2, and ECT2) have been studied in the context of neurogenic pain, inflammation, and disc or cartilage tissue development/disease [60, 78-86]. However, the role of these genes in regulating cell phenotypes in response to engineered substrates has not previously been elucidated and thus require further validation.

Examination of enriched gene ontology terms in the up- and down-regulated gene sets reveals not only individual gene changes, but also pathways and cellular components that are likely altered by culture upon the gels. This analysis confirmed the enrichment of terms associated with notochord morphogenesis and transforming growth factor beta receptor signaling pathway, a signaling cascade critical for the formation of the notochord and NP [40]. Similarly, pathways related to cell differentiation and response to extracellular stimuli were highly enriched in the data set. Pathways enriched in the downregulated genes suggest that upon culture on gels, genes associated with cell division are reduced and cytoskeletal organization is altered. When the up- and down-regulated gene lists were considered together, additional pathways of interest were enriched including signaling pathways regulating pluripotency of stem cells. While individual genes associated with these terms may be either up or downregulated, their collective contribution to a significant enrichment of each pathways suggests the many ways the NP cells were affected by culture upon the gels.

In this study, the PEG-peptide hydrogel was found to regulate cell shape and cell-cell interactions that were documented with altered morphologies between hydrogel and TCPS substrates. A prior study of adult degenerative NP cells showed that cells forming cell-cell contacts in organized clusters may have upregulated N-cadherin expression and functional N-cadherin signaling that could be an important determinant of NP cell biosynthesis [87], and possibly the differentially expressed RNA transcriptome observed here. Further, the identification of the 400+ differentially regulated genes was based on a sample size of n=3 with the expectation that a larger sample size would yield some, but not major differences in the molecular targets on that list given the strong separation of RNA-seq results based on substrate condition. Additional work is needed to better isolate the relative roles of the specific parameters in the current study such as substrate stiffness, ligand presentation, cell-cell/cell-matrix interactions, and their importance in the modulation of NP cell phenotype. A limitation of the current study is the lack of information on transient cellular responses that could be used to study the concept of mechanical memory, which has been demonstrated to be an important factor in regulating cell synthesis and metabolism for other cell types. In addition, further work will be needed to confirm these patterns of differential gene expression at the protein expression level, and to evaluate the functional role of the selected targets in the regulation of NP cell phenotype.

Conclusions

Data from the present study of the RNA transcriptome reveals an upregulation of individual notochordal markers and pathways associated with the notochord, cell differentiation, and stem cells in degenerate human NP cells upon interacting with a peptide-presenting PEG hydrogel. While some of the identified changes may be confirmed by prior studies of regulation of select molecular targets [Barcellona 2020], this study provides novel insights including the identification of GPCR-associated genes that point to novel pathways not well-studied in IVD development and disease. As with all studies of RNA transcriptome, additional studies are necessary for validating the expression and subcellular localization of the protein products of these genes. Overall, the present study provides insight into the global gene expression changes in degenerative cells cultured upon an engineered substrate, and the role of the substrate in promoting the assumption of a healthy phenotype.

REFERENCES

[1] J. C. Iatridis, L. A. Setton, M. Weidenbaum, V. C. Mow, Alterations in the mechanical behavior of the human lumbar nucleus pulposus with degeneration and aging, J. Orthop. Res. 15 (1997) 318-322. https://doi.org/10.1002/jor.1100150224.

[2] P. J. Roughley, Biology of Intervertebral Disc Aging and Degeneration, Spine (Phila. Pa. 1976). 29 (2004) 2691-2699. https://doi.org/10.1097/01.brs.0000146101.53784.b1.

[3] M. A. Adams, P. J. Roughley, What is intervertebral disc degeneration, and what causes it?, Spine (Phila. Pa. 1976). 31 (2006) 2151-2161. https://doi.org/10.1097/01.brs.0000231761.73859.2c.

[4] J. P. G. Urban, S. Roberts, Degeneration of the intervertebral disc, Arthritis Res. Ther. 5 (2003) 120-130. https://doi.org/10.1186/ar629.

[5] S. C. W. Chan, S. J. Ferguson, B. Gantenbein-Ritter, The effects of dynamic loading on the intervertebral disc, Eur. Spine J. 20 (2011) 1796-1812. https://doi.org/10.1007/s00586-011-1827-1.

[6] R. Tang, L. Jing, V. P. Willard, C. Wu, F. Guilak, J. Chen, L. A. Setton, Differentiation of human induced pluripotent stem cells into nucleus pulposus-like cells, Stem Cell Res. Ther. 9 (2018) 61. https://doi.org/10.1186/s13287-018-0797-1.

[7] J. C. Iatridis, M. Weidenbaum, L. A. Setton, V. C. Mow, Is the Nucleus Pulposus a Solid or a Fluid? Mechanical Behaviors of the Nucleus Pulposus of the Human Intervertebral Disc, Spine (Phila. Pa. 1976). 21 (1996) 1174-1184. https://doi.org/10.1097/00007632-199605150-00009.

[8] H. Choi, Z. I. Johnson, M. V Risbud, Understanding Nucleus Pulposus Cell Phenotype: A Prerequisite for Stem Cell Based Therapies to Treat Intervertebral Disc Degeneration, Curr. Stem Cell Res. Ther. 10 (2015) 307-316. https://doi.org/10.2174/1574888X10666150113112149.

[9] B. V Fearing, L. Jing, M. N. Barcellona, S. E. Witte, J. M. Buchowski, L. P. Zebala, M. P. Kelly, S. Luhmann, M. C. Gupta, A. Pathak, L. A. Setton, Mechanosensitive transcriptional coactivators MRTF-A and YAP/TAZ regulate nucleus pulposus cell phenotype through cell shape, FASEB J. 33 (2019) 14022-14035. https://doi.org/10.1096/fj.201802725RRR.

[10] J. M. Cloyd, N. R. Malhotra, L. Weng, W. Chen, R. L. Mauck, D. M. Elliott, Material properties in unconfined compression of human nucleus pulposus, injectable hyaluronic acid-based hydrogels and tissue engineering scaffolds, Eur. Spine J. 16 (2007) 1892-1898. https://doi.org/10.1007/s00586-007-0443-6.

[11] B. A. Walter, P. Mageswaran, X. Mo, D. J. Boulter, H. Mashaly, X. V Nguyen, L. M. Prevedello, W. Thoman, B. D. Raterman, P. Kalra, E. Mendel, W. S. Marras, A. Kolipaka, MR Elastography-derived Stiffness: A Biomarker for Intervertebral Disc Degeneration, Radiology. 285 (2017) 167-175. https://doi.org/10.1148/radiol.2017162287.

[12] M. V. Risbud, Z. R. Schoepflin, F. Mwale, R. A. Kandel, S. Grad, J. C. Iatridis, D. Sakai, J. A. Hoyland, Defining the phenotype of young healthy nucleus pulposus cells: Recommendations of the Spine Research Interest Group at the 2014 annual ORS meeting, J. Orthop. Res. 33 (2015) 283-293. https://doi.org/10.1002/jor.22789.

[13] J. Chen, L. Jing, C. Gilchrist, W. Richardson, R. Fitch, L. Setton, Expression of Laminin Isoforms, Receptors, and Binding Proteins Unique to Nucleus Pulposus Cells of Immature Intervertebral Disc, Connect. Tissue Res. 50 (2009) 294-306. https://doi.org/10.3109/03008200802714925.

[14] M. N. Barcellona, J. E. Speer, B. V Fearing, L. Jing, A. Pathak, M. C. Gupta, J. M. Buchowski, M Kelly, L. A. Setton, Control of adhesive ligand density for modulation of nucleus pulposus cell phenotype, Biomaterials. 250 (2020) 120057. https://doi.org/10.1016/j.biomaterials.2020.120057.

[15] N. Fujita, S. S. Gogate, K. Chiba, Y. Toyama, I. M. Shapiro, M. V. Risbud, Prolyl hydroxylase 3 (PHD3) modulates catabolic effects of tumor necrosis factor-α (TNF-α) on cells of the nucleus pulposus through co-activation of nuclear factor κB (NF-κB)/p65 signaling, J. Biol. Chem. 287 (2012) 39942-39953. https://doi.org/10.1074/jbc.M112.375964.

[16] Z. Liu, C. Li, X. Meng, Y. Bai, J. Qi, J. Wang, Q. Zhou, W. Zhang, X. Zhang, Hypoxia-inducible factor-Iα mediates aggrecan and collagen Π expression via NOTCH1 signaling in nucleus pulposus cells during intervertebral disc degeneration, Biochem. Biophys. Res. Commun. 488 (2017) 554-561. https://doi.org/10.1016/j.bbrc.2017.05.086.

[17] J. J. Trout, J. A. Buckwalter, K. C. Moore, S. K. Landas, Ultrastructure of the human intervertebral disc. I. Changes in notochordal cells with age, Tissue Cell. 14 (1982) 359-369. https://doi.org/10.1016/0040-8166 (82) 90033-7.

[18] A. T. Francisco, P. Y. Hwang, C. G. Jeong, L. Jing, J. Chen, L. A. Setton, Photocrosslinkable laminin-functionalized polyethylene glycol hydrogel for intervertebral disc regeneration, Acta Biomater. 10 (2014) 1102-1111. https://doi.org/10.1016/j.actbio.2013.11.013.

[19] D. T. Bridgen, B. V Fearing, L. Jing, J. Sanchez-Adams, M. C. Cohan, F. Guilak, J. Chen, L. A. Setton, Regulation of human nucleus pulposus cells by peptide-coupled substrates, Acta Biomater. 55 (2017) 100-108. https://doi.org/10.1016/j.actbio.2017.04.019.

[20] A. J. Engler, S. Sen, H. L. Sweeney, D. E. Discher, Matrix Elasticity Directs Stem Cell Lineage Specification, Cell. 126 (2006) 677-689. https://doi.org/10.1016/j.cell.2006.06.044.

[21] C.-M. Lo, H.-B. Wang, M. Dembo, Y. Wang, Cell Movement Is Guided by the Rigidity of the Substrate, Biophys. J. 79 (2000) 144-152. https://doi.org/10.1016/S0006-3495(00)76279-5.

[22] J. D. Humphrey, E. R. Dufresne, M. A. Schwartz, Mechanotransduction and extracellular matrix homeostasis, Nat. Rev. Mol. Cell Biol. 15 (2014) 802-812. https://doi.org/10.1038/nrm3896.

[23] N. Huebsch, Translational mechanobiology: Designing synthetic hydrogel matrices for improved in vitro models and cell-based therapies, Acta Biomater. 94 (2019) 97-111. https://doi.org/10.1016/j.actbio.2019.05.055.

[24] S. W. Crowder, V. Leonardo, T. Whittaker, P. Papathanasiou, M. M. Stevens, Material Cues as Potent Regulators of Epigenetics and Stem Cell Function, Cell Stem Cell. 18 (2016) 39-52. https://doi.org/10.1016/j.stem.2015.12.012.

[25] C. G. Jeong, A. T. Francisco, Z. Niu, R. L. Mancino, S. L. Craig, L. A. Setton, Screening of hyaluronic acid-poly (ethylene glycol) composite hydrogels to support intervertebral disc cell biosynthesis using artificial neural network analysis, Acta Biomater. 10 (2014) 3421-3430. https://doi.org/10.1016/j.actbio.2014.05.012.

[26] T. Tsujimoto, H. Sudo, M. Todoh, K. Yamada, K. Iwasaki, T. Ohnishi, N. Hirohama, T. Nonoyama, D. Ukeba, K. Ura, Y. M. Ito, N. Iwasaki, An acellular bioresorbable ultra-purified alginate gel promotes intervertebral disc repair: A preclinical proof-of-concept study, EBioMedicine. 37 (2018) 521-534. https://doi.org/10.1016/j.ebiom.2018.10.055.

[27] N. J. Darling, Y. S. Hung, S. Sharma, T. Segura, Controlling the kinetics of thiol-maleimide Michael-type addition gelation kinetics for the generation of homogenous poly(ethylene glycol) hydrogels, Biomaterials. 101 (2016) 199-206. https://doi.org/10.1016/j.biomaterials.2016.05.053.

[28] B. V Fearing, J. E. Speer, L. Jing, A. Kalathil, M. P. Kelly, J. M. Buchowski, L. P. Zebala, S. Luhmann, M. C. Gupta, L. A. Setton, Verteporfin treatment controls morphology, phenotype, and global gene expression for cells of the human nucleus pulposus, JOR Spine. (2020) e1111. https://doi.org/10.1002/jsp2.1111.

[29] R. McBeath, D. M. Pirone, C. M. Nelson, K. Bhadriraju, C. S. Chen, Cell Shape, Cytoskeletal Tension, and RhoA Regulate Stem Cell Lineage Commitment, Dev. Cell. 6 (2004) 483-495. https://doi.org/10.1016/S1534-5807(04)00075-9.

[30] L. Gao, R. McBeath, C. S. Chen, Stem Cell Shape Regulates a Chondrogenic Versus Myogenic Fate Through Rac1 and N-Cadherin, Stem Cells. 28 (2010) 564-572. https://doi.org/10.1002/stem.308.

[31] J. Lee, A. A. Abdeen, D. Zhang, K. A. Kilian, Directing stem cell fate on hydrogel substrates by controlling cell geometry, matrix mechanics and adhesion ligand composition, Biomaterials. 34 (2013) 8140-8148. https://doi.org/10.1016/j.biomaterials.2013.07.074.

[32] C. L. Gilchrist, E. M. Darling, J. Chen, L. A. Setton, Extracellular Matrix Ligand and Stiffness Modulate Immature Nucleus Pulposus Cell-Cell Interactions, PLOS One. 6 (2011) e27170. https://doi.org/10.1371/journal.pone.0027170.

[33] B. L. Bangasser, G. A. Shamsan, C. E. Chan, K. N. Opoku, E. Tüzel, B. W. Schlichtmann, J. A. Kasim, B. J. Fuller, B. R. Mccullough, S. S. Rosenfeld, D. J. Odde, Shifting the optimal stiffness for cell migration, Nat. Commun. 8 (2017) 15313. https://doi.org/10.1038/ncomms15313.

[34] K. A. Kilian, M. Mrksich, Directing stem cell fate by controlling the affinity and density of ligand-receptor interactions at the biomaterials interface, Angew. Chemie—Int. Ed. 51 (2012) 4891-4895. https://doi.org/10.1002/anie.201108746.

[35] K. A. Kilian, B. Bugarija, B. T. Lahn, M. Mrksich, Geometric cues for directing the differentiation of mesenchymal stem cells, Proc. Natl. Acad. Sci. 107 (2010) 4872-4877. https://doi.org/10.1073/pnas.0903269107.

[36] A. Mitra, S. Venkatachalapathy, P. Ratna, Y. Wang, D. S. Jokhun, G. V. Shivashankar, Cell geometry dictates TNFα-induced genome response, Proc. Natl. Acad. Sci. 114 (2017) E3882-E3891. https://doi.org/10.1073/pnas.1618007114.

[37] S. Riquier, M. Mathieu, A. Boureux, F. Ruffle, J. LeMaitre, F. Djouad, N. Gilbert, T. Commes, Detailed analysis of public RNAseq data and longnon-coding RNA: a proposed enhancement to mesenchymal stem cell characterisation, BioRxiv Genomics. (2020). https://doi.org/10.1101/2020.03.09.976001.

[38] M. Barik, P. R. Mishra, A. K. Mohapatra, Missing Links Between Genetically Inherited Molecules in Split Cord Malformation and Other Anomaly: A Bench to Bedside Approach, J. Pediatr. Neurosci. 13 (2018) 46-57. https://doi.org/10.4103/JPN.JPN_124_17.

[39] Y. Zhang, Z. Zhang, P. Chen, C. Y. Ma, C. Li, T. Y. K. Au, V. Tam, Y. Peng, R. Wu, K. M. C. Cheung, P. C. Sham, H. Tse, D. Chan, V. Y. Leung, K. S. E. Cheah, Q. Lian, Directed Differentiation of Notochord-like and Nucleus Pulposus-like Cells Using Human Pluripotent Stem Cells, Cell Rep. 30 (2020) 2791-2806.e5. https://doi.org/10.1016/j.celrep.2020.01.100.

[40] P. Sohn, M. Cox, D. Chen, R. Serra, Molecular profiling of the developing mouse axial skeleton: a role for Tgfbr2 in the development of the intervertebral disc, BMC Dev. Biol. 10 (2010) 29. https://doi.org/10.1186/1471-213X-10-29.

[41] G. Pattappa, Z. Li, M. Peroglio, N. Wismer, M. Alini, S. Grad, Diversity of intervertebral disc cells: phenotype and function, J. Anat. 221 (2012) 480-496. https://doi.org/10.1111/j.1469-7580.2012.01521.x.

[42] L. Aker, M. Ghannam, M. A. Alzuabi, F. Jumah, S. M. Alkhdour, S. Mansour, A. Samara, K. Cronk, J. Massengale, J. Holsapple, N. Adeeb, R. J. Oskouian, R. S. Tubbs, Molecular Biology and Interactions in Intervertebral Disc Development, Homeostasis, and Degeneration, with Emphasis on Future Therapies: A Systematic Review, Spine Sch. 1 (2017) 2-20. https://doi.org/10.26632/ss.3.2017.1.1.

[43] X.-H. Bai, H.-R. Cho, S. Moodley, M. Liu, XB130-A Novel Adaptor Protein: Gene, Function, and Roles in Tumorigenesis, Scientifica (Cairo). 2014 (2014) 1-9. https://doi.org/10.1155/2014/903014.

[44] Y. Cui, Interplay of the osmotic environment and a fibronectin fragment in intervertebral disc cell metabolism, University of Oxford, 2011.

[45] T. Kim, K. Kim, S. H. Lee, H.-S. So, J. Lee, N. Kim, Y. Choi, Identification of LRRc17 as a Negative Regulator of Receptor Activator of NF-κB Ligand (RANKL)-induced Osteoclast Differentiation, J. Biol. Chem. 284 (2009) 15308-15316. https://doi.org/10.1074/jbc.M807722200.

[46] G. F. Mok, L. Folkes, S. Weldon, E. Maniou, V. Martinez-Heredia, A. Godden, R. Williams, G. N. Wheeler, S. Moxon, A. Munsterberg, Characterising open chromatin identifies novel cis-regulatory elements impor-

[47] M. Nguyen, P. Singhal, J. W. Piet, S. J. Shefelbine, M. Maden, S. R. Voss, J. R. Monaghan, Retinoic acid receptor regulation of epimorphic and homeostatic regeneration in the axolotl, Development. 144 (2017) 601-611. https://doi.org/10.1242/dev.139873.

[48] T. Tondreau, M. Dejeneffe, N. Meuleman, B. Stamatopoulos, A. Delforge, P. Martiat, D. Bron, L. Lagneaux, Gene expression pattern of functional neuronal cells derived from human bone marrow mesenchymal stromal cells, BMC Genomics. 9 (2008) 166. https://doi.org/10.1186/1471-2164-9-166.

[49] J.-H. Jang, J.-Y. Park, J.-Y. Oh, S.-J. Bae, H. Jang, S. Jeon, J. Kim, H.-J. Park, Novel analgesic effects of melanin-concentrating hormone on persistent neuropathic and inflammatory pain in mice, Sci. Rep. 8 (2018) 707. https://doi.org/10.1038/s41598-018-19145-z.

[50] A. D. Rouillard, G. W. Gundersen, N. F. Fernandez, Z. Wang, C. D. Monteiro, M. G. McDermott, A. Ma'ayan, The harmonizome: a collection of processed datasets gathered to serve and mine knowledge about genes and proteins, Database. 2016 (2016) 1-16. https://doi.org/10.1093/database/baw100.

[51] K. Zandi-Nejad, A. Takakura, M. Jurewicz, A. K. Chandraker, S. Offermanns, D. Mount, R. Abdi, The role of HCA2 (GPR109A) in regulating macrophage function, FASEB J. 27 (2013) 4366-4374. https://doi.org/10.1096/fj. 12-223933.

[52] T. Satoh, S. Lipton, Recent advances in understanding NRF2 as a druggable target: development of pro-electrophilic and non-covalent NRF2 activators to overcome systemic side effects of electrophilic drugs like dimethyl fumarate, F1000Research. 6 (2017) 2138. https://doi.org/10.12688/f1000research. 12111.1.

[53] M. Uhlen, L. Fagerberg, B. M. Hallstrom, C. Lindskog, P. Oksvold, A. Mardinoglu, A. Sivertsson, C. Kampf, E. Sjostedt, A. Asplund, I. Olsson, K. Edlund, E. Lundberg, S. Navani, C. A.-K. Szigyarto, J. Odeberg, D. Djureinovic, J. O. Takanen, S. Hober, T. Alm, P.-H. Edqvist, H. Berling, H. Tegel, J. Mulder, J. Rockberg, P. Nilsson, J. M. Schwenk, M. Hamsten, K. von Feilitzen, M. Forsberg, L. Persson, F. Johansson, M. Zwahlen, G. von Heijne, J. Nielsen, F. Ponten, Tissue-based map of the human proteome, Science (80-.). 347 (2015) 1260419-1260419. https://doi.org/10.1126/science. 1260419.

[54] K. Zorina-Lichtenwalter, C. B. Meloto, S. Khoury, L. Diatchenko, Genetic predictors of human chronic pain conditions, Neuroscience. 338 (2016) 36-62. https://doi.org/10.1016/j.neuroscience.2016.04.041.

[55] C. Zhao, X. Quan, J. He, R. Zhao, Y. Zhang, X. Li, S. Sun, R. Ma, Q. Zhang, Identification of significant gene biomarkers of low back pain caused by changes in the osmotic pressure of nucleus pulposus cells, Sci. Rep. 10 (2020) 3708. https://doi.org/10.1038/s41598-020-60714-y.

[56] D. Kringel, C. Lippmann, M. J. Parnham, E. Kalso, A. Ultsch, J. Lötsch, A machine-learned analysis of human gene polymorphisms modulating persisting pain points to major roles of neuroimmune processes, Eur. J. Pain. 22 (2018) 1735-1756. https://doi.org/10.1002/ejp.1270.

[57] S. Speichert, N. Molotkov, K. El Bagdadi, A. Meurer, F. Zaucke, Z. Jenei-Lanzl, Role of Norepinephrine in IL-1β-Induced Chondrocyte Dedifferentiation under Physioxia, Int. J. Mol. Sci. 20 (2019) 1212. https://doi.org/10.3390/ijms20051212.

[58] J. Kupka, A. Kohler, K. El Bagdadi, R. Bostelmann, M. Brenneis, C. Fleege, D. Chan, F. Zaucke, A. Meurer, M. Rickert, Z. Jenei-Lanzl, Adrenoceptor Expression during Intervertebral Disc Degeneration, Int. J. Mol. Sci. 21 (2020) 2085. https://doi.org/10.3390/ijms21062085.

[59] M. S. Hossain, K. Mineno, T. Katafuchi, Neuronal Orphan G-Protein Coupled Receptor Proteins Mediate Plasmalogens-Induced Activation of ERK and Akt Signaling, PLOS One. 11 (2016) e0150846. https://doi.org/10.1371/journal.pone.0150846.

[60] G. G. H. van den Akker, L. M. T. Eijssen, S. M. Richardson, L. W. van Rhijn, J. A. Hoyland, T. J. M. Welting, J. W. Voncken, A Membranome-Centered Approach Defines Novel Biomarkers for Cellular Subtypes in the Intervertebral Disc, Cartilage. 11 (2020) 203-220. https://doi.org/10.1177/1947603518764260.

[61] C. Southern, J. M. Cook, Z. Neetoo-Isseljee, D. L. Taylor, C. A. Kettleborough, A. Merritt, D. L. Bassoni, W. J. Raab, E. Quinn, T. S. Wehrman, A. P. Davenport, A. J. Brown, A. Green, M. J. Wigglesworth, S. Rees, Screening β-Arrestin Recruitment for the Identification of Natural Ligands for Orphan G-Protein-Coupled Receptors, J. Biomol. Screen. 18 (2013) 599-609. https://doi.org/10.1177/1087057113475480.

[62] D. Szklarczyk, A. L. Gable, D. Lyon, A. Junge, S. Wyder, J. Huerta-Cepas, M. Simonovic, N. T. Doncheva, J. H. Morris, P. Bork, L. J. Jensen, C. von Mering, STRING v11: protein-protein association networks with increased coverage, supporting functional discovery in genome-wide experimental datasets, Nucleic Acids Res. 47 (2019) D607-D613. https://doi.org/10.1093/nar/gky1131.

[63] T. J. Yuen, K. R. Johnson, V. E. Miron, C. Zhao, J. Quandt, M. C. Harrisingh, M. Swire, A. Williams, H. F. McFarland, R. J. M. Franklin, C. Ffrench-Constant, Identification of endothelin 2 as an inflammatory factor that promotes central nervous system remyelination, Brain. 136 (2013) 1035-1047. https://doi.org/10.1093/brain/awt024.

[64] A. Rattner, H. Yu, J. Williams, P. M. Smallwood, J. Nathans, Endothelin-2 signaling in the neural retina promotes the endothelial tip cell state and inhibits angiogenesis, Proc. Natl. Acad. Sci. 110 (2013) E3830-E3839. https://doi.org/10.1073/pnas.1315509110.

[65] R. Rodrigues-Pinto, L. Ward, M. Humphreys, L. A. H. Zeef, A. Berry, K. P. Hanley, N. Hanley, S. M. Richardson, J. A. Hoyland, Human notochordal cell transcriptome unveils potential regulators of cell function in the developing intervertebral disc, Sci. Rep. 8 (2018) 12866. https://doi.org/10.1038/s41598-018-31172-4.

[66] S. Williams, B. Alkhatib, R. Serra, Development of the axial skeleton and intervertebral disc, in: Curr. Top. Dev. Biol., 1st ed., Elsevier Inc., 2019: pp. 49-90. https://doi.org/10.1016/bs.ctdb.2018.11.018.

[67] T. Iwamoto, H. Okamoto, N. Iikuni, M. Takeuchi, Y. Toyama, T. Tomatsu, N. Kamatani, S. Momohara, Monocyte chemoattractant protein-4 (MCP-4)/CCL13 is highly expressed in cartilage from patients with rheumatoid arthritis, Rheumatology. 45 (2006) 421-424. https://doi.org/10.1093/rheumatology/kei209.

[68] S. Sozzani, A. Del Prete, R. Bonecchi, M. Locati, Chemokines as effector and target molecules in vascular biology, Cardiovasc. Res. 107 (2015) 364-372. https://doi.org/10.1093/cvr/cvv150.

[69] G. Diez-Roux, S. Banfi, M. Sultan, L. Geffers, S. Anand, D. Rozado, A. Magen, E. Canidio, M. Pagani, I. Peluso, N. Lin-Marq, M. Koch, M. Bilio, I. Cantiello, R.

Verde, C. De Masi, S. A. Bianchi, J. Cicchini, E. Perroud, S. Mehmeti, E. Dagand, S. Schrinner, A. Nürnberger, K. Schmidt, K. Metz, C. Zwingmann, N. Brieske, C. Springer, A. M. Hernandez, S. Herzog, F. Grabbe, C. Sieverding, B. Fischer, K. Schrader, M. Brockmeyer, S. Dettmer, C. Helbig, V. Alunni, M.-A. Battaini, C. Mura, C. N. Henrichsen, R. Garcia-Lopez, D. Echevarria, E. Puelles, E. Garcia-Calero, S. Kruse, M. Uhr, C. Kauck, G. Feng, N. Milyaev, C. K. Ong, L. Kumar, M. Lam, C. A. Semple, A. Gyenesei, S. Mundlos, U. Radelof, H. Lehrach, P. Sarmientos, A. Reymond, D. R. Davidson, P. Dolle, S. E. Antonarakis, M.-L. Yaspo, S. Martinez, R. A. Baldock, G. Eichele, A. Ballabio, A High-Resolution Anatomical Atlas of the Transcriptome in the Mouse Embryo, PLOS Biol. 9 (2011) e1000582. https://doi.org/10.1371/journal.pbio. 1000582.

[70] C. J. Bult, J. A. Blake, C. L. Smith, J. A. Kadin, J. E. Richardson, A. Anagnostopoulos, R. Asabor, R. M. Baldarelli, J. S. Beal, S. M. Bello, O. Blodgett, N. E. Butler, K. R. Christie, L. E. Corbani, J. Creelman, M. E. Dolan, H. J. Drabkin, S. L. Giannatto, P. Hale, D. P. Hill, M. Law, A. Mendoza, M. McAndrews, D. Miers, H. Motenko, L. Ni, H. Onda, M. Perry, J. M. Recla, B. Richards-Smith, D. Sitnikov, M. Tomczuk, G. Tonorio, L. Wilming, Y. Zhu, Mouse Genome Database (MGD) 2019, Nucleic Acids Res. 47 (2019) D801-D806. https://doi.org/10.1093/nar/gky1056.

[71] C. E. Hughes, R. J. B. Nibbs, A guide to chemokines and their receptors, FEBS J. 285 (2018) 2944-2971. https://doi.org/10.1111/febs. 14466.

[72] J. Li, L. Xiang, X. Jiang, B. Teng, Y. Sun, G. Chen, J. Chen, J. V. Zhang, P.-G. Ren, Investigation of bioeffects of G protein-coupled receptor 1 on bone turnover in male mice, J. Orthop. Transl. 10 (2017) 42-51. https://doi.org/10.1016/j.jot.2017.05.001.

[73] J. Luo, P. Sun, S. Siwko, M. Liu, J. Xiao, The role of GPCRs in bone diseases and dysfunctions, Bone Res. 7 (2019) 19. https://doi.org/10.1038/s41413-019-0059-6.

[74] H. Eleftherohorinou, C. J. Hoggart, V. J. Wright, M. Levin, L. J. M. Coin, Pathway-driven gene stability selection of two rheumatoid arthritis GWAS identifies and validates new susceptibility genes in receptor mediated signalling pathways, Hum. Mol. Genet. 20 (2011) 3494-3506. https://doi.org/10.1093/hmg/ddr248.

[75] R. Alonso, M. C. Rodríguez, J. Pindado, E. Merino, I. Mérida, M. Izquierdo, Diacylglycerol Kinase α Regulates the Secretion of Lethal Exosomes Bearing Fas Ligand during Activation-induced Cell Death of T Lymphocytes, J. Biol. Chem. 280 (2005) 28439-28450. https://doi.org/10.1074/jbc.M501112200.

[76] E. Budd, MicroRNAs in Osteoarthritis and Chondrogenesis, University of Southampton; Institute of Developmental Health, 2016. https://eprints.soton.ac.uk/407447/1/Emma_Budd_PhD_THESIS_08_09_2016_MicrORNAs_in_O A_Chondrogenesis_Pdf.pdf.

[77] S. A. Ali, Hedgehog Signaling Modulates Cholesterol Homeostasis in Chondrocytes and in Osteoarthritis, University of Toronto, 2014. http://hdl.handle.net/1807/74488% 0A %0A.

[78] Z. I. Johnson, A. C. Doolittle, J. W. Snuggs, I. M. Shapiro, C. L. Le Maitre, M. V. Risbud, TNF-α promotes nuclear enrichment of the transcription factor TonEBP/NFAT5 to selectively control inflammatory but not osmoregulatory responses in nucleus pulposus cells, J. Biol. Chem. 292 (2017) 17561-17575. https://doi.org/10.1074/jbc.M117.790378.

[79] S. Koyanagi, N. Kusunose, M. Taniguchi, T. Akamine, Y. Kanado, Y. Ozono, T. Masuda, Y. Kohro, N. Matsunaga, M. Tsuda, M. W. Salter, K. Inoue, S. Ohdo, Glucocorticoid regulation of ATP release from spinal astrocytes underlies diurnal exacerbation of neuropathic mechanical allodynia, Nat. Commun. 7 (2016) 13102. https://doi.org/10.1038/ncomms13102.

[80] G. Giannattasio, S. Ohta, J. R. Boyce, W. Xing, B. Balestrieri, J. A. Boyce, The Purinergic G Protein-Coupled Receptor 6 Inhibits Effector T Cell Activation in Allergic Pulmonary Inflammation, J. Immunol. 187 (2011) 1486-1495. https://doi.org/10.4049/jimmunol.1003669.

[81] J. Jing, L. Chen, H.-Y. Fu, K. Fan, Q. Yao, Y.-F. Ge, J.-C. Lu, B. Yao, Annexin V-induced rat Leydig cell proliferation involves Ect2 via RhoA/ROCK signaling pathway, Sci. Rep. 5 (2015) 9437. https://doi.org/10.1038/srep09437.

[82] Z. Chen, J. Liu, Y. Zhang, Role of Epithelial Cell Transforming Sequence 2 (ECT2) in Predicting Prognosis of Osteosarcoma, Med. Sci. Monit. 23 (2017) 3861-3868. https://doi.org/10.12659/MSM.905951.

[83] Y. Wu, T. Wu, B. Xu, X. Xu, H. Chen, X. Li, Oxytocin prevents cartilage matrix destruction via regulating matrix metalloproteinases, Biochem. Biophys. Res. Commun. 486 (2017) 601-606. https://doi.org/10.1016/j.bbrc.2017.02.115.

[84] Y. Wang, L. Jiang, G. Dai, S. Li, X. Mu, Bioinformatics analysis reveals different gene expression patterns in the annulus fibrosis and nucleus pulpous during intervertebral disc degeneration, Exp. Ther. Med. 16 (2018) 5031-5040. https://doi.org/10.3892/etm.2018.6884.

[85] K. T. Leblanc, Runx Expression in Normal and Osteoarthritic Cartilage: Possible Functions of Runx Proteins in Chondrocytes: A Dissertation, University of Massachusetts Medical School, 2013. https://doi.org/10.13028/M23C7H.

[86] N. A. Tenn, Investigating The Mechanism Of Ectopic Mineralization In A Mouse Model Of Diffuse Idiopathic Skeletal Hyperostosis (DISH), The University of Western Ontario, 2015. https://ir.lib.uwo.ca/etd/2966.

[87] P. Y. Hwang, L. Jing, J. Chen, F.-L. Lim, R. Tang, H. Choi, K. M. Cheung, M. V Risbud, C. A. Gersbach, F. Guilak, V. Y. Leung, L. A. Setton, N-cadherin is Key to Expression of the Nucleus type under Selective Substrate Culture Conditions, Sci. Rep. 6 (2016) 28038.

Example 7: In Situ Crosslinked Cell-Laden Hydrogel Delivery into the Intradiscal Space This example describes the methods and results for a 3D cell culture, as well as the in vivo delivery of the material into a rat model of disc degeneration for recovery and maintenance of the healthy NP phenotype.

Abstract

The intervertebral disc (IVD) has been widely observed to undergo significant phenotypic and metabolic changes with age and maturation. Although the origins of disc degeneration remain a topic for debate, it is believed that the nucleus pulposus (NP) region of the IVD is implicated in early degeneration events. Our lab has previously demonstrated an ability to promote adult degenerative NP cells to undergo a shift from a degenerative fibroblast-like state to a juvenile-like NP phenotype through culture upon substrates with specific biomechanical and molecular cues. In the current study, we seek to utilize a peptide-functionalized hydrogel scaffold as a bioactive system (e.g., capable of delivering and supporting cells or cells secreting factors, such as cytokines or other factors that promote cell attachment, matrix degrading protease mediating factors, inflammatory mediating factors, or others) for cell delivery and retention in a rat caudal model of disc degeneration via anular puncture. Our data suggest that 3D constructs made from a stiff hydrogel functionalized with laminin-mimetic peptides at 100 µM promote cell viability and increased biosynthetic activity for adult degenerative NP cells in vitro. Delivery of the cell-laden biomaterial in vivo supported NP cell retention and protein expression, and promoted improved disc height index (DHI) values as well as improved endplate organization.

Introduction

The nucleus pulposus (NP) of the intervertebral disc (IVD) has been observed to undergo significant biological, physical, and biochemical changes with aging, maturation, trauma, and other factors. Although the origins of disc degeneration remain largely misunderstood, these changes are thought to be implicated with degenerative events[1-7]. As disc degeneration progresses, changes in matrix composition and tissue cellularity have been reported[6,8-12]. Loss of glycosaminoglycans, progressive changes in extracellular matrix composition (e.g. decreased expression of collagen type 2 and increases in collagen type 1), and altered biosynthetic activity all play a role in tissue degeneration, often leading to structural issues at longer length scales such as disc dehydration, tissue stiffening, loss of disc height, and ultimately altered biomechanics[2,3,13-15].

Because the disc has inherently little capacity for self-repair due to low vascularization and nutrient supply, various strategies have been investigated towards the goal of disc height restoration, nucleus pulposus tissue repair, and overall disc regeneration[16-22]. A number of acellular materials-based approaches have been developed with the goal of providing mechanical support to the spine and/or stimulating the resident NP cells to alter protein expression, metabolic activity, or cytokine release profiles[16,23-25]. Although these strategies are attractive due to the lack of a cellular component, acellular techniques rely on an interaction between the residing NP cells and the hydrogel for promoting tissue integration and biosynthetic activity[23]. This may be problematic, as the NP has a low cell density in the healthy state, which is further exacerbated with degeneration[21,26]. Alternatively, cell delivery approaches seek to treat degeneration by supplying an active cell population into the intradiscal space[27-29]. While effective at promoting an increase in biosynthetic activity, these approaches often fail to provide biological and molecular cues necessary for the maintenance of cell phenotype following delivery. Furthermore, cell leakage due to the lack of a carrier has been reported to have off-target effects such as osteophyte formation near the endplates following MSC delivery into a degenerated disc[27]. Cell-laden materials have arguably been the most successful in terms of tissue reintegration as they not only provide a cell source for the re-cellularization of the NP, but also a material scaffold for cell delivery, localization, retention, and promotion of biosynthetic activity.

In previous work, we developed a peptide-functionalized poly(ethylene glycol) (PEG)-based hydrogel system of similar stiffness to the degenerative NP (15% PEG w/v, ~10 kPa; functionalized with the laminin-mimetic peptides AG73 and IKVAV)[30]. This system was benchmarked against a soft hydrogel functionalized with full length laminin-111 protein (4% PEG w/v, ~500 Pa-physiological stiffness for the healthy NP) which has been extensively characterized and shown to shift human adult degenerative NP cells towards behaviors consistent with a juvenile state[30-33]. Our data suggested that by using a peptide density that inhibited focal adhesion formation and promoted cells to assume a rounded, clustered morphology, cells cultured in 2D on the stiff-low peptide density-functionalized system demonstrated similar degrees of bioactivity, gene expression, and protein deposition as to cells cultured atop the soft, full-length-laminin functionalized hydrogel[8,30,32]. In the present study, we sought to examine the potential for the stiff-low peptide density hydrogel to be used as a 3D cell encapsulation system in vitro. We further evaluate the ability of this platform to restore parameters of the healthy juvenile disc following in vivo delivery into rat caudal discs following degeneration induced via a surgical puncture model[29,34-39]. The results suggest that the stiff-low peptide-functionalized gel promoted similar levels of bioactivity as the soft PEG-LM positive control during 3D in vitro culture. The cells delivered to the discs via the peptide-functionalized hydrogel remained viable for 8-weeks following injection and demonstrated biosynthetic activity. Furthermore, implantation of the cell-laden peptide-functionalized hydrogels into the degenerative disc space showed reduced degeneration as quantified through disc height indices and decreased degeneration-induced alterations to the endplates.

Methods

NP Cell Isolation

For in vitro cell culture experiments, primary adult human NP cells (n≥3 human samples, both sexes, ages 30-68) were isolated as previously described[30,40] Briefly, to-be-discarded tissue from patients undergoing surgical intervention for degeneration-associated complications was collected (IRB exempt per the Washington University Institutional Review Board). NP tissue was identified and digested for 2-4 hours at 37° C. and 5% $CO_2$ in digestion medium containing 0.4% type 2 collagenase (Worthington Biochemical, Lakewood, NK) and 0.2% pronase (Roche, Basel, Switzerland). The digest was ended when cells could be individually identified under a microscope. Following, the digestion medium was centrifuged for 10 minutes at 400 rcf to pellet the cells, and the medium was aspirated. Cells were resuspended in PBS and then passed through a 70 µm filter. The flowthrough was again centrifuged for 10 minutes at 400 rcf, and the resulting cell pellet was resuspended in Ham's F12 medium (Thermo Fisher Scientific, Waltham, MA), supplemented with 10% fetal bovine serum (FBS) and 1% penicillin-streptomycin (P/S) and cultured in monolayer. Cells were always used between passages 1 and 4.

In contrast, rat NP cells were used for in vivo delivery of cell-laden constructs into the rat IVD. First, 8 caudal discs from each of 8 male Sprague-Dawley rats (16-20 weeks old) were isolated immediately following sacrifice. Discs were bisected using a size 11 surgical blade, and the gelatinous NP tissue was extracted. Rat NP cells were then isolated by placing the tissue in digestion medium containing 0.2% type 2 collagenase (Worthington Biochemical, Lakewood, NK) and 0.3% pronase (Roche, Basel, Switzerland) for 2-4 hours at 37° C. and 5% $CO_2$. The digestion medium was then centrifuged for 10 minutes at 400 rcf, the pelleted cells were resuspended in PBS and passed through a 70 µm filter, and the flowthrough was again spun down for 10 minutes at 400 rcf. The resulting cell pellet was resuspended in Ham's F12 medium (Thermo Fisher Scientific, Waltham, MA), supplemented with 10% fetal bovine serum (FBS) and 1% penicillin-streptomycin (P/S) and cultured in monolayer. Rat NP cells were used between passages 1 and 4.

Hydrogel Preparation and In Vitro 3D NP Cell Culture

Maleimide terminated 8-arm star poly(ethylene glycol) (PEG-8MAL, MW 20K, Creative PEGWorks, Durham, NC) was first dissolved in Ham's F12 cell culture media supplemented with 1% P/S. Lyophilized, cysteine terminated IKVAV and AG73 peptides (full sequences for IKVAV and AG73: CSRARKQAASIKVAVSADR (C terminated SEQ ID NO: 2), and CGGRKRLQVQLSIRT (CGG-terminated SEQ ID NO: 1) respectively, GenScript, Piscataway, NJ) were likewise dissolved in F12+1% P/S. A maleimide-thiol Michael-type addition reaction was employed both for peptide conjugation and hydrogel formation. Peptide solution was added to the PEG-8MAL in order to pre-conjugate peptides to the PEG-8MAL backbone. A small PEG-dithiol (SH-PEG-SH, MW 600, Creative PEGWorks, Durham, NC) crosslinker was dissolved in F12+20% FBS+1% P/S. Primary degenerative adult human NP cells were then suspended in the PEG-dithiol solution at a density of $2.5 \times 10^6$ cell/mL. The cell-containing di-thiol crosslinker mix was then added to the peptide-functionalized maleimide in wells of a round-bottom 96 well plate to initiate hydrogel formation. This yielded our cell-laden stiff peptide-functionalized construct (15% PEG w/v, 100 µM total peptide using equimolar amounts of IKVAV+AG73, modulus ~10 kPa) 30. Constructs were cultured at 37° C. and 5% $CO_2$ for 4 days.

Cell Viability, Biosynthetic Activity, and Matrix Deposition

Following 3D in vitro cell culture of NP, cell viability was surveyed using a live/dead viability kit following manufacturer recommendations (Invitrogen, Carlsbad, CA). To assay biosynthetic activity and matrix deposition, a functional noncanonical amino-acid tagging approach was employed[41]. Briefly, 3D cell-containing hydrogels were made as described above and cultured in L-methionine free DMEM (Gibco, ThermoFisher, Waltham, MA) supplemented with L-azidohomoalanine (AHA, ClickChemistryTools, Scottsdale, AZ). Cells were cultured for 4 days at 37° C. and 5% $CO_2$. After 4 days, the media was replaced with L-methionine free DMEM supplemented with 30 µM of the AHA-binding secondary DBCO-488 (ClickChemistryTools, Scottsdale, AZ), and incubated for 45 minutes at 37° C. and 5% $CO_2$. The constructs were then washed with PBS 3 times and fixed for 12 minutes using 4% PFA. Following, cells were stained with Alexa-conjugated phalloidin 633 (1:250, Invitrogen) to visualize cell bodies, and counterstained with DAPI (2 µg/mL, Sigma-Aldrich, St. Louis, MO) to visualize nuclei. Overlaying the phalloidin channel with the AHA channel allowed for the measurement of intracellular AHA presence, which was used as a measure of biosynthetic activity. Extracellular AHA presence was used as a measure of matrix deposition and was calculated as $$\frac{\text{Volume}_{Matrix} - \text{Volume}_{Cell}}{\text{Volume}_{Cell}}.$$

Actin fiber alignment was quantified using the OrientationJ plugin in Fiji, where an output of one indicates strong fiber alignment, and an output of zero indicates anisotropic fiber orientation.

Immunocytochemistry 3D cell-laden hydrogel constructs were immunostained with markers selected following recommendations from the Spine Research Interest Group as published in a 2015 consensus paper[42]. Following culture, whole constructs were fixed in 4% PFA for 12 minutes, rinsed with 1×PBS (+Ca, +Mg) twice for 10 minutes each, and permeabilized with 0.2% TritonX-100 (Sigma-Aldrich, St. Louis, MO). Constructs were blocked with 3.75% bovine serum albumin (MilliporeSigma) and 5% goat serum (Thermo Fisher Scientific), and immunolabeled with mouse-anti-N-Cadherin (1:150, Sigma-Aldrich), rabbit-anti-BASP1 (1:150, Abcam, Cambridge, United Kingdom), goat-anti-noggin (1:150, Santa Cruz Biotechnology, Dallas, TX), or Alexa-conjugated phalloidin (1:250, Invitrogen). The proper isotype controls were used for each antibody. Species-matched AlexaFluor™ (Invitrogen) secondary antibodies were applied using a dilution of 1:250, and cells were counterstained with DAPI (2 µg/mL, Sigma-Aldrich).

Gene Expression

Gene expression was assayed using qPCR on an Applied Biosystems™ StepOnePlus™ Real-Time PCR System (Software v2.3, Foster City, CA). As above, markers were selected following the recommendations described in the 2015 consensus paper[42]. Briefly, 3D cell laden-scaffolds containing $2.5 \times 10^6$ cells/mL primary adult human NP cells were homogenized using RLT buffer (Qiagen, Hilden, Germany)+1% mercaptoethanol in a BioSpec Mini-Beadbeater-24 bead beater (BioSpec, Bartlesville, OK) at 3000 rpm using 2 mm diameter zirconia beads (BioSpec, Bartlesville, OK), and stored at −80° C. until ready for RNA isolation. RNA was isolated using the QIAGEN™ Mini kit following manufacturer instructions (Giagen, Hilden, Germany). RNA concentration and purity were determined using the 260/280 ratio quantified via a NanoDrop™ system (ThermoFisher Scientific, Waltham, MA). RNA was converted to cDNA using the iScript cDNA Synthesis Kit (BioRad, Hercules, CA). RT-qPCR was used to detect amplification of aggrecan (ACAN), collagen 2 (COL2A1), N-Cadherin (CDH2), glucose transporter 1 (GLUT1), connective tissue growth factor (CTGF), brain associated soluble protein 1 (BASP1), integrin α6 (ITGa6), and collagen I (COL1A1) (TABLE 4, Applied Biosystems) using the ΔΔCt method, with the first Δ being normalization of the gene to housekeeping genes 18S and GAPDH, and the second Δ being normalization to the soft PEG-LM positive control[8,31,32].

TABLE 4

Primers used for RT-qPCR study of 3D adult human NP cell encapsulation.

| Primer Probe | Common Name | Applied Biosystems No. |
|---|---|---|
| ACAN | Aggrecan (AGC) | Hs00153936_m1 |
| COL2A1 | Collagen type II | Hs00156568_m1 |
| CDH2 | N-Cadherin | Hs00983056_m1 |
| SLC2A1 | Glucose transporter 1 (GLUT1) | Hs00892681_m1 |
| CTGF | Connective tissue growth factor | Hs00170014_m1 |
| BASP1 | Brain acid soluble protein 1 | Hs00932356_s1 |
| ITGa6 | Integrin a6 | Hs00173952_m1 |
| COL1A1 | Collagen type 1 | Hs00164004_m1 |
| GAPDH | Housekeeping gene | 4332649 |
| 18S | Housekeeping gene | Hs99999901_s1 |

Reporter Cell for In Vivo Tracking

For tracking cell viability and retention following in vivo delivery, rat NP cells were isolated from multiple levels of 8 Sprague-Dawley rat caudal intervertebral discs. Cells were passaged once and expanded to ensure adequate cell numbers. Following, cells were plated at a density of 500,000 cells/well in wells of a 6 well plate in 2 mL transduction media containing 10% FB, 4 µg/mL polybrene (hexadimethrine bromide, Sigma Aldrich, St. Louis, MO), and 4 µL of the concentrated lentiviral plasmid (titer $5.5 \times 10^8$) containing a luciferase reporter upstream of the constitutive EF1 promoter (Addgene, Watertown, MA). Cells were cultured in the transduction media for 20 hours, then transduction media was aspirated, cells were rinsed twice with 1×PBS, and culture media (F12+10% FBS+1% P/S) was added to the wells. Cells were allowed to recover for at least 24 hours. Transduction efficiency was tested using flow cytometry in a Millipore Guava easyCyte flow cytometer (Millipore Sigma, Burlington, MA) by staining with a rabbit-anti-firefly luciferase antibody (Abcam, Cambridge, UK). A transduction efficiency of ~81% was observed, validating the use of this system for visualizing cells in the longitudinal study.

In Vivo Disc Puncture Model and Cell-Laden Hydrogel Delivery

All animal work was done in accordance to the Washington University Institutional Animal Care and Use Committee. Male Sprague-Dawley rats (n=12, 10-12 weeks old, 285.2±19.0 grams) were purchased from Charles River, and allowed to acclimate for one week. Rats were co-housed (two rats per cage) in ventilated cages with wood chip bedding and enriched with a chew toy. Food and water were available ad libitum, and the rats were kept under a 12/12 light/dark cycle and with a constant room temperature of 21° C.±1. For surgical procedures, rats were first anesthetized under 1.5-3% isoflurane+1-2% $O_2$, and then given a subcutaneous injection of carprofen (5 mg/kg) 36. Caudal discs (C5-C8) were exposed by making an incision on the ventral plane of the tail using a size 21 blade. Specifically, the pedicles on the C4 vertebra were identified, and an incision was made just caudal of the C4-C5 disc. Following, disc C5-C6 was punctured to a depth of 3 mm using a 27G needle in all rats. Discs of all rats at the C6-C7 level were left without a puncture to be used as the sham control. Discs C7-C8 were likewise punctured to a depth of 3 mm using a 27G needle[37]. The incision was then closed using 4-0 nylon sutures. Chewable carprofen tablets (dosage of 5 mg/kg) were administered daily for 4 days following surgery. The rats were allowed to recover for 2 weeks in order to allow for progression of acute disc degeneration and allow the transient inflammatory response to resolve[37,43].

Following the two-week recovery period, rats were anesthetized using 1.5-3% isoflurane+1-2% $O_2$. As previously described, an incision was made on the ventral plane of the tail following identification of the C4 pedicles for orientation, and disc levels C5-C8 were exposed. Discs C5-C6 received two injections, the first being a cell-containing PEG-di-thiol solution and the second being the peptide-functionalized PEG-8MAL solution, in order to deliver 10 µL of the in situ crosslinked 15% 100 µM hydrogel with $2.5 \times 10^6$ cells/mL, using 25G needles and a Hamilton syringe (Hamilton Company, Reno, NV). The cells used for delivery were constitutive luciferase reporter rat NP cells previously described. Discs at the C6-C7 level remained unpunctured to serve as the sham controls. Discs C7-C8 were punctured an additional two times using a 25G needle in order to mimic the hydrogel delivery conditions but without delivering cells or gel. Tail incisions were then closed with 4-0 sutures, and the rats were allowed to recover, receiving chewable carprofen tables (dosage of 5 mg/kg) daily for 4 days. Rats were sacrificed at two different time points, with the first cohort of animals (n=6 rats) sacrificed one week following hydrogel delivery (t=1 week), and the second cohort (n=6 rats) sacrificed eight weeks following hydrogel delivery (t=8 weeks).

Tissue Harvesting, µCT, and Histology

At one- and eight-weeks post hydrogel delivery, rats were sacrificed and the caudal spines were immediately excised. The muscle and tail tendons surrounding the spine were removed, the spines were rinsed in 1×PBS, and then placed in 4% PFA for 48 hours with gentle rocking at 4° C. (replaced once after 24 hours). Following, the tails were analyzed under µCT using a Bruker SkyScan 1176 (Bruker Corporation, Billerica, MA) at 60 KV, 417 µA, and 65 ms exposure. Disc Height Index (DHI) was calculated by $$DHI = \frac{2(A_1 + A_2 + A_3)}{(B_1 + B_2 + B_3 + B_4 + B_5 + B_6)},$$

where $A_x$ are the measurements of disc height across 3 different points, and $B_x$ are the measurements of the bounding vertebral bodies at three individual planes[44]. Endplate degeneration grading was done as suggested by Ishiguro et al.[7,29] Following µCT imaging, discs were processed for histological sectioning. Whole spines were first decalcified in 14% (w/v) EDTA pH 7.2 for 7 days at 4° C. with gentle rocking, then cut into individual motion segments and decalcified for an additional 7 days in fresh 14% EDTA[45]. Following, motion segments were cryoprotected in 30% sucrose for 24 hours at 4° C., then embedded in OCT and snap-frozen in liquid nitrogen. All samples were stored at −80° C. until ready for sectioning. Histological sections were taken in the coronal plane at a thickness of 20 µm to preserve hydrogel integrity and prevent gel tearing. In order to measure effective cell localization as well as cell retention within the IVD space following cell-laden hydrogel delivery, sections were stained with a rabbit-anti-luciferase in order to visualize and identify the delivered reporter cells described above. For qualitative analysis of histological sections, discs were stained with 0.1% safranin-O, 0.02% fast green, and haematoxylin, then overlaid with Permount and coverslipped for imaging. For qualitative study of the phenotypic state of the delivered NP cells, sections were stained with a mouse-anti-N-Cadherin (Abcam, Cambridge, UK), rabbit-anti-BASP1 (Abcam, Cambridge, UK), or rabbit-anti-Integrin α6 (Abcam, Cambridge, UK). Sections were counterstained with DAPI for visualization of cell nuclei.

Results

Figure 16:
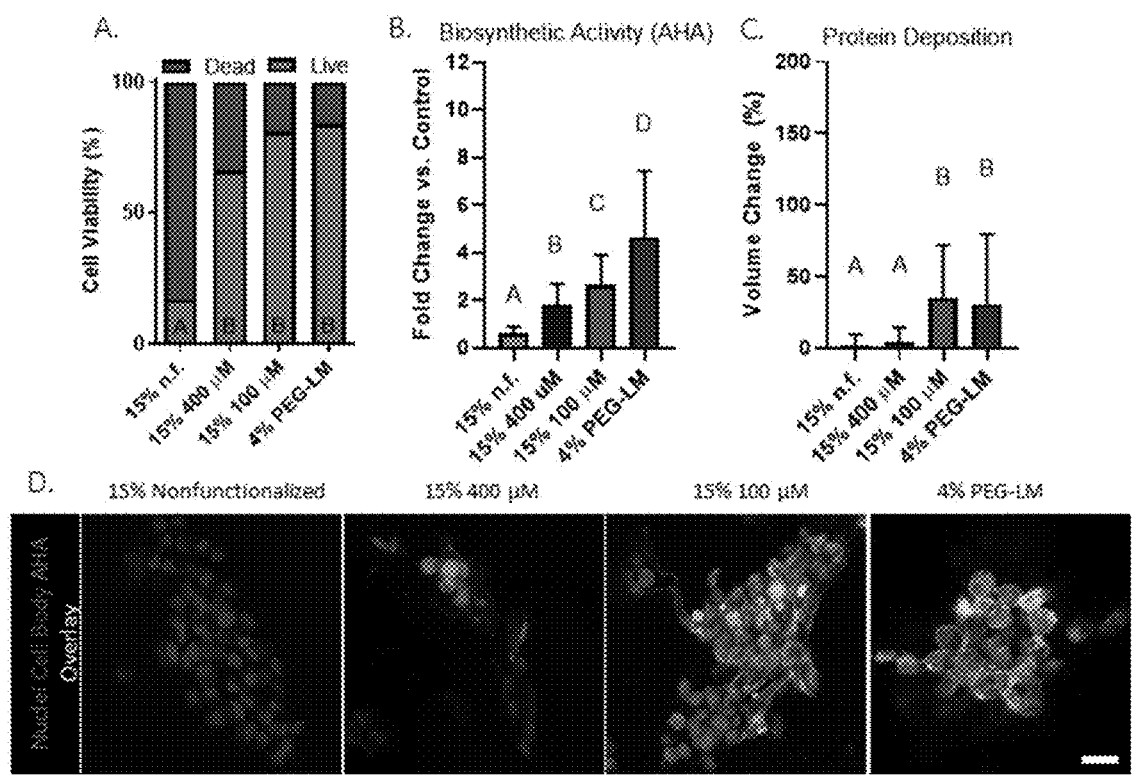
FIG. 16 Functionalized systems support cell viability and biosynthetic activity following 3D culture. A) Cell viability as quantified by Live/Dead assay. No statistical differences were found between functionalized substrates, but all different from nonfunctionalized controls. B-C) Biosynthetic activity and matrix deposition as measured via functional non-canonical amino acid tagging (FUNCAT) approach shows that both the stiff low peptide and soft PEG-LM substrates promote increased protein production compared to the stiff high peptide and nonfunctionalized controls, with PEG-LM demonstrating the highest biosynthetic activity. D) Representative images of FUNCAT. For all plots, n>22 independent ROIs collected from n≥3 human samples, ages 30-68, both sexes. Scale bar is 20 μm. Statistical test was a one-way ANOVA with Holm-Sidak's multiple comparison's test. Same letter denotes no significance, while different letters denote differences at p<0.05.
Figure 21:
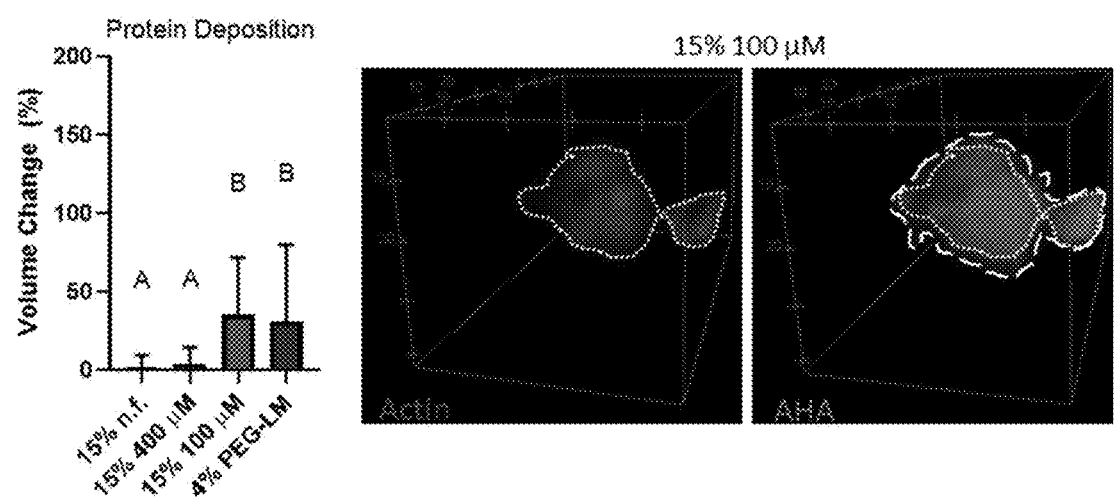
FIG. 21. Extracellular protein deposition. As described in FIG. 1, matrix deposition was measured via functional non-canonical amino acid tagging (FUNCAT) approach. The above representative image of the stiff low peptide gel provides a visual representation of the calculation of volume change based on staining of actin skeleton and newly deposited AHA-containing proteins. For the plot, n>22 independent ROIs collected from n≥3 human samples, ages 30-68, both sexes. Statistical test was one-way ANOVA with Holm-Sidak's multiple comparison's test. Same letter denotes no significance, while different letters denote differences at p<0.05.

Stiff Low Peptide-Functionalized Density Hydrogels Promote Cell Viability and Biosynthetic Activity in Human NP Cells Following 3D Culture In Vitro Significantly higher cell viability was observed in the stiff-low peptide density (15% 100 µM), stiff-high peptide (15% 400 µM), and soft PEG-laminin (4% PEG-LM) gels than the nonfunctionalized stiff hydrogel control, although the functionalized systems were not different from one another (FIG. 16A). All functionalized systems exhibited significantly higher biosynthetic activity than the stiff nonfunctionalized control, with the soft PEG-LM gel exhibiting significantly higher rates of biosynthesis than all other conditions (FIG. 16B, FIG. 16D). Soft PEG-LM as well as stiff-low peptide constructs demonstrated significantly higher amounts of extracellular protein deposition than both the stiff-high peptide system and nonfunctionalized controls (FIG. 16C, FIG. 21).

Figure 17:
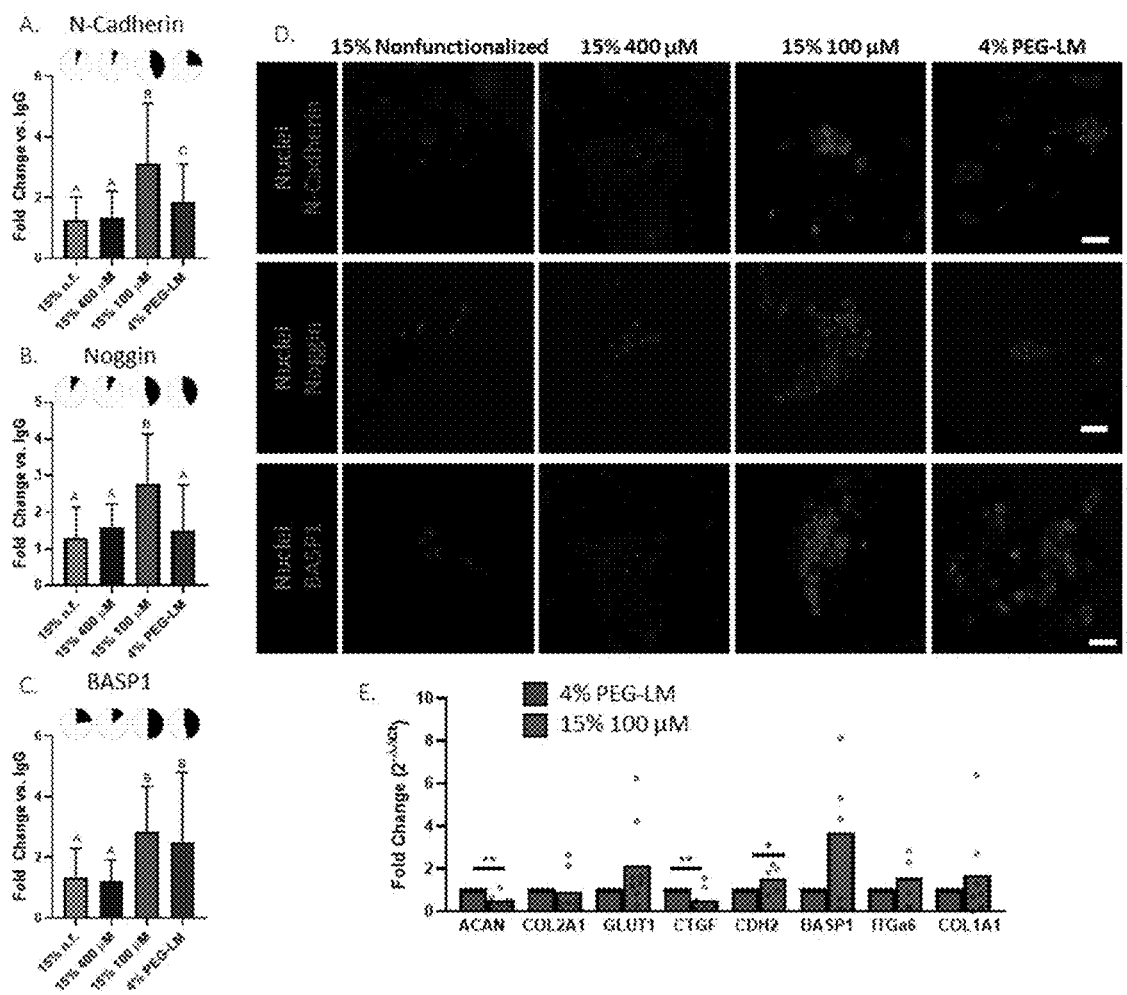
FIG. 17. Stiff low peptide and soft PEG-LM systems promote increases in protein expression. Stiff low peptide density promotes significantly higher levels of N-Cadherin (A, D) and noggin (B, D) than any other substrate, and significantly higher amounts of BASP1 (C, D) than both the stiff non-functionalized and stiff-high density substrates, though no different than the soft PEG-LM. Stiff low peptide system further suggests higher proportions of cells expressing all of these proteins than either the stiff high peptide and stiff non-functionalized system as shown by the pie-chart insets. E. Survey of gene expression profiles comparing the stiff-low peptide to the soft PEG-LM positive control. For A-C, n>60 ROIs from n≥3 human samples, ages 30-68, both sexes. Statistical test was one-way ANOVA with Holm-Sidak's multiple comparison's test. Same letter denotes no significance between conditions, different letter denotes p<0.05. Scale bar is 50 μm. For E) statistics were t-tests comparing the two substrates for each gen. * is p<0.05, ** is p<0.01.

Stiff-Low Peptide-Functionalized Systems Promote Increased Protein Deposition and Similar Gene Expression Profiles as Soft PEG-LM Gels for Cells in 3D Culture In Vitro The stiff-low peptide density hydrogel demonstrated the highest expression of N-cadherin and noggin of all substrates studied, along with higher proportions of cells expressing these proteins (FIG. 17A, FIG. 17B, FIG. 17D). No difference in expression or in proportions of cells expressing BASP1 were measured between the stiff-low peptide and soft PEG-LM substrates, although these were significantly higher than both the stiff-high and nonfunctionalized groups (FIG. 17C, FIG. 17D).

Figure 22:
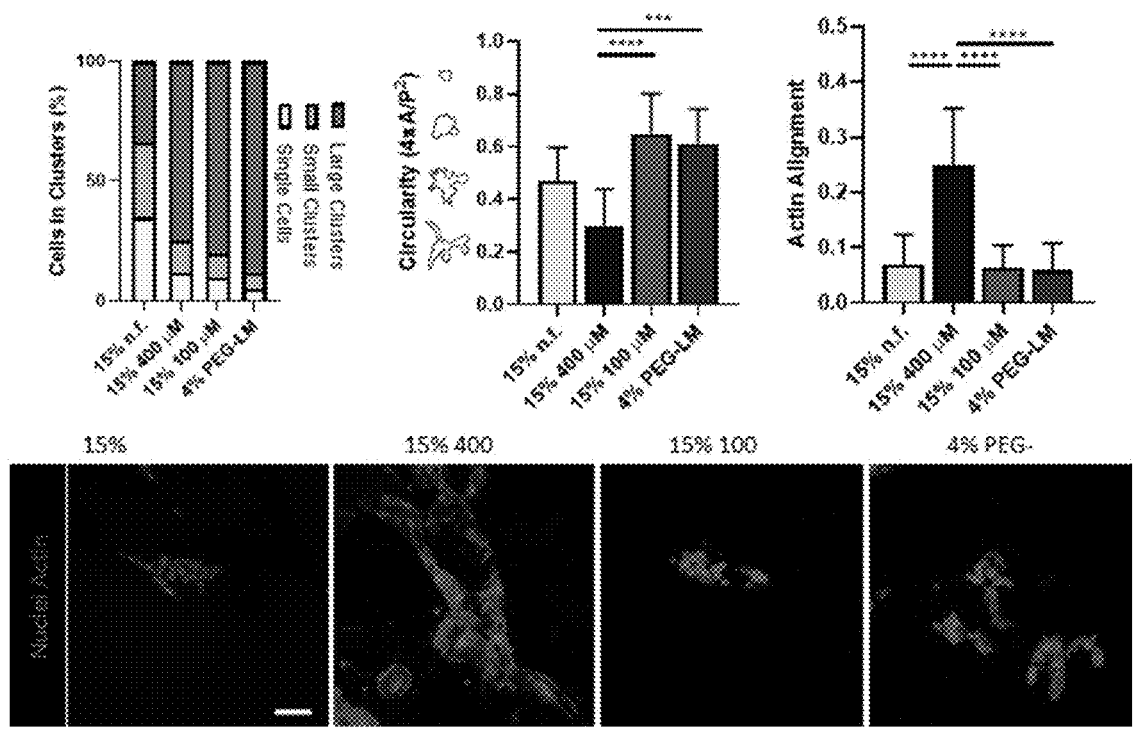
FIG. 22. Characterization of 3D morphological parameters. A) Quantification of cell clustering; small clusters are n=2-4 cells, large clusters are n>5 cells. B) Measures of cell cluster circularity of large clusters (n>5 cells) shows significant increase in cell clustering in stiff low peptide and soft PEG-LM substrates than the stiff high peptide controls. C) Measurement of F-actin fiber alignment and cytoskeletal organization. D) Actin staining on all substrates shows the rounded clustered morphology typical of a more "juvenile" phenotype in the stiff-low peptide (15% 100 μM) and soft (4%) PEG-LM substrate, while the stiff-high peptide (15% 400 M) system promotes the elongated, spread morphology previously characterized in 2D, typical of a more fibroblast-like state. Scale bar is 50 μm. * p<0.001, ** p<0.0001 using one-way ANOVA with Holm-Sidak's multiple comparison's test.

The soft PEG-LM gel has previously been demonstrated to promote expression of NP cell phenotypic markers including ACAN, BASP1, CDH2, and GLUT1 following 2D and 3D culture[8,31,32]. Therefore, expression profiles of NP cells encapsulated in the stiff-low peptide-functionalized gels was compared to cells cultured within soft PEG-LM gels. Gene expression profiles were not surveyed for nonfunctionalized and stiff-high peptide density groups due to their observed low protein expression and increased morphological differences resembling those of a more fibroblast-like phenotype (FIG. 22). We observed gene expression of ACAN and CTGF was reduced by the stiff peptide-functionalized gels compared to soft PEG-LM. In contrast, CDH2 expression was significantly increased by the stiff-low peptide-functionalized gels compared to soft PEG-LM. The data further demonstrated nonsignificant trends towards increased expression of GLUT1 and BASP1, and similar expression levels of COL2A1, ITGA6, and COL1A1 between the two hydrogels tested (FIG. 17E).

Figure 18:
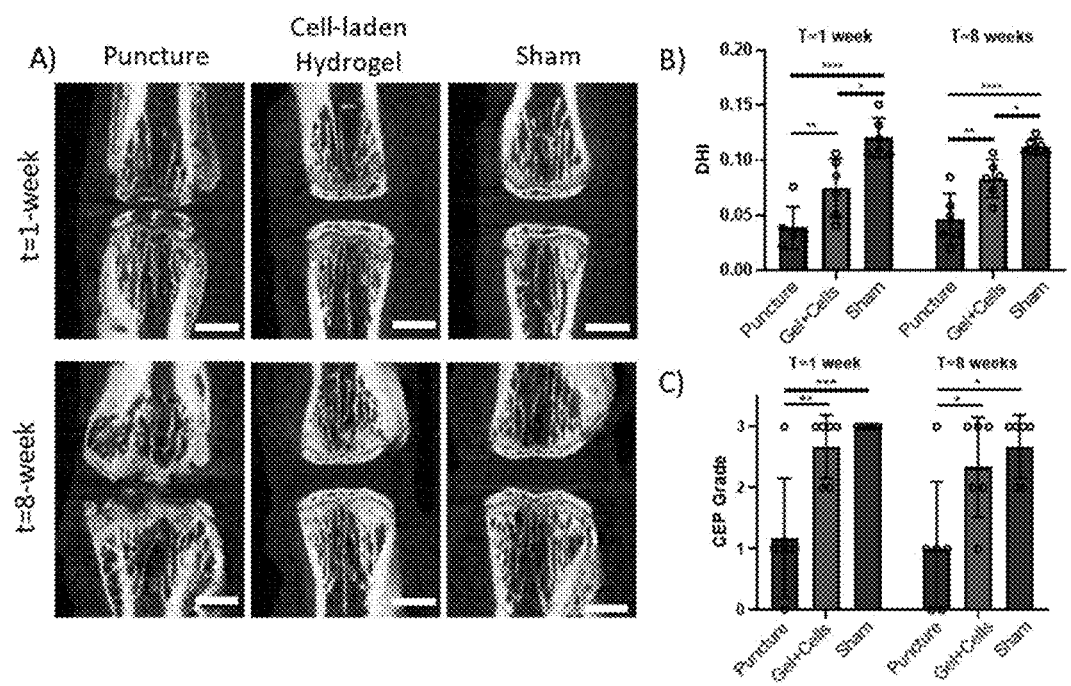
FIG. 18. Radiographic evaluation of the coccygeal spine. A) μCT scans of the discs show significantly higher disc height index (DHI) in the hydrogel delivery conditions compared to the punctured non treated discs. B) At both the 1 and 8 week timepoints, DHI in hydrogel delivery conditions compared to sham discs is significantly lower, although both DHI and endplate scores (C) in hydrogel delivery conditions are higher than those in the punctured non treated control. n=6 rats per condition per timepoint. Scale bars in A are 2 mm. Statistics for B and C were one-way ANOVAs with Holm-Sidak's multiple comparisons test. * p<0.05,  p<0.01, * p<0.001, **** p<0.0001.

Cell Laden Stiff-Low Peptide-Functionalized Hydrogel Delivery into the Rat Intradiscal Space In Vivo Promotes Improved DHI and Endplate Structure Based on the in vitro findings that the stiff-low peptide-functionalized hydrogels supported cell viability and biosynthetic activity at levels similar to or greater than the pro-phenotypic soft PEG-LM, only the stiff low peptide density system was used as the cell carrier for delivery into the degenerative IVD. Significant increases in disc height index (DHI) were observed in treated discs compared to the punctured non-treated controls at both the 1-week and 8-week timepoints following cell-laden hydrogel delivery. (FIG. 18A, FIG. 18B). However, the cell-laden hydrogel delivery group did exhibit significantly lower DHI's compared to the sham (non-punctured) controls. μCT imaging further revealed differences in endplate structure between the conditions (FIG. 18A, FIG. 18C). Semi-quantitative grading of the endplates[29] suggested improved endplate scores in the treated group compared to the punctured controls, and similar scores were seen in the treated and sham groups (FIG. 18A, FIG. 18C).

Cell-Laden Hydrogel Delivery Promotes Improved Disc Phenotype

Figure 19:
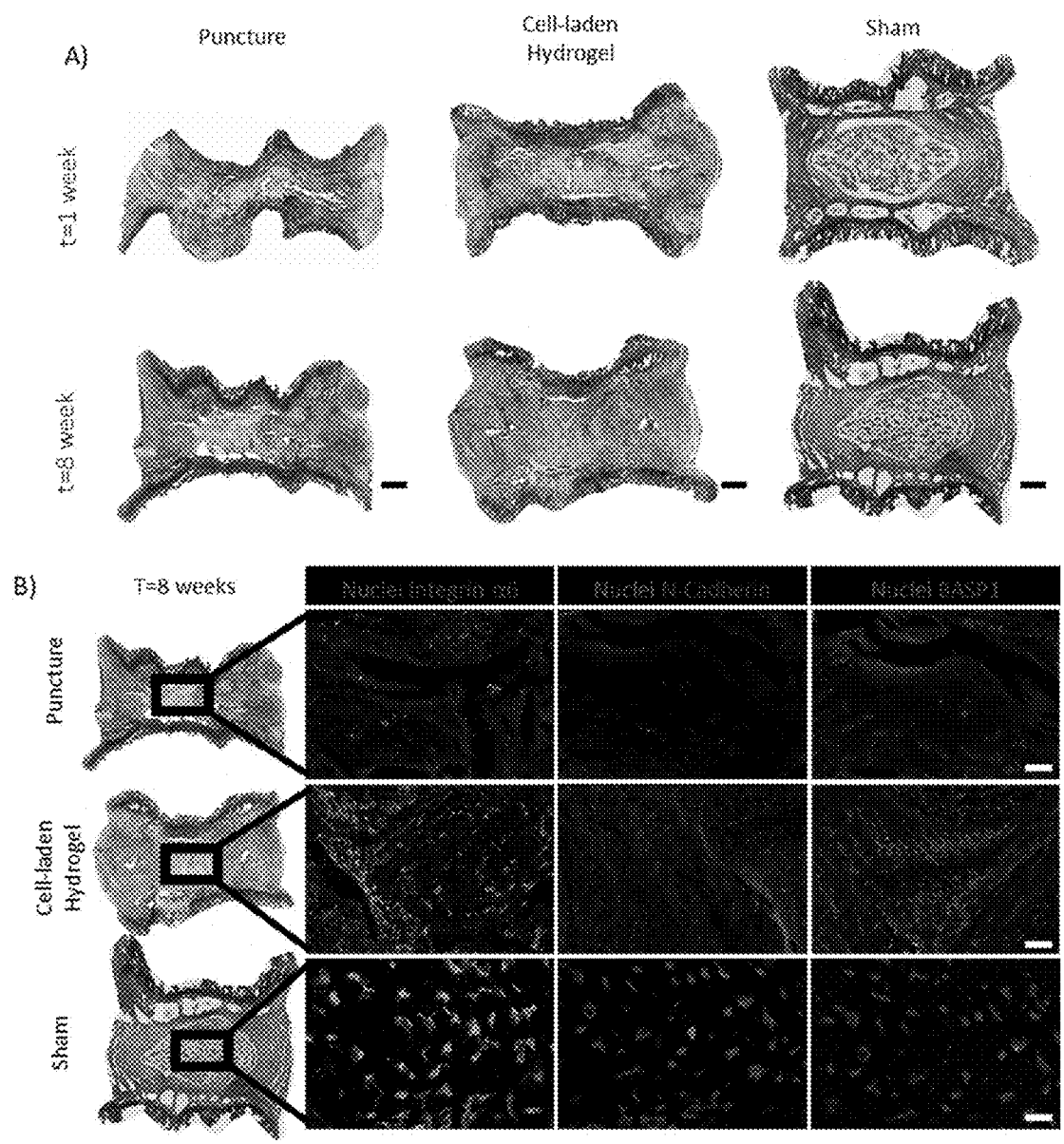
FIG. 19. Histological assessments of the IVDs. A) 20 μm thick tissue sections, stained via Saf-O/Fast Green/Haematoxylin. Scale bar is 500 μm. B) At the eighth week post-injury timepoint, differences in protein expression levels between groups was apparent. Although protein expression in the cell-laden hydrogel condition appeared to resemble that of the naïve condition, morphological differences in cell distribution could still be observed. Scale bar is 250 μm.
Figure 23:
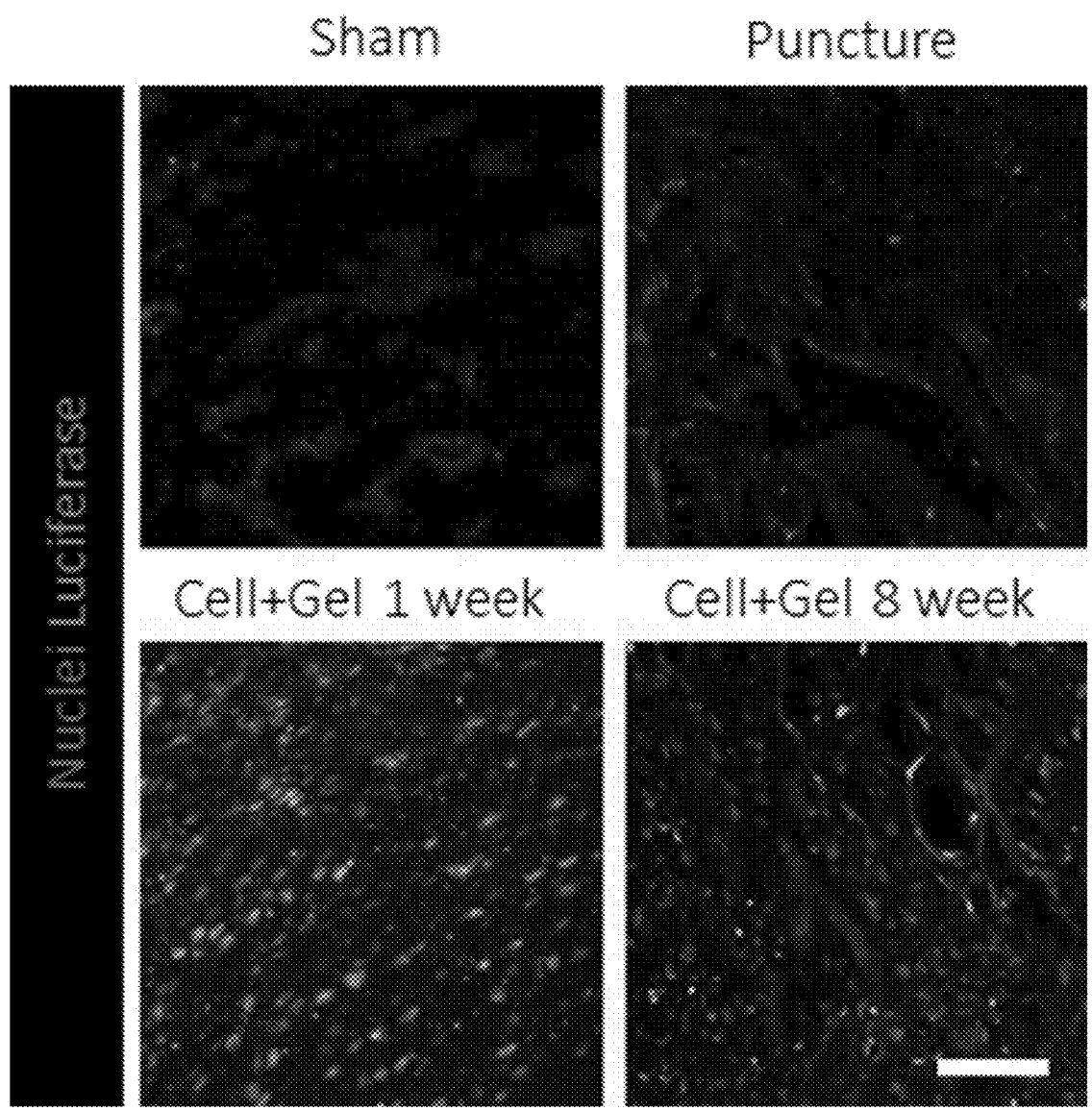
FIG. 23. Confirmation of cell delivery. Immunofluorescence demonstrates the presence of a luc+ cell population within the intradiscal space in the cell-laden hydrogel delivery conditions. Scale bar is 100 μm.

Increased presence of luciferase+ cells in the cell-laden hydrogel delivery condition confirmed effective delivery and retention of rat NP cells into the intradiscal space (FIG. 23). Discs from the puncture group exhibited severe damage at both time points, as characterized by disorganized endplates with irregularities and focal defects, reduced AF organization, and the disappearance/collagenization of the NP (FIG. 19A). Furthermore, histology suggested a decrease in cellularity within the central region of the punctured non-treated discs. By contrast, endplates in the discs from the cell-laden hydrogel delivery group at both time points exhibited organized structures and more closely resemble the endplates from the sham group than those of the punctured discs. Furthermore, while alterations in AF organization can be observed (likely as a result of the initial puncture insult), distinct lamella remain observable in the treated group at both timepoints. Lastly, the cell-laden hydrogel delivery group at the 8 week time point demonstrated increased Saf-O staining within the central region of the disc, which was not observed in the punctured controls at either time point, nor in the hydrogel delivery group at the one week time point. This may be indicative of cell viability and biosynthetic activity throughout the course of the study, although it may further suggest a longer time required for cells to adapt to their microenvironment following in vivo delivery. Histological assessment of the sham discs demonstrated tissue organization and structure consistent with healthy IVDs.

Figure 24:
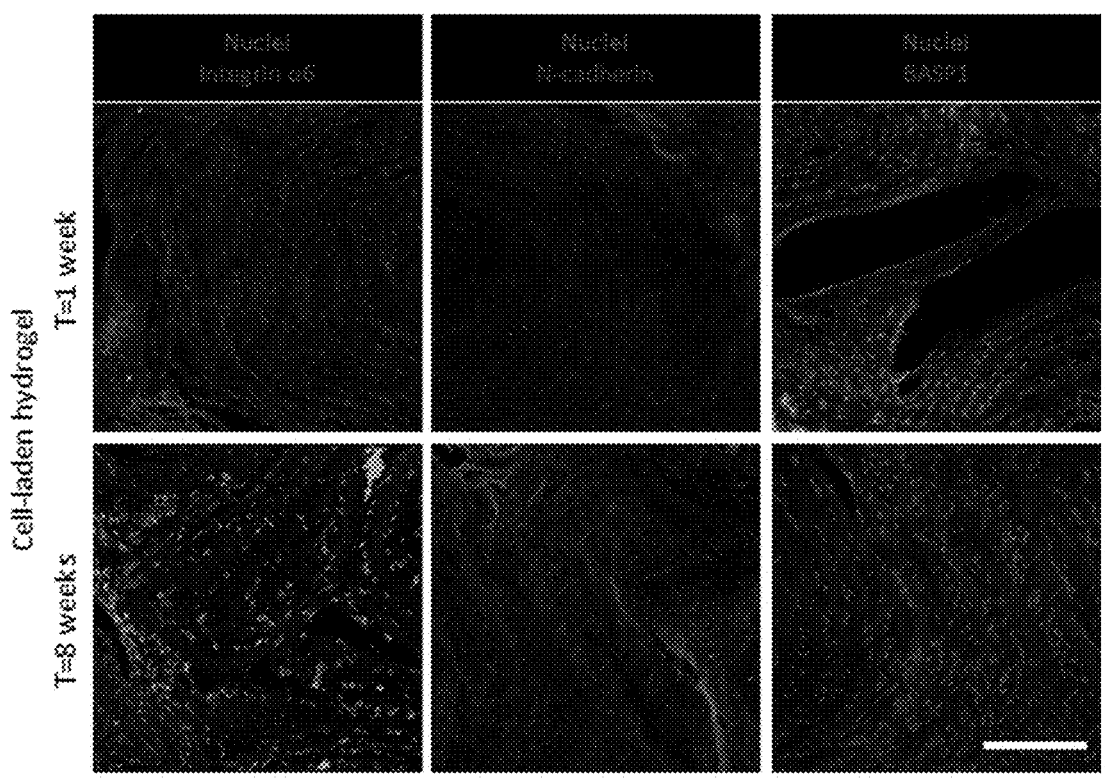
FIG. 24. Protein expression differences versus time. Immunohistochemical analysis suggests differential levels of protein expression as a matter of treatment group as well as time. Scale bar is 250 μm.
Figure 25:
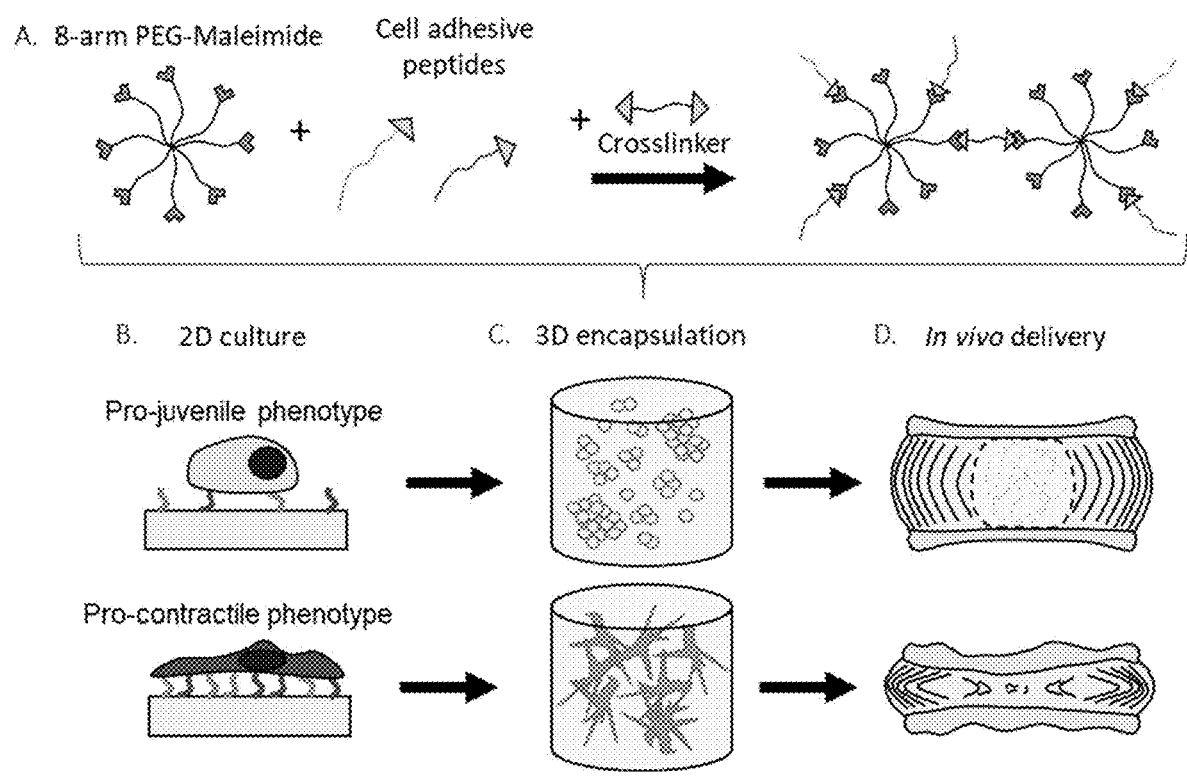
FIG. 25. Schematic of peptide-functionalization and cell culture systems. A) Addition of adhesive domains to the 8-arm PEG-maleimide backbone promotes biofunctionalization of the polymer backbone. Further addition of a cross-linker promotes formation of cell culture systems for use as B) 2D cell culture substrates, C) 3D cell encapsulation systems, and can further be used for in vivo delivery of cells within the functionalized hydrogel carrier to promote disc phenotypic shifts (D).

Immunostaining for BASP1, N-Cadherin, and Integrin α6 revealed protein presence in both the sham control as well as the hydrogel treated NP regions, while little staining was observed in the punctured NP sections (FIG. 19B). Notably, cellularity appeared strongly reduced in the punctured conditions, potentially playing a role in the apparent decrease in protein expression in these tissues. Although trends suggesting higher protein expression in the cell-laden hydrogel group than in the puncture group were observed at both time points, interestingly, the relative protein expression in the cell-laden hydrogel conditions appeared qualitatively higher at the 8-week time point than the 1-week time point, particularly in terms of expression levels of integrin α6 and N-cadherin (FIG. 24). These observations may be further suggestive of cells needing a recovery period following intradiscal delivery prior to phenotypic re-expression.

Discussion

Although full-length laminin-111-functionalized materials have demonstrated the ability to promote shifts in expression of a panel of markers associated with the juvenile NP cell phenotype, this approach poses difficulties due to the protein's size and complexity[32,46]. Use of laminin-mimetic peptides offers advantages in terms of increased specificity for cell engagement and ligand-receptor interactions, spatial control over ligand presentation, and more[30,40]. Additionally, while previous work has demonstrated that soft, laminin presenting biomaterials promote increased expression of markers associated with the juvenile NP phenotype in vitro[8,31,32,47], development of stiff biomaterials may be favorable for in vivo delivery due to the increased mechanical support. As such, in the present study we examined the potential for a stiff peptide-functionalized hydrogel to be used as a cell-carrier for delivery into the degenerative intradiscal space in order to increase disc height and promote cell matrix deposition and tissue integration.

All functionalized biomaterials tested appeared to promote similar degrees of cell viability, although the stiff biomaterial functionalized with a high peptide density was observed to have significantly lower biosynthetic activity than both the stiff-low peptide and soft PEG-LM systems. Lower degrees of protein expression were further observed in the stiff-high peptide density system than either the stiff-low or soft PEG-LM, which is likely associated with the observed changes in biosynthetic activity. Cells cultured within the stiff-low peptide-functionalized gels exhibited the highest protein expression of N-cadherin and noggin among all substrates studied, and exhibited expression levels of BASP1 that were similar to that seen in the soft PEG-LM positive controls. Formation of cytosolic vacuoles was further observed in 3D culture of adult human NP cells within both the soft PEG-LM and stiff low peptide density hydrogels, while no vacuolation was observed in either the non-functionalized nor the stiff high peptide density groups (data not shown). This observation is of interest because AHA staining within vacuolar structures appeared modest at best, which may support the hypothesis that vacuoles play a more important role in regulation of intracellular pressure than in molecular transport[48-50]. Together these data validate the stiff biomaterial functionalized with laminin mimetic peptides as a bioinductive scaffold capable of promoting cellular behaviors similar to the soft PEG-LM hydrogel during 3D in vitro culture. A key feature of this system is its intrinsic ability for modification. The use of chemically functionalized synthetic polymer systems for cell encapsulation supports the independent control of different material parameters such as hydrogel stiffness and degree of functionalization. This allows for the creation of a stiff biomaterial with reduced peptide density. In natural polymer systems, adhesive domains (e.g., RGD in the case of collagen) are inherently linked to the fiber density[51-53]. Thus, an increase in polymer density for creating a stiffer substrate leads to an increase in adhesive ligand domain availability. This is important, as the controlled presentation of ligands in the stiff polymers has been previously observed to lead to significant changes in phenotypic marker expression[30].

We then assessed the effects of injecting the cell-laden peptide-functionalized system as a therapeutic to discs degenerated via anular puncture in a rat model of degeneration. In vivo delivery of the peptide-functionalized in situ crosslinked cell-laden hydrogel promoted significantly higher DHI values compared to the puncture group, although these values were significantly lower than in the sham control. µCT analysis further suggested significant changes in endplate organization, with the cell-laden hydrogel group promoting significantly higher degrees of endplate organization than the puncture group, while not being significantly different than the sham group. The peptide-functionalized hydrogel also promoted cell phenotype and exhibited bioinductive properties in vivo as characterized by increased expression of integrin α6, N-cadherin, and BASP1, as well as increased Saf-O presence within the central region of the disc, compared to the punctured group. Differences in disc phenotype between the t=1 week and t=8-week conditions for the cell-laden hydrogel delivery group were observed. Specifically, at t=8 weeks, there was observable Saf-O staining within the central region of the disc, as well as observable protein expression. However, none of these markers were observed at the 1-week time point (FIG. 24). This may be due to cells requiring a longer time to reach steady state in vivo than in vitro. Following in vivo delivery, cells which were previously cultured in monolayer experience an increase in dimensionality which leads to temporal and spatial alterations to nutrient accessibility, oxygen gradients, and more. The hypoxic and low nutrient disc environment in vivo further presents stresses to the delivered cells, which may further result in a slow rate of recovery that leads to longer times being necessary for cells to express the phenotypes observed in vitro[54,55].

Figure 20:
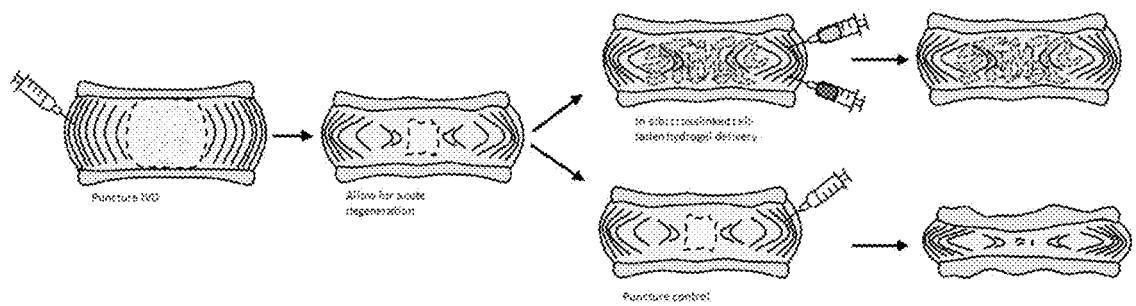
FIG. 20. Hydrogel delivery schematic. Representative schematic of the hypothesized workflow outlining the degrees of degeneration following disc punctures and the in situ crosslinked cell-laden hydrogel implant.

As suggested in the schematic from FIG. 20, we hypothesize that the in situ crosslinked system may act in a defect filling manner, with gel becoming entrapped in voids in the nucleotomized disc and the collapsed anular fibers. Both the treated and non-treated discs which underwent puncture show anular disruption and disorganization at early timepoints. This suggests that although the mechanical support provided by the hydrogel may be sufficient to increase disc height and vertebral body separation, it does not provide enough intradiscal pressure to entirely mimic the healthy NP and counteract the AF buckling which results from the puncture injury[56,57]. This is further supported by the observation that, particularly at the 8-week timepoint, the endplates in the treated condition appear healthy and similar to the sham control while the endplates in the non-treated punctured discs show signs of severe degeneration. This finding may suggest that the stiff hydrogel provides help to attenuate endplate damage resulting from disc collapse[11,58] However, addition studies such as cyclical loading and compression tests would be required to further assess the mechanical properties of the gel and to further elucidate the role of the hydrogel implant in providing mechanical support to the motion segments.

Together, the data from the present study suggest an ability to use the stiff low peptide density functionalized PEG hydrogel scaffold for efficient 3D encapsulation and cell delivery into the degenerative disc space. Results from both in vivo and in vitro culture validate the system as an effective cell carrier capable of promoting cell retention within the IVD, and able to provide cells with cues critical for promoting cell viability, increased biosynthetic activity, matrix deposition, and protein expression. The benefit of the cell-laden construct appeared to be most prominent at the 8-week timepoint, suggesting that the biomaterial construct may promote significant structural and phenotypic shifts at chronic timepoints which may be disease modifying and reduce initiation of pain.

REFERENCES

1. Iatridis, J. C., Setton, L. A., Weidenbaum, M. & Mow, V. C. Alterations in the Mechanical Behavior of the Human Lumbar Nucleus Pulposus with Degeneration and Aging. *J. Orthop. Res.* 15, 318-322 (1997).
2. Roughley, P. J. Biology of intervertebral disc aging and degeneration: involvement of the extracellular matrix. *Spine* (Phila. Pa. 1976). 29, 2691-2699 (2004).
3. Adams, M. A. & Roughley, P. J. What is Intervertebral Disc Degeneration, and What Causes It? *Spine* (Phila. Pa. 1976). 31, 2151-2161 (2006).
4. Urban, J. P. G. & Roberts, S. Degeneration of the intervertebral disc. *Arthritis Res. Ther.* 5, 120-130 (2003).
5. Chan, W. C. W., Sze, K. L., Samartzis, D., Leung, V. Y. L. & Chan, D. Structure and Biology of the Intervertebral Disk in Health and Disease. *Orthop. Clin. N Am* 42, 447-464 (2011).
6. Setton, L. A. & Chen, J. Mechanobiology of the Intervertebral Disc and Relevance to Disc Degeneration. *J. Bone Jt. Surg.* 88, 52 (2006).
7. Boos, N. et al. Classification of age-related changes in lumbar intervertebral discs. *Spine* (Phila. Pa. 1976). 27, 2631-2644 (2002).
8. Fearing, B. V. et al. Mechanosensitive transcriptional coactivators MRTF-A and YAP/TAZ regulate nucleus pulposus cell phenotype through cell shape. *FASEB* 1-14 (2019). doi: 10.1096/fj.201802725RRR
9. Iatridis, J. C., Weidenbaum, M., Setton, L. A. & Mow, V. C. Is the Nucleus Pulposus a Solid or a Fluid? Mechanical Behaviors of the Nucleus Pulposus of the Human Intervertebral Disc. *Spine* (Phila. Pa. 1976). 21, 1174-1184 (1996).

10. Cloyd, J. M. et al. Material properties in unconfined compression of human nucleus pulposus, injectable hyaluronic acid-based hydrogels and tissue engineering scaffolds. *Eur Spine J* 16, 1892-1898 (2007).
11. Walter, B. A. et al. M R Elastography-derived Stiffness: A Biomarker for Intervertebral Disc Degeneration. *Radiology* 285, 167-175 (2017).
12. Pattappa, G. et al. Diversity of intervertebral disc cells: phenotype and function. *J. Anat.* 221, 480-496 (2012).
13. Freemont, A. J. et al. Nerve ingrowth into diseased intervertebral disc in chronic back pain. *Lancet* 350, (1997).
14. Chen, J. et al. Expression of Laminin Isoforms, Receptors, and Binding Proteins Unique to Nucleus Pulposus Cells of Immature Intervertebral Disc Expression of Laminin Isoforms, Receptors, and Binding Proteins Unique to Nucleus Pulposus Cells of Immature Intervertebra. *Connect. Tissue Res.* 50, 294-306 (2009).
15. Trout, J. J., Buckwalter, J. A., Moore, K. C. & Landas, S. K. Ultrastructure of the human intervertebral disc. I. Changes in notochordal cells with age. *Tissue Cell* 14, 359-369 (1982).
16. Woiciechowsky, C. et al. Regeneration of nucleus pulposus tissue in an ovine intervertebral disc degeneration model by cell-free resorbable polymer scaffolds. *J. Tissue Eng. Regen. Med.* (2012). doi: 10.1002/term
17. Bowles, R. D., Williams, R. M., Zipfel, W. R. & Bonassar, L. J. Self-Assembly of Aligned Tissue-Engineered Annulus and Intervertebral Disc Composite Via Collagen Gel Contraction. *Tissue Eng.* Part A 16, 1339-1348 (2010).
18. Mizuno, H. et al. Tissue-Engineered Composites of Anulus Fibrosus and Nucleus Pulposus for Intervertebral Disc Replacement. Spine (Phila. Pa. 1976). 29, 1290-1298 (2004).
19. Bidarra, S. J., Barrias, C. C. & Granja, P. L. Injectable alginate hydrogels for cell delivery in tissue engineering. *Acta Biomater.* (2014). doi: 10.1016/j.actbio.2013.12.006
20. Rajesh, D. & Dahia, C. L. Role of Sonic Hedgehog Signaling Pathway in Intervertebral Disc Formation and Maintenance. *Curr Mol Biol Rep* 4, 173-179 (2019).
21. Nerlich, A. G., Schaaf, R., Walchli, B. & Boos, N. Temporo-spatial distribution of blood vessels in human lumbar intervertebral discs. *Eur Spine J* 16, 547-555 (2006).
22. Kauppila, L. I. Ingrowth of Blood Vessels in Disc Degeneration. *J. Bone Jt. Surg.* 77, 26-31 (1995).
23. Tsujimoto, T. et al. An acellular bioresorbable ultra-purified alginate gel promotes intervertebral disc repair: A preclinical proof-of-concept study. *EBioMedicine* 37, 521-534 (2018).
24. Thorpe, A. A. et al. Thermally triggered hydrogel injection into bovine intervertebral disc tissue explants induces differentiation of mesenchymal stem cells and restores mechanical function. *Acta Biomater.* 54, 212-226 (2017).
25. Gullbrand, S. E. et al. Hydrogel for Intervertebral Disc Regeneration in a Goat Model. 201-209 (2018). doi: 10.1016/j.actbio.2017.07.025.Translation
26. Maroudas, A., Stockwell, R. A., Nachemson, A. & Urban, J. Factors involved in the nutrition of the human lumbar intervertebral disc: cellularity and diffusion of glucose in vitro. 113-130 (1975).
27. Vadala, G. et al. Mesenchymal stem cells injection in degenerated intervertebral disc: cell leakage may induce osteophyte formation. *J. Tissue Eng. Regen. Med.* 6, 348-355 (2012).
28. Tam, V., Rogers, I., Chan, D., Leung, V. Y. L. & Cheung, K. M. C. A Comparison of Intravenous and Intradiscal Delivery of Multipotential Stem Cells on the Healing of Injured Intervertebral Disk Architecture nor the Disk Height Index. *J. Orthop. Res.* 819-825 (2014). doi: 10.1002/jor.22605
29. Ishiguro, H. et al. Intervertebral disc regeneration with an adipose mesenchymal stem cell-derived tissue-engineered construct in a rat nucleotomy model. *Acta Biomater.* 87, 118-129 (2019).
30. Barcellona, M. N. et al. Control of adhesive ligand density for modulation of nucleus pulposus cell phenotype. *Biomaterials* 250, (2020).
31. Francisco, A. T. et al. Biomaterials Injectable laminin-functionalized hydrogel for nucleus pulposus regeneration. *Biomaterials* 34, 7381-7388 (2013).
32. Francisco, A. T. et al. Photocrosslinkable laminin-functionalized polyethylene glycol hydrogel for intervertebral disc regeneration. *Acta Biomater.* 10, 1102-1111 (2014).
33. Bridgen, D. T. et al. Integrin-Mediated Interactions with Extracellular Matrix Proteins for Nucleus Pulposus Cells of the Human Intervertebral Disc. *J. Orthop. Res.* 31, 1-14 (2014).
34. Martin, J. T. et al. Needle puncture injury causes acute and long-term mechanical deficiency in a mouse model of intervertebral disc degeneration. *J. Orthop. Res.* 31, 1276-1282 (2013).
35. Korecki, C. L., Costi, J. J. & Iatridis, J. C. Needle Puncture Injury Affects Intervertebral Disc Mechanics and Biology in an Organ Culture Model. Spine (Phila. Pa. 1976). 33, 235-241 (2008).
36. Mohd Isa, I. L. et al. Implantation of hyaluronic acid hydrogel prevents the pain phenotype in a rat model of intervertebral disc injury. *Sci. Adv.* 1-20 (2018).
37. Leimer, E. M. et al. Behavioral Compensations and Neuronal Remodeling in a Rodent Model of Chronic Intervertebral Disc Degeneration. *Nat. Sci. Reports* 1-10 (2019). doi: 10.1038/s41598-019-39657-6
38. Masuda, K. et al. A Novel Rabbit Model of Mild, Reproducible Disc Degeneration by an Anulus Needle Puncture: Correlation Between theDegree of Disc Injury and Radiological and Histological Appearances of Disc Degeneration. Spine (Phila. Pa. 1976). 30, 5-14 (2004).
39. Nilsson, E., Nakamae, T. & Olmarker, K. Pain Behavior Changes Following Disc Puncture Relate to Nucleus Pulposus Rather than to the Disc Injury Per Se: An Experimental Study in Rats. *Open Orthop. J.* 5, 72-77 (2011).
40. Bridgen, D. T. et al. Regulation of human nucleus pulposus cells by peptide-coupled substrates. *Acta Biomater.* 55, 100-108 (2017).
41. Mcleod, C. M. & Mauck, R. L. High fidelity visualization of cell-to-cell variation and temporal dynamics in nascent extracellular matrix formation. *Nat. Publ. Gr.* (2016). doi: 10.1038/srep38852
42. Risbud, M. V. et al. Defining the Phenotype of Young Healthy Nucleus Pulposus Cells: Recommendations of the Spine Research Interest Group at the 2014 Annual ORS Meeting. *J Orthop Res* 33, 283-293 (2015).
43. Miyagi, M. et al. Disk Injury in Rats Produces Persistent Increases in Pain-Related Neuropeptides in Dorsal Root Ganglia and Spinal Cord Glia but Only Transient Increases in Inflammatory Mediators. Spine (Phila. Pa. 1976). 36, 2260-2266 (2011).
44. Vincent, K. et al. Aging of mouse intervertebral disc and association with back pain. *Bone* 123, 246-259 (2019).

45. Binch, A., Snuggs, J. & Le Maitre, C. L. Immunohistochemical analysis of protein expression in formalin fixed paraffin embedded human intervertebral disc tissues. *JOR Spine* (2020). doi: 10.1002/jsp2.1098
46. Kikkawa, Y. et al. Laminin-111-derived peptides and cancer. *Cell Adhes. Migr.* 7, 150-159 (2013).
47. Gilchrist, C. L., Darling, E. M., Chen, J. & Setton, L. A. Extracellular matrix ligand and stiffness modulate immature nucleus pulposus cell-cell interactions. *PLOS One* 6, (2011).
48. Hong, X., Zhang, C., Wang, F. & Wu, X.-T. Large Cytoplasmic Vacuoles within Notochordal Nucleus Pulposus Cells: A Possible Regulator of Intracellular Pressure That Shapes the Cytoskeleton and Controls Proliferation. *Cells Tissues Organs* 206, 9-15 (2018).
49. Resutek, L. & Hsieh, A. H. The vacuolated morphology of chordoma cells is dependent on cytokeratin intermediate filaments. *Cell. Physiol.* 234, 3458-3468 (2019).
50. Wang, F. et al. Formation, function, and exhaustion of notochordal cytoplasmic vacuoles within intervertebral disc: current understanding and speculation. *Oncotarget* 8, 57800-57812 (2017).
51. Enemchukwu, N. O. et al. Synthetic matrices reveal contributions of ECM biophysical and biochemical properties to epithelial morphogenesis. *J. Cell Biol.* 212, 113-124 (2016).
52. O'Brien, L. E., Zegers, M. M. P. & Mostov, K. E. Building epithelial architecture: insights from three-dimensional culture models. *Nat. Rev. Mol. Cell Biol.* 3, (2002).
53. Mroue, R. & Bissell, M. J. Three-Dimensional Cultures of Mouse Mammary Epithelial Cells. *Methods Mol. Biol.* 945, 221-250 (2013).
54. Hiyama, A. et al. Hypoxia Activates the Notch Signaling Pathway in Cells of the Intervertebral Disc. *Arthritis Rheum.* 63, 1355-1364 (2011).
55. Aker, L. et al. Molecular Biology and Interactions in Intervertebral Disc Development, Homeostasis, and Degeneration, with Emphasis on Future Therapies: A Systematic Review. *Spine Sch.* 1, 2-20 (2017).
56. Mohanty, S., Pinelli, R., Pricop, P., Albert, T. J. & Dahia, C. L. Chondrocyte-like nested cells in the aged intervertebral disc are late-stage nucleus pulposus cells. *Aging Cell* 1-5 (2019). doi: 10.1111/acel. 13006
57. Nagae, M. et al. Intervertebral Disc Regeneration Using Platelet-Rich Plasma and Biodegradable Gelatin Hydrogel Microspheres. *Tissue Eng.* 13, 147-158 (2007).
58. Fields, A. J., Liebenberg, E. C. & Lotz, J. C. Innervation of pathologies in the lumbar vertebral end plate and intervertebral disc. *Spine J.* 14, 513-521 (2014).

Example 8: Stem Cell Supporting Biocompatible 3D Polymer Material

This example describes data demonstrating that stem cells interacting with the gel upregulate anti-inflammatory markers.

Figure 26:
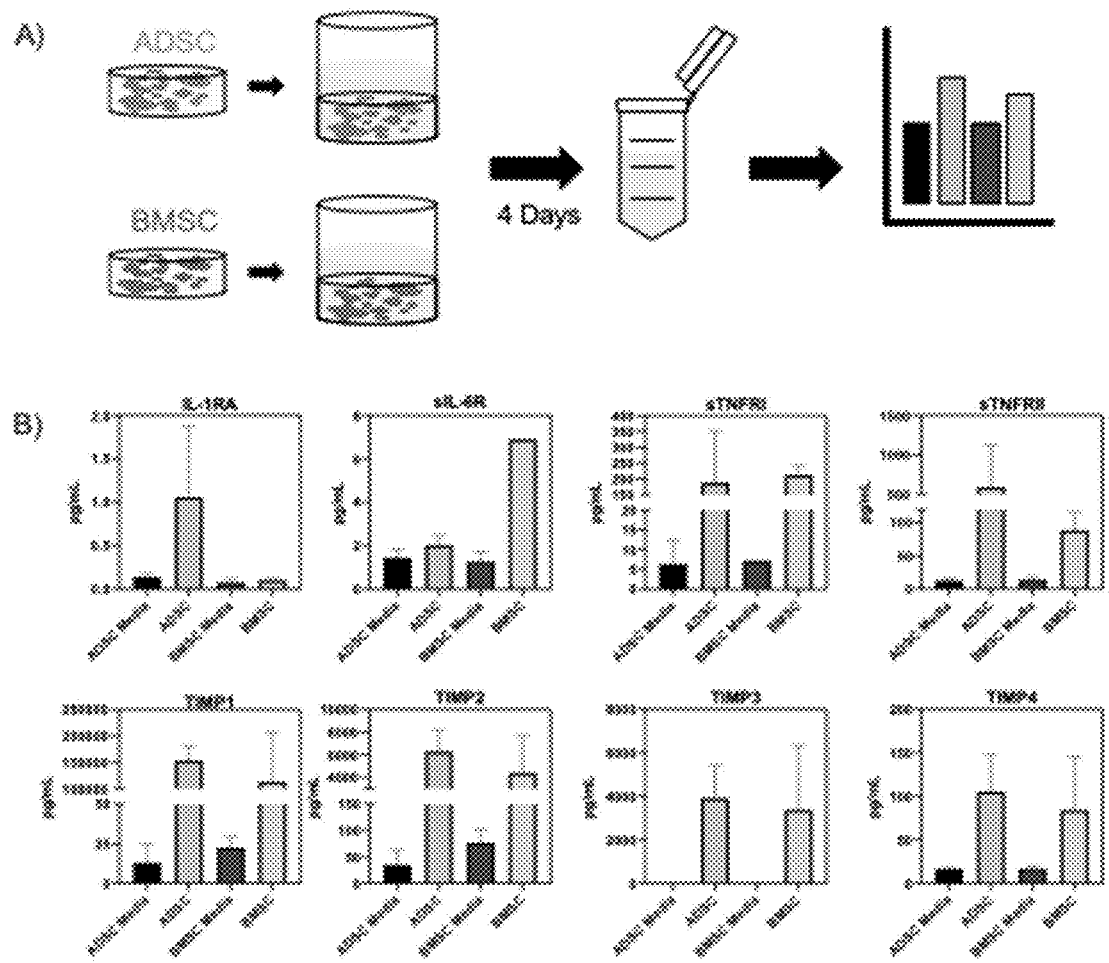
FIG. 26. Expression of proteins in adipose stem cells (ADSC) and bone marrow stem cells (BMSC) following 3D culture in IKVAV- and AG73-functionalized gels. A) Schematic showing stem cells encapsulated in the gel were cultured in 3D for 4 days. The supernatant was then removed and analyzed to identify secreted proteins. B) Expression profiles of proteins by stem cells encapsulated in peptide-functionalized gels as compared to the culture media only.

In addition to the previous examples showing NP cell supporting polymer material, here it is shown that stem cells can also be supported on the polymer material. Expression of proteins in adipose stem cells (ADSC) and bone marrow stem cells (BMSC) following 3D culture in IKVAV- and AG73-functionalized gels is shown in FIG. 26. The gel was cultured in 3D for 4 days. The supernatant was then removed and analyzed to identify secreted proteins. Expression profiles of proteins by stem cells encapsulated in peptide-functionalized gels were obtained. It was shown here, that factors, such as IL-1RA, sIL-6R, sTNFRI, sTNFRII, and TIMP 1, TIMP 2, TIMP 3, and TIMP 4 can be secreted by stem cells supported in the biocompatible 3D matrix composition.

Figure 27:
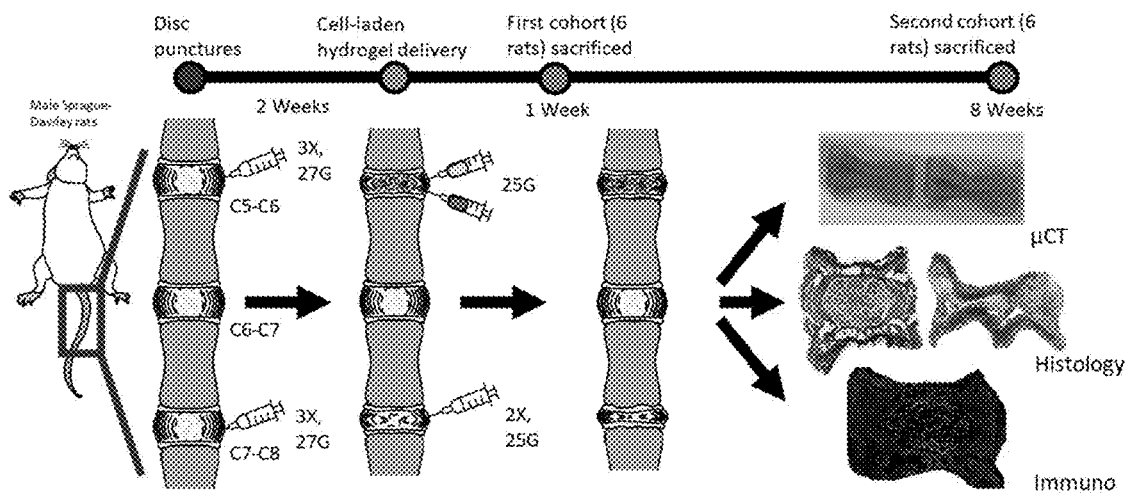
FIG. 27. Schematic of the in vivo approach.

A general schematic of the in vivo approach for delivering cell laden (e.g., NP cells or NP-precursors, stem cells, or other progenitors) biocompatible polymer delivery is shown in FIG. 27.

What is claimed is:

1. A biocompatible composition comprising:
a PEG maleimide biocompatible polymer component; and
at least one cell-adhesive peptide,
wherein
the cell-adhesive peptide is between about 5 and about 30 amino acids long;
the cell-adhesive peptide comprises at least one syndecan-binding or integrin-binding peptide selected from SEQ ID NO: 1, CGG-terminated SEQ ID NO: 1, SEQ ID NO: 2, and C-terminated SEQ ID NO: 2;
the cell-adhesive peptide is coupled to the biocompatible polymer component to form a cell-adhesive peptide-functionalized monomer;
the cell-adhesive peptide-functionalized monomer is crosslinked to form a cell-adhesive peptide-functionalized polymer, wherein the cell-adhesive peptide-functionalized polymer has a density greater than 10% (w/v);
the biocompatible composition has a stiffness of about 10 kPa; and
the biocompatible composition comprises a cell-adhesive peptide density between about 50 μM and about 100 μM sufficient to support nucleus pulposus (NP) cell-specific morphology, biosynthesis, or phenotype.

2. The biocompatible composition of claim 1, wherein the cell-adhesive peptide is derived from a sequence found in naturally occurring laminin proteins, a functional portion of the LG domains of full length laminin, isoforms thereof, or a functional fragment or variant thereof.

3. The biocompatible composition of claim 1, wherein the cell-adhesive peptide is a laminin-mimetic peptide.

4. The biocompatible composition of claim 3, wherein the laminin-mimetic peptide is a laminin-based integrin-binding peptide or a laminin-based syndecan-binding peptide.

5. The biocompatible composition of claim 1, comprising a first integrin-binding peptide and a second integrin-binding peptide.

6. The biocompatible composition of claim 1, wherein the biocompatible polymer component comprises a terminal component capable of conjugating a cell-adhesive peptide.

7. The biocompatible composition of claim 6, wherein the terminal component comprises maleimide, cysteine, or carboxylate.

8. The biocompatible composition of claim 1, wherein the cell-adhesive peptide-functionalized monomer is cross-linked via coupling of the biocompatible polymer component via side group coupling, a terminal group on the biocompatible polymer component, a sulfo-, a dithiol crosslinker, a PEG crosslinker, an amine, or EDC/NHS coupling.

9. The biocompatible composition of claim 8, wherein the dithiol crosslinker is SH-PEG-SH.

10. The biocompatible composition of claim 1, wherein if the cell-adhesive peptide density is increased, the biocompatible composition stiffness increases.

11. The biocompatible composition of claim 1, wherein the cell-adhesive peptide comprises a terminal group capable of conjugating to a biocompatible polymer component comprising a bioconjugation component capable of conjugating with the terminal group.

12. The biocompatible composition of claim 1, wherein the cell-adhesive peptide comprises a thiol terminal group capable of conjugating to a biocompatible polymer component comprising maleimide.

13. The biocompatible composition of claim 1, wherein the at least one cell-adhesive peptide is a combination of a syndecan-binding peptide and an integrin-binding peptide.

14. The biocompatible composition of claim 1, wherein the at least one cell-adhesive peptide is at least two of integrin-binding, syndecan-binding, or cadherin-binding peptides.

15. The biocompatible composition of claim 3, wherein the laminin-mimetic peptide further comprises a sequence selected from the group consisting of PPFLMLLKGSTR (SEQ ID NO: 3), EGYGEGYIGSR (SEQ ID NO: 4), AGQWHRVSRWG (SEQ ID NO: 5), KQN-CLSSRASFRGCVRNLRLSR (SEQ ID NO: 6), and combinations thereof.

16. The biocompatible composition of claim 1, wherein the cell-adhesive peptide-functionalized polymer density is between about 15% (w/v) and about 40% (w/v).

17. The biocompatible composition of claim 1, further comprising a population of undifferentiated precursor cells, a population of stem cells, a population of nucleus pulposus (NP) cell precursors, a population of adult primary NP cells, or a population of primary intervertebral disc (IVD) cells, or a combination thereof.

18. The biocompatible composition of claim 16, wherein the NP cell precursors are NP progenitor cells.

19. The biocompatible composition of claim 1, wherein the biocompatible composition comprises a cell having an NP cell-specific phenotype characterized by the gene expression of COL1A1, ACAN, COL2A1, GLUT1, or CDH2, or combinations thereof.

20. The biocompatible composition of claim 1, wherein the biocompatible composition comprises a population of NP cell-specific phenotype precursor cells selected from IVD cells, primary adult NP cells, NP precursor cells, adult NP cells, or pathological NP cells, or combinations thereof.

21. The biocompatible composition of claim 16, wherein the NP cell precursors are undifferentiated precursor cells.

22. The biocompatible composition of claim 1, further comprising at least one progenitor cell in its undifferentiated state.

23. The biocompatible composition of claim 1, wherein the biocompatible composition further comprises stem cells selected from adipose stromal/stem cells (ASCs), adipose-derived stem cells (ADSCs), amniotic fluid stem cells, bone marrow-derived mesenchymal stem/stromal cells (BMSCs), bone marrow stem cells, cord blood stem cells, embryonic stem (ES) cells, hematopoietic stem cells, induced pluripotent stem cells (iPSCs), mesenchymal stromal, non-embryonic (adult) stem cells, pluripotent stem cells (PSCs), progenitor cells, induced pluripotent stem (iPS) cells), induced pluripotent stem cells (iPSCs), mesenchymal stromal cells, mesenchymal stem cells (MSCs), cord blood stem cells, umbilical cord-derived progenitor cells, umbilical cord-MSCs, umbilical cord-derived progenitor cells, amniotic fluid stem cells, and other progenitor cells.

24. The biocompatible composition of claim 23, wherein the stem cells promote cell attachment, promote the secretion of inflammatory mediating factors, or promote the secretion of matrix degrading protease mediating factors.

25. The biocompatible composition of claim 24, wherein the inflammatory mediating factors are selected from interleukin (IL)-1 receptor agonist (RA), SIL-6R, soluble tumor necrosis factor receptor (sTNFR) I, sTNFRII, tissue inhibitor of metalloproteinases (TIMP) 1, TIMP 2, TIMP 3, TIMP 4, and combinations thereof.

26. The biocompatible composition of claim 1, wherein the biocompatible composition supports progenitor cell secretions of chemokines that exert an anti-inflammatory effect upon neighboring cells.

27. The biocompatible composition of claim 1, further comprising progenitor cells cultured in or on the biocompatible composition, wherein the progenitor cells secrete inflammatory-mediating factors that result in inflammatory mediating effects upon neighboring cells.

28. The biocompatible composition of claim 27, wherein the inflammatory-mediating factors are selected from IL-1RA, sIL-6R, sTNFRI, STNFRII, and combinations thereof.

29. The biocompatible composition of claim 1, further comprising progenitor cells cultured in or on the biocompatible composition, wherein the progenitor cells secrete protease mediating factors which result in protease mediating effects upon neighboring cells.

30. The biocompatible composition of claim 29, wherein the protease mediating factors are selected from TIMP_1, TIMP 2, TIMP_3, TIMP_4, and combinations thereof.

31. The biocompatible composition of claim 1, wherein the biocompatible composition supports progenitor cells capable of secreting extracellular matrix biosynthesis promoting chemokines within neighboring cells.

32. The biocompatible composition of claim 31, wherein anabolic effects are achieved through secretion of extracellular matrix proteins.

33. The biocompatible composition of claim 1, wherein the biocompatible composition is suitable for use as an injectable material mixed with cells or cell-free, wherein the biocompatible composition has a viscosity that does not exceed G' of 100 Pa and G" of 25 Pa at temperatures between about 4° C. and about 37° C.

34. The biocompatible composition of claim 1, wherein the biocompatible composition is suitable for delivery to a defect site when injected in its precursor form mixed with cells or cell-free through a 12 G-22 G needle.

35. The biocompatible composition of claim 1, wherein the biocompatible composition is a 3D cell supporting matrix or coats a tissue culture surface.

36. The biocompatible composition of claim 1, wherein the biocompatible composition is capable of being used in cell-polymer culture constructs in vitro in volumes between about 10 mL and about 1 mL and between about 0 million cells/mL and up to about 10 million cells/mL.

37. The biocompatible composition of claim 1, wherein the biocompatible composition delivers cells to an intervertebral disc.

38. The biocompatible composition of claim 1, wherein the cell-adhesive peptide densities and co-combinations of coupling to peptide-functionalized polymer components modulate a range of cell phenotypic changes.

39. The biocompatible composition of claim 1, wherein the biocompatible composition supports cell survival, when introduced to a population of cells, in a peptide-functionalized polymer component solution, and crosslinked into a three-dimensional construct.

40. The biocompatible composition of claim 1, wherein the biocompatible composition is capable of delivering and localizing NP precursor cells or primary human NP cells and peptide-functionalized polymer components to defects in an intervertebral disc in a subject.

41. A method of supporting adult human NP cells towards a healthy nucleus pulposus (NP) cell-specific phenotype or delivering undifferentiated progenitor cells comprising administering to a subject the biocompatible composition of claim 1.

42. The method of claim 41, wherein the subject has intervertebral disc degeneration or damage.

* * * * *

SEQUENCE LISTING

```
<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: synthetic peptide

<400> SEQUENCE: 1

Arg Lys Arg Leu Gln Val Gln Leu Ser Ile Arg Thr
1               5                   10

<210> SEQ ID NO 2
<211> LENGTH: 17
<212> TYPE: PRT
<213> ORGANISM: Artificial Sequence
<220> FEATURE:
<223> OTHER INFORMATION: synthetic peptide

<400> SEQUENCE: 2

Arg Ala Arg Lys Gln Ala Ala Ser Ile Lys Val Ala Val Ser Ala Asp
1               5                   10                  15

Arg
```

```
<210> SEQ ID NO 3
<211> LENGTH: 12
<212> TYPE: PRT
<213> ORGANISM: Artificial Sequence
<220> FEATURE:
<223> OTHER INFORMATION: synthetic peptide

<400> SEQUENCE: 3

Pro Pro Phe Leu Met Leu Leu Lys Gly Ser Thr Arg
1               5                   10

<210> SEQ ID NO 4
<211> LENGTH: 11
<212> TYPE: PRT
<213> ORGANISM: Artificial Sequence
<220> FEATURE:
<223> OTHER INFORMATION: synthetic peptide

<400> SEQUENCE: 4

Glu Gly Tyr Gly Glu Gly Tyr Ile Gly Ser Arg
1               5                   10

<210> SEQ ID NO 5
<211> LENGTH: 11
<212> TYPE: PRT
<213> ORGANISM: Artificial Sequence
<220> FEATURE:
<223> OTHER INFORMATION: synthetic peptide

<400> SEQUENCE: 5

Ala Gly Gln Trp His Arg Val Ser Arg Trp Gly
1               5                   10

<210> SEQ ID NO 6
<211> LENGTH: 22
<212> TYPE: PRT
<213> ORGANISM: Artificial Sequence
<220> FEATURE:
<223> OTHER INFORMATION: synthetic peptide

<400> SEQUENCE: 6

Lys Gln Asn Cys Leu Ser Ser Arg Ala Ser Phe Arg Gly Cys Val Arg
1               5                   10                  15

Asn Leu Arg Leu Ser Arg
            20
```